US009981919B2

(12) United States Patent
Guillemont et al.

(10) Patent No.: US 9,981,919 B2
(45) Date of Patent: *May 29, 2018

(54) HIV REPLICATION INHIBITING PYRIMIDINES

(71) Applicant: Janssen Pharmaceutica NV, Beerse (BE)

(72) Inventors: Jérôme Emile Georges Guillemont, Andé (FR); Patrice Palandjian, Louviers (FR); Marc René de Jonge, Leidschendam (NL); Lucien Maria Henricus Koymans, Retie (BE); Hendrik Maarten Vinkers, Antwerpen (BE); Frederik Frans Desiré Daeyaert, Beerse (BE); Jan Heeres, Vosselaar (BE); Koen Jeanne Alfons Van Aken, Kortrijk (BE); Paulus Joannes Lewi; Paul Adriaan Jan Janssen

(73) Assignee: Janssen Pharmaceutical N.V., Beerse (BE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/655,570

(22) Filed: Jul. 20, 2017

(65) Prior Publication Data

US 2017/0320835 A1 Nov. 9, 2017

Related U.S. Application Data

(60) Continuation of application No. 15/406,918, filed on Jan. 16, 2017, now abandoned, which is a
(Continued)

(30) Foreign Application Priority Data

Aug. 13, 2001 (EP) .................................. 01203090
Jun. 10, 2002 (EP) .................................. 02077748

(51) Int. Cl.
*C07D 239/24* (2006.01)
*C07D 401/12* (2006.01)
(Continued)

(52) U.S. Cl.
CPC .......... *C07D 239/48* (2013.01); *A61K 31/505* (2013.01); *A61K 31/506* (2013.01);
(Continued)

(58) Field of Classification Search
None
See application file for complete search history.

(56) References Cited

U.S. PATENT DOCUMENTS 3,459,731 A 8/1969 Gramera et al.
3,953,398 A 4/1976 Kline
(Continued)

FOREIGN PATENT DOCUMENTS

CA 2324919 10/1999
DE 19-945982 A1 9/1999
(Continued)

OTHER PUBLICATIONS

Balzarini, et al., "Identification of Novel Thiocarboxanilide Derivatives That Suppress a Variety of Drug-Resistant Mutant Human Immunodeficiency Virus Type 1 Strains at a Potency Similar to That for Wild-Type Virus," Antimicrobial Agents and Chemotherapy, 40(6): 1454-1466 (1996).

(Continued)

*Primary Examiner* — Emily Bernhardt

(57) ABSTRACT

This invention concerns HIV replication inhibitors of formula (I)

the N-oxides, the pharmaceutically acceptable addition salts, the quaternary amines and the stereochemically isomeric forms thereof, wherein the ring containing $-a^1=a^2-a^3=a^4-$ and $-b^1=b^2-b^3=b^4-$ represents phenyl, pyridyl, pyrimidinyl, pirazinyl, pyridazinyl; n is 0 to 5; m is 1 to 4; $R^1$ is hydrogen; aryl; formyl; $C_{1-6}$alkylcarbonyl; $C_{1-6}$alkyl; $C_{1-6}$alkyloxycarbonyl; substituted $C_{1-6}$alkyl, $C_{1-6}$alkylcarbonyl, $C_{1-6}$alkyloxycarbonyl, $C_{1-6}$alkylcarbonyloxy; substituted $C_{1-6}$alkyloxy$C_{1-6}$alkylcarbonyl; $R^2$ is hydroxy, halo, optionally substituted $C_{1-6}$alkyl, $C_{3-7}$cycloalkyl, optionally substituted $C_{2-6}$alkenyl, optionally substituted $C_{2-6}$alkynyl, $C_{1-6}$alkyloxy, $C_{1-6}$alkyloxycarbonyl, carboxyl, cyano, nitro, amino, mono- or di($C_{1-6}$alkyl)amino, polyhalomethyl, polyhalomethyloxy, polyhalomethylthio, $-S(=O)_pR^6$, $-NH-S(=O)_pR^6$, $-C(=O)R^6$, $-NHC(=O)H$, $-C(=O)NHNH_2$, $-NHC(=O)R^6$, $-C(=NH)R^6$ or a 5-membered heterocycle; $X_1$ is $-NR^5-$, $-NH-NH-$, $-N=N-$, $-O-$, $-C(=O)-$, $C_{1-4}$alkanediyl, $-CHOH-$, $-S-$, $-S(=O)_p-$, $-X_2-C_{1-4}$alkanediyl- or $-C_{1-4}$alkanediyl-$X_2-$; $R^3$ is $NHR^{13}$; $NR^{13}R^{14}$; $-C(=O)-NHR^{13}$; $-C(=O)-NR^{13}R^{14}$; $-C(=O)-R^{15}$; $-CH=N-NH-C(=O)-R^{16}$; substituted $C_{1-6}$alkyl; optionally substituted $C_{1-6}$alkyloxy$C_{1-6}$alkyl; substituted $C_{2-6}$alkenyl; substituted $C_{2-6}$alkynyl; $C_{1-6}$alkyl substituted with hydroxy and a second substituent; $-C(=N-O-R^8)-C_{1-4}$alkyl; $R^7$; or $-X_3-R^7$; $R^4$ is halo, hydroxy, $C_{1-6}$alkyl, $C_{3-7}$cycloalkyl, $C_{1-6}$alkyloxy, cyano, nitro, polyhalo$C_{1-6}$alkyl, polyhalo$C_{1-6}$alkyloxy, aminocarbonyl, $C_{1-6}$alkyloxycarbonyl, $C_{1-6}$alkylcarbonyl, formyl, amino, mono- or di($C_{1-4}$alkyl)amino; their use as a medicine, their processes for preparation and pharmaceutical compositions comprising them.

7 Claims, No Drawings

Related U.S. Application Data continuation of application No. 14/451,761, filed on Aug. 5, 2014, now Pat. No. 9,580,392, which is a division of application No. 13/249,796, filed on Sep. 30, 2011, now abandoned, which is a continuation of application No. 11/474,855, filed on Jun. 26, 2006, now Pat. No. 8,080,551, which is a continuation of application No. 10/485,636, filed as application No. PCT/EP02/08953 on Aug. 9, 2002, now Pat. No. 7,125,879.

(51) Int. Cl.

| | |
|---|---|
| C07D 401/14 | (2006.01) |
| C07D 403/12 | (2006.01) |
| C07D 413/02 | (2006.01) |
| C07D 417/02 | (2006.01) |
| A61K 31/505 | (2006.01) |
| A61K 31/506 | (2006.01) |
| A61K 31/5377 | (2006.01) |
| C07D 239/48 | (2006.01) |
| C07C 255/42 | (2006.01) |
| C07C 257/12 | (2006.01) |
| C07D 239/47 | (2006.01) |
| C07D 405/12 | (2006.01) |
| C07D 409/12 | (2006.01) |
| C07D 413/12 | (2006.01) |
| C07D 417/12 | (2006.01) |
| A61K 31/541 | (2006.01) |
| A61K 31/551 | (2006.01) |
| A61K 45/06 | (2006.01) |

(52) U.S. Cl.
CPC ........ A61K 31/5377 (2013.01); A61K 31/541 (2013.01); A61K 31/551 (2013.01); A61K 45/06 (2013.01); C07C 255/42 (2013.01); C07C 257/12 (2013.01); C07D 239/47 (2013.01); C07D 401/12 (2013.01); C07D 401/14 (2013.01); C07D 403/12 (2013.01); C07D 405/12 (2013.01); C07D 409/12 (2013.01); C07D 413/12 (2013.01); C07D 417/12 (2013.01)

(56) References Cited

U.S. PATENT DOCUMENTS

| | | | |
|---|---|---|---|
| 5,691,364 | A | 11/1997 | Buckman et al. |
| 5,958,935 | A | 9/1999 | Davis et al. |
| 6,197,779 | B1 | 3/2001 | Andries et al. |
| 6,838,464 | B2 | 1/2005 | Pease et al. |
| 6,949,544 | B2 | 9/2005 | Bethiel et al. |
| 6,982,091 | B2 | 1/2006 | Pauletti et al. |
| 7,060,827 | B2 | 6/2006 | Singh et al. |
| 7,125,879 | B2 | 10/2006 | Guillemont et al. |
| 7,399,856 | B2 | 7/2008 | Schils et al. |
| 7,638,522 | B2 | 12/2009 | Guillemont et al. |
| 8,080,551 | B2 | 12/2011 | Guillemont et al. |
| 8,101,629 | B2 | 1/2012 | Guillemont et al. |
| 8,828,982 | B2 | 9/2014 | Heeres et al. |
| 9,192,577 | B2 | 11/2015 | Vandercruys et al. |
| 2006/0034797 | A1 | 2/2006 | Arien et al. |
| 2009/0148531 | A1 | 6/2009 | Hantke et al. |
| 2013/0040961 | A1 | 2/2013 | Riggs-Sauthier et al. |

FOREIGN PATENT DOCUMENTS

| | | |
|---|---|---|
| EP | 0002341 B1 | 1/1982 |
| EP | 1002795 A1 | 5/1999 |
| EP | 0945443 A1 | 9/1999 |
| JP | 58079920 | 5/1983 |
| JP | 2000-35628 A | 2/2000 |
| WO | WO 91/18887 A1 | 12/1991 |
| WO | WO 97/18839 A1 | 5/1997 |
| WO | WO 97/19065 A1 | 5/1997 |
| WO | WO 97/24350 | 7/1997 |
| WO | WO 98/41512 A1 | 9/1998 |
| WO | WO 99/50250 A1 | 10/1999 |
| WO | WO 00/12485 A1 | 3/2000 |
| WO | WO 00/27825 A1 | 5/2000 |
| WO | WO 00/53610 A2 | 9/2000 |
| WO | WO 00/62778 A1 | 10/2000 |
| WO | WO 00/78731 A1 | 12/2000 |
| WO | WO 01/22938 A1 | 4/2001 |
| WO | WO 01/23362 A2 | 4/2001 |
| WO | WO 01/60816 A1 | 8/2001 |
| WO | WO 01/64654 A1 | 9/2001 |
| WO | WO 01/64656 A1 | 9/2001 |
| WO | WO 01/85699 A2 | 11/2001 |
| WO | WO 01/85700 A | 11/2001 |
| WO | WO 02/08226 A2 | 1/2002 |
| WO | WO 02/70470 A2 | 9/2002 |
| WO | WO 03/16306 A1 | 2/2003 |
| WO | WO 04/16581 A1 | 2/2003 |
| WO | WO 04/50058 A2 | 6/2004 |
| WO | WO 2004/050068 | 6/2004 |
| WO | WO 2004/069812 | 8/2004 |
| WO | WO 05/21001 A1 | 3/2005 |

OTHER PUBLICATIONS

Berge, et al., "Pharmaceutical Salts," Journal of Pharmaceutical Sciences, 66(1): 1-19 (1977).

Das, et al., "Crystal Structures of 8-CL and 9-CL TIBO Complexed With Wild-Type HIV-1 RT and 8-CL TIBO Complexed With the TYR181 CYS HIV-1 RT Drug-Resistant Mutant," Journal of Molecular Biology, 264: 1085-1100 (1996).

Fisher, et al., "Correlation of Metabolism, Covalent Binding and Toxicity for a Serial of Bromobenzene Derivatives Using Rat Liver Slices In Vitro," Chemical-Biological Interactions, 88: 191-208 (1993).

Ghosh, et al., "Alterations to the Primer Grip of P66 HIV-1 Reverse Transcriptase and Their Consequences for Template-Primer Utilization," Biochemistry, 35: 8553-8562 (1996).

Philip L. Gould, "Salt Selection for Basic Drugs," International Journal of Pharmaceuticals, 33: 201-217 (1986).

Hsiou, et al., "Structures of TYR188LEU Mutant and Wild-Type HIV-1 Reverse Transcriptase Complexed With the Non-Nucleoside Inhibitor HBY 097: Inhibitor Flexibility Is a Useful Design Feature for Reducing Drug Resistance," Journal of Molecular Biology, 284: 313-323 (1998).

Hsiou, et al., "Structure of Unliganded HIV-1 Reverse Transcriptase at 2.7 Resolution: Implications of Conformational Changes for Polymerization and Inhibition Mechanisms," Structure, 4: 853-860 (1995).

Kelder, eta l., "Polar Molecular Surface as a Dominating Determinant for Oral Absorption and Brain Penetration of Drugs," Pharmaceutical Research, 16(10): 1514-1519 (1999).

Morrison, et al., "Organic Chemistry," Sixth Edition, Prentice Hall of India, Chapter 22, 365-367 (1992).

Pumford, et al., "Protein Targets of Xenobiotic Reactive Intermediates," Annual Review of Pharmacology and Toxicology, 37: 91-117 (1997).

Rodgers, et al., "The Structure of Unliganded Reverse Transcriptase From the Human Immunodeficiency Virus Type 1," Proceedings of the National Academy of Science USA, 92: 1222-1226 (1995).

"Widespread 'Test-And-Treat' HIV Policies Could Increase Dangerous Drug Resistance", Science Daily, University of Southern California, Mar. 18, 2013. (3 Pages) Science Daily, Mar. 18, 2013.

Thaczuk, Nam—AIDSMAP, 2013, "How Does Type of Treatment Affect Resistance?"

Weller, et al., "In Vitro Metabolism and Covalent Binding Among Ortho-Substituted Bromobenzenes of Varying Hepatotoxicity," Drug Metabolism and Disposition, 16: 232-237 (1988).

(56) References Cited

OTHER PUBLICATIONS

D'Auria, et al., "Photochemical Dimerization in Solution of Arylacrylonitrile Derivatives," Tetrahedron, 53(51): 17307-17316 (1997).

Denton, et al., "Antiretroviral Pre-Exposure Prophylaxis Prevents Vaginal Transmission of HIV-1 in Humanized BLT Mice," PLOS Medicine, (2008).

Gilead Sciences, Inc., "Gilead Initiates Study 934, A 48-Week Clinical Trial Evaluating VILREAD™ and EMTRIVA™ Versus COMBIVIR™," Internet Article, Online, Aug. 11, 2003.

Koyanagi, et al., "Selective Cytotoxicity of AIDS Virus Infection Towards HTLV-1-Transformed Cell Lines," International Journal of Cancer, 36: 445-451 (1985).

Larock, "Interconversion of Nitriles, Carboxylic Acids and Derivaties," John Wiley & Sons, Inc., 1983-1985 (1999).

Ludovici, et al., "Evolution of Anti-HIV Drug Candidates. Part 3: Diarylpyrimidine (DAPY) Analogues," Bioorganiz & Medicinal Chemistry Letters, 11: 2235-2239 (2001).

Mayo Clinic, HIV Infection Symptoms According to Infection Stage, www.mayoclinic.com/health/his-aids/ds00005/dsection-symptoms (Nov. 2, 2009).

Miles, "The Growing HIV Pandemic," HIV Diagnoses: Community Practitioner, 78(8): 292-294 (2005).

Pavia, "Abacavir/Lamiviudne in Connection With Efavirenz, Amprenavir/Ritonavir or Stavudine," The XIV International AIDS Conference, Jul. 9, 2002.

Squires, "An Introduction to Nucleoside and Nucleotide Analogues," Antiviral Therapy, 6 Supp. 3, 1-14 (2001).

Supuran, et al., "Carbonic Anhydrase Inhibitors: Synthesis of Sulfonamides Incorporating 2,4,6-Trisubstituted-Pyridinium-Ethylcarboxamido Moieties Possessing Membrane-Impermeability and In Vivo Selectively for the Membrane-Bound (CA IV) Versus the Cytosolic (CA 1 and CA11) Isozymes," Journal of Enzyme Inhibitor and Medicinal Chemistry, 15: 381-340 (2000).

Young, "Can Abacavir Be Given Once-A-Day?", The 43$^{rd}$ Interscience Conference on Antimicrobial Agents and Chemotherapy, Sep. 16, 2003.

Gennaro, "Remington Pharmacy," 19$^{th}$ Edition, Medica Panmericana, 230-235 and 2226-2234 (1995) (English Translation and Certification Pages).

Nogradi et al "Dimethyl-B-Cyclodextrin" Drugs of the Future 1984 vol. 9 (8) pp. 577-578.

Gilead Press Release XP-002314669 (2005).

Mayo Clinic, HIV Infection Symptoms According to Infection Stage; <http://ww\n.ma yoclinic.com/heal th/hiv aids/ds00005/dsection=symptoms>, Updated Jun. 20, 2008, Downloaded Feb. 27, 2009.

Canadian Search Report dated Feb. 19, 2007 for corresponding application No. CA 2,452,217.

European Search Report dated Dec. 5, 2001 for corresponding application No. EP 01203090.4

International Search Report, dated Nov. 26, 2002, for Corresponding Application No. PCT/EP2002/08953.

International Preliminary Examination Report dated Nov. 30, 2004 for Corresponding Application No. PCT/EP03/50366.

International Preliminary Examination Report dated Dec. 3, 2003 for Corresponding Application No. PCT/EP2002/08953.

Office Action Dispatched May 12, 2009 for Japanese Patent Application No. 521229/03.

HIV REPLICATION INHIBITING PYRIMIDINES

CROSS REFERENCE TO RELATED APPLICATIONS

This application is a continuation of U.S. application Ser. No. 15/406,918, filed 16 Jan. 2017, pending, which is a continuation of U.S. application Ser. No. 14/451,761, filed 5 Aug. 2014, now U.S. Pat. No. 9,580,392, which is a divisional of U.S. application Ser. No. 13/249,796, filed 30 Sep. 2011, abandoned, which is a continuation of Ser. No. 11/474,855, filed Jun. 26, 2006, now U.S. Pat. No. 8,080,551, which is a continuation of U.S. application Ser. No. 10/485,636, filed Feb. 3, 2004, now U.S. Pat. No. 7,125,879, which is a national stage of PCT Application No. PCT/EP02/08953, filed Aug. 9, 2002, which claims priority for EPO Patent Application No. 01203090.4, filed Aug. 13, 2001 and EPO Patent Application No. 02077748.8, filed Jun. 10, 2002, all of which are hereby incorporated by reference in their entirety.

BACKGROUND

The present invention is concerned with pyrimidine derivatives having HIV (Human Immunodeficiency Virus) replication inhibiting properties. The invention further relates to methods for their preparation and pharmaceutical compositions comprising them. The invention also relates to the use of said compounds for the manufacture of a medicament for the prevention or the treatment of HIV infection.

Compounds structurally related to the present compounds are disclosed in the prior art.

WO 99/50250 and WO 00/27825 disclose substituted aminopyrimidines having HIV replication inhibiting properties.

WO 97/19065 discloses substituted 2-anilinopyrimidines useful as protein kinase inhibitors.

WO 00/62778 concerns cyclic protein tyrosine kinase inhibitors.

WO 98/41512 describes substituted 2-anilinopyrimidines useful as protein kinase inhibitors.

U.S. Pat. No. 5,691,364 describes benzamidine derivatives and their use as anti-coagulants.

WO 00/78731 describes 5-cyano-2-aminopyrimidine derivatives as KDR kinase or FGFr kinase inhibitors useful in the prophylaxis and treatment of diseases associated with angiogenesis.

The compounds of the invention differ from the prior art compounds in structure, pharmacological activity and/or pharmacological potency.

Unexpectedly, it has been found that the compounds of the invention have an improved ability to inhibit the replication of Human Immunodeficiency Virus (HIV), in particular they have an improved ability to inhibit the replication of mutant strains, i.e. strains which have become resistant to art-known drug(s) (drug or multidrug resistant HIV strains).

SUMMARY OF THE INVENTION

The present invention concerns a compound of formula (I)

a N-oxide, a pharmaceutically acceptable addition salt, a quaternary amine or a stereochemically isomeric form thereof, wherein -$a^1$=$a^2$-$a^3$=$a^4$- represents a bivalent radical of formula

| —CH=CH—CH=CH— | (a-1); |
| —N=CH—CH=CH— | (a-2); |
| —N=CH—N=CH— | (a-3); |
| —N=CH—CH=N— | (a-4); |
| —N=N—CH=CH— | (a-5); |

-$b^1$=$b^2$-$b^3$=$b^4$- represents a bivalent radical of formula

| —CH=CH—CH=CH— | (b-1); |
| —N=CH—CH=CH— | (b-2); |
| —N=CH—N=CH— | (b-3); |
| —N=CH—CH=N— | (b-4); |
| —N=N—CH=CH— | (b-5); | n is 0, 1, 2, 3 or 4; and in case -$a^1$=$a^2$-$a^3$=$a^4$- is (a-1), then n may also be 5;

m is 1, 2, 3 and in case -$b^1$=$b^2$-$b^3$=$b^4$- is (b-1), then m may also be 4;

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl substituted with $C_{1-6}$alkyloxycarbonyl;

each $R^2$ independently is hydroxy, halo, $C_{1-6}$alkyl optionally substituted with cyano or —C(=O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxycarbonyl, carboxyl, cyano, nitro, amino, mono- or di($C_{1-6}$alkyl)amino, polyhalomethyl, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$ or a radical of formula (c)

wherein each $A_1$ independently is N, CH or C$R^6$; and
$A_2$ is NH, O, S or N$R^6$;

$X_1$ is —NR$^5$—, —NH—NH—, —N=N—, —O—, —C(=O)—, C$_{1-4}$alkanediyl, —CHOH—, —S—, —S(=O)$_p$—, —X$_2$—C$_{1-4}$alkanediyl- or —C$_{1-4}$alkanediyl-X$_2$—;

$X_2$ is —NR$^5$—, —NH—NH—, —N=N—, —O—, —C(=O)—, —CHOH—, —S—, —S(=O)$_p$—;

$R^3$ is NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; C$_{1-6}$alkyl substituted with one or more substituents each independently selected from cyano, NR$^9$R$^{10}$, —C(=O)—NR$^9$R$^{10}$, —C(=O)—C$_{1-6}$alkyl or R$^7$; C$_{1-6}$alkyl substituted with one or more substituents each independently selected from cyano, NR$^9$R$^{10}$, —C(=O)—NR$^9$R$^{10}$, —C(=O)—C$_{1-6}$alkyl or R$^7$ and wherein 2 hydrogen atoms bound at the same carbon atom are replaced by C$_{1-4}$alkanediyl; C$_{1-6}$alkyl substituted with hydroxy and a second substituent selected from cyano, NR$^9$R$^{10}$, —C(=O)—NR$^9$R$^{10}$, —C(=O)—C$_{1-6}$alkyl or R$^7$; C$_{1-6}$alkyloxyC$_{1-6}$alkyl optionally substituted with one or more substituents each independently selected from cyano, NR$^9$R$^{10}$, —C(=O)—NR$^9$R$^{10}$, —C(=O)—C$_{1-6}$alkyl or R$^7$; C$_{2-6}$alkenyl substituted with one or more substituents each independently selected from halo, cyano, NR$^9$R$^{10}$, —C(=O)—NR$^9$R$^{10}$, —C(=O)—C$_{1-6}$alkyl or R$^7$; C$_{2-6}$alkynyl substituted with one or more substituents each independently selected from halo, cyano, NR$^9$R$^{10}$, —C(=O)—NR$^9$R$^{10}$, —C(=O)—C$_{1-6}$alkyl or R$^7$; —C(=N—O—R)—C$_{1-4}$alkyl; R$^7$ or —X$_3$—R$^7$;

$X_3$ is —NR$^5$—, —NH—NH—, —N=N—, —O—, —C(=O)—, —S—, —S(=O)$_p$—, —X$_2$—C$_{1-4}$alkanediyl-, —C$_{1-4}$alkanediyl-X$_{2a}$—, —C$_{1-4}$alkanediyl-X$_{2b}$—C$_{1-4}$alkanediyl, —C(=N—OR$^8$)—C$_{1-4}$alkanediyl-;

with X$_{2a}$ being —NH—NH—, —N=N—, —O—, —C(=O)—, —S—, —S(=O)$_p$—; and with X$_{2b}$ being —NH—NH—, —N=N—, —C(=O)—, —S—, —S(=O)$_p$—;

$R^4$ is halo, hydroxy, C$_{1-6}$alkyl, C$_{3-7}$cycloalkyl, C$_{1-6}$alkyloxy, cyano, nitro, polyhaloC$_{1-6}$alkyl, polyhaloC$_{1-6}$alkyloxy, aminocarbonyl, C$_{1-6}$alkyloxycarbonyl, C$_{1-6}$alkylcarbonyl, formyl, amino, mono- or di(C$_{1-4}$alkyl)amino or R$^7$;

$R^5$ is hydrogen; aryl; formyl; C$_{1-6}$alkylcarbonyl; C$_{1-6}$alkyl; C$_{1-6}$alkyloxycarbonyl; C$_{1-6}$alkyl substituted with formyl, C$_{1-6}$alkylcarbonyl, C$_{1-6}$alkyloxycarbonyl or C$_{1-6}$alkylcarbonyloxy; C$_{1-6}$alkyloxyC$_{1-6}$alkylcarbonyl substituted with C$_{1-6}$alkyloxycarbonyl;

$R^6$ is C$_{1-4}$alkyl, amino, mono- or di(C$_{1-4}$alkyl)amino or polyhaloC$_{1-4}$alkyl;

$R^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$), R$^{7a}$, —X$_3$—R$^{7a}$ or R$^{7a}$—C$_{1-4}$alkyl;

$R^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, formyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, —CH(=N—O—R$^8$);

$R^8$ is hydrogen, C$_{1-4}$alkyl, aryl or arylC$_{1-4}$alkyl;

$R^9$ and $R^{10}$ each independently are hydrogen; hydroxy; C$_{1-6}$alkyl; C$_{1-6}$alkyloxy; C$_{1-6}$alkylcarbonyl; C$_{1-6}$alkyloxycarbonyl; amino; mono- or di(C$_{1-6}$alkyl)amino; mono- or di(C$_{1-6}$alkyl)aminocarbonyl; —CH(=NR$^{11}$) or R$^7$, wherein each of the aforementioned C$_{1-6}$alkyl groups may optionally and each individually be substituted with one or two substituents each independently selected from hydroxy, C$_{1-6}$alkyloxy, hydroxyC$_{1-6}$alkyloxy, carboxyl, C$_{1-6}$alkyloxycarbonyl, cyano, amino, imino, mono- or di(C$_{1-4}$alkyl)amino, polyhalomethyl, polyhalomethyloxy, polyhalomethylthio, —S(=O)$_p$R$^6$, —NH—S(=O)$_p$R$^6$, —C(=O)R$^6$, —NHC(=O)H, —C(=O)NHNH$_2$, —NHC(=O)R$^6$, —C(=NH)R$^6$, R$^7$; or R$^9$ and R$^{10}$ may be taken together to form a bivalent or trivalent radical of formula

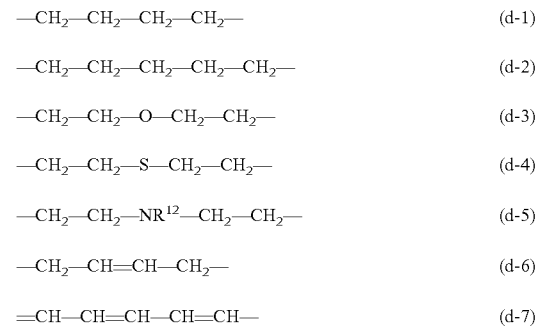

$R^{11}$ is cyano; C$_{1-4}$alkyl optionally substituted with C$_{1-4}$alkyloxy, cyano, amino, mono- or di(C$_{1-4}$alkyl)amino or aminocarbonyl; C$_{1-4}$alkylcarbonyl; C$_{1-4}$alkyloxycarbonyl; aminocarbonyl; mono- or di(C$_{1-4}$alkyl)aminocarbonyl;

$R^{12}$ is hydrogen or C$_{1-4}$alkyl;

$R^{13}$ and $R^{14}$ each independently are C$_{1-6}$alkyl optionally substituted with cyano or aminocarbonyl, C$_{2-6}$alkenyl optionally substituted with cyano or aminocarbonyl, C$_{2-6}$alkynyl optionally substituted with cyano or aminocarbonyl;

$R^{15}$ is C$_{1-6}$alkyl substituted with cyano or aminocarbonyl;

$R^{16}$ is C$_{1-6}$alkyl optionally substituted with cyano or aminocarbonyl, or R$^7$;

p is 1 or 2;

aryl is phenyl or phenyl substituted with one, two, three, four or five substituents each independently selected from halo, hydroxy, mercapto, C$_{1-6}$alkyl, hydroxyC$_{1-6}$alkyl, aminoC$_{1-6}$alkyl, mono or di(C$_{1-6}$alkyl)aminoC$_{1-6}$alkyl, C$_{1-6}$alkylcarbonyl, C$_{3-7}$cycloalkyl, C$_{1-6}$alkyloxy, C$_{1-6}$alkyloxycarbonyl, C$_{1-6}$alkylthio, cyano, nitro, polyhaloC$_{1-6}$alkyl, polyhaloC$_{1-6}$alkyloxy, aminocarbonyl, R$^7$ or —X$_3$—R$^7$.

DETAILED DESCRIPTION OF THE INVENTION

As used hereinbefore or hereinafter C$_{1-4}$alkyl as a group or part of a group defines straight or branched chain saturated hydrocarbon radicals having from 1 to 4 carbon atoms such as methyl, ethyl, propyl, 1-methylethyl, butyl; C$_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methylbutyl and the like; $C_{2-6}$alkyl as a group or part of a group defines straight or branched chain saturated hydrocarbon radicals having from 2 to 6 carbon atoms such as ethyl, propyl, 1-methylethyl, butyl, pentyl, hexyl, 2-methylbutyl and the like; $C_{1-4}$alkanediyl defines straight or branched chain saturated bivalent hydrocarbon radicals having from 1 to 4 carbon atoms such as methylene, 1,2-ethanediyl or 1,2-ethylidene, 1,3-propanediyl or 1,3-propylidene, 1,4-butanediyl or 1,4-butylidene and the like; $C_{3-7}$cycloalkyl is generic to cyclopropyl, cyclobutyl, cyclopentyl, cyclohexyl and cycloheptyl; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like; a monocyclic, bicyclic or tricyclic saturated carbocycle represents a ring system consisting of 1, 2 or 3 rings, said ring system being composed of only carbon atoms and said ring system containing only single bonds; a monocyclic, bicyclic or tricyclic partially saturated carbocycle represents a ring system consisting of 1, 2 or 3 rings, said ring system being composed of only carbon atoms and comprising at least one double bond provided that the ring system is not an aromatic ring system; a monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n+2 electrons, that is with 6, 10, 14 etc. t-electrons (rule of Hückel); a monocyclic, bicyclic or tricyclic saturated heterocycle represents a ring system consisting of 1, 2 or 3 rings and comprising at least one heteroatom selected from O, N or S, said ring system containing only single bonds; a monocyclic, bicyclic or tricyclic partially saturated heterocycle represents a ring system consisting of 1, 2 or 3 rings and comprising at least one heteroatom selected from O, N or S, and at least one double bond provided that the ring system is not an aromatic ring system; a monocyclic, bicyclic or tricyclic aromatic heterocycle represents an aromatic ring system consisting of 1, 2 or 3 rings and comprising at least one heteroatom selected from O, N or S.

Particular examples of monocyclic, bicyclic or tricyclic saturated carbocycles are cyclopropyl, cyclobutyl, cyclopentyl, cyclohexyl, cycloheptyl, cyclooctyl, bicyclo[4,2,0]octanyl, cyclononanyl, cyclodecanyl, decahydronapthalenyl, tetradecahydroanthracenyl and the like.

Particular examples of monocyclic, bicyclic or tricyclic partially saturated carbocycles are cyclopropenyl, cyclobutenyl, cyclopentenyl, cyclohexenyl, cycloheptenyl, cyclo-octenyl, bicyclo[4,2,0]octenyl, cyclononenyl, cyclodecenyl, octahydronaphthalenyl, 1,2,3,4-tetrahydronaphthalenyl, 1,2,3,4,4a,9,9a,10-octahydro-anthracenyl and the like.

Particular examples of monocyclic, bicyclic or tricyclic aromatic carbocycles are phenyl, naphthalenyl, anthracenyl.

Particular examples of monocyclic, bicyclic or tricyclic saturated heterocycles are tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, decahydroquinolinyl, octahydroindolyl and the like.

Particular examples of monocyclic, bicyclic or tricyclic partially saturated heterocycles are pyrrolinyl, imidazolinyl, pyrazolinyl, 2,3-dihydrobenzofuranyl, 1,3-benzodioxolyl, 2,3-dihydro-1,4-benzodioxinyl, indolinyl and the like.

Particular examples of monocyclic, bicyclic or tricyclic aromatic heterocycles are azetyl, oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolo-triazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-4}$alkyl or polyhalo$C_{1-6}$alkyl as a group or part of a group is defined as mono- or polyhalosubstituted $C_{1-4}$alkyl or $C_{1-6}$alkyl, for example, the groups defined in halomethyl, 1,1-difluoro-ethyl and the like. In case more than one halogen atoms are attached to an alkyl group within the definition of polyhalomethyl, polyhalo$C_{1-4}$alkyl or polyhalo$C_{1-6}$alkyl, they may be the same or different.

The term heterocycle in the definition of $R^7$ or $R^{7a}$ is meant to include all the possible isomeric forms of the heterocycles, for instance, pyrrolyl comprises 1H-pyrrolyl and 2H-pyrrolyl.

The carbocycle or heterocycle in the definition of $R^7$ or $R^{7a}$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

When any variable (e.g. $R^7$, $X_2$) occurs more than one time in any constituent, each definition is independent.

Lines drawn from substituents into ring systems indicate that the bond may be attached to any of the suitable ring atoms.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer.

In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (I) are obviously intended to be embraced within the scope of this invention.

For some of the compounds of formula (I), their prodrugs, N-oxides, salts, solvates, quaternary amines or metal complexes and the intermediates used in the preparation thereof, the absolute stereochemical configuration was not experimentally determined. In these cases the stereoisomeric form which was first isolated is designated as "A" and the second as "B", without further reference to the actual stereochemical configuration. However, said "A" and "B" stereoisomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction. In case "A" and "B" are stereoisomeric mixtures, they can be further separated whereby the respective first fractions isolated are designated "A1" and "B1" and the second as "A2" and "B2", without further reference to the actual stereochemical configuration.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I) which are stereochemically pure.

Whenever used hereinbefore or hereinafter that substituents can be selected each independently out of a list of numerous definitions, such as for example for $R^9$ and $R^{10}$, all possible combinations are intended which are chemically possible and which lead to chemically stable molecules.

A particular group of compounds are those compounds of formula (I) wherein $R^3$ is $C_{1-6}$alkyl substituted with at least one substituent selected from cyano, aminocarbonyl, $NR^9R^{10}$ or $R^7$; $C_{1-6}$alkyl substituted with at least one substituent selected from cyano, aminocarbonyl, $NR^9R^{10}$ or $R^7$ and wherein 2 hydrogen atoms bound at the same carbon atom are replaced by $C_{1-4}$alkanediyl; $C_{1-6}$alkyl substituted with hydroxy and a second substituent selected from cyano, aminocarbonyl, $NR^9R^{10}$ or $R^7$; $C_{1-6}$alkyloxy$C_{1-6}$alkyl substituted with at least one substituent selected from cyano, aminocarbonyl, $NR^9R^{10}$ or $R^7$; $C_{2-6}$alkenyl substituted with at least one substituent selected from cyano, aminocarbonyl, $NR^9R^{10}$ or $R^7$; $C_{2-6}$alkynyl substituted with at least one substituent selected from cyano, aminocarbonyl, $NR^9R^{10}$ or $R^7$; —C(=N—O—$R^8$)—$C_{1-4}$alkyl; $R^7$ or —$X_3$—$R^7$; $R^4$ is halo, hydroxy, $C_{1-6}$alkyl, $C_{3-7}$cycloalkyl, $C_{1-6}$alkyloxy, cyano, nitro, polyhalo$C_{1-6}$alkyl, polyhalo$C_{1-6}$alkyloxy, aminocarbonyl, $C_{1-6}$alkyloxycarbonyl, $C_{1-6}$alkylcarbonyl, formyl, amino, mono- or di($C_{1-4}$alkyl)amino; $R^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, $R^{7a}$, —$X_3$—$R^{7a}$ or $R^{7a}$—$C_{1-4}$alkyl; $R^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl) amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl; $R^9$ and $R^{10}$ each independently are hydrogen; hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl or $R^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl) amino, polyhalomethyl, polyhalomethyloxy, polyhalomethylthio, —S(=O)$_p$$R^6$, —NH—S(=O)$_p$$R^6$, —C(=O)$R^6$, —NHC(=O)H, —C(=O)NHNH$_2$, —NHC(=O)$R^6$, —C(=NH)$R^6$, $R^7$.

An interesting group of compounds are those compounds of formula (I) wherein -$a^1$=$a^2$-$a^3$=$a^4$- represents a bivalent radical of formula —CH=CH—CH=CH— (a-1).

Also an interesting group of compounds are those compounds of formula (I) having the formula

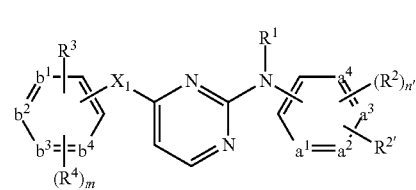

the N-oxides, the pharmaceutically acceptable addition salts, the quaternary amines or the stereochemically isomeric forms thereof, wherein
-$a^1$=$a^2$-$a^3$=$a^4$-, -$b^1$=$b^2$-$b^3$=$b^4$-, $R^1$, $R^2$, $R^3$, $R^4$, m and $X_1$ are as defined hereinabove; n' is 0, 1, 2 or 3 and in case -$a^1$=$a^2$-$a^3$=$a^4$- is (a-1), then n' may also be 4;
$R^{2'}$ is halo, $C_{1-6}$alkyl, trihalomethyl, cyano, aminocarbonyl, $C_{1-6}$alkyl substituted with cyano or aminocarbonyl;
provided that $R^{2'}$ is placed at the para position in respect of the $NR^1$ moiety.

Another interesting group of compounds are those compounds of formula (I) having the formula

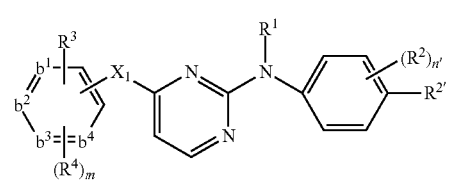

the N-oxides, the pharmaceutically acceptable addition salts, the quaternary amines or the stereochemically isomeric forms thereof, wherein
-$b^1$=$b^2$-$b^3$=$b^4$-, $R^1$, $R^2$, $R^3$, $R^4$, m and $X_1$ are as defined hereinabove;
n' is 0, 1, 2, 3 or 4;
$R^{2'}$ is halo, $C_{1-6}$alkyl, trihalomethyl, cyano, aminocarbonyl, $C_{1-6}$alkyl substituted with cyano or aminocarbonyl.

Yet a further interesting group of compounds are those compounds of formula (I) having the formula

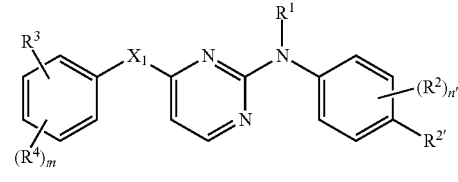

the N-oxides, the pharmaceutically acceptable addition salts, the quaternary amines or the stereochemically isomeric forms thereof, wherein
$R^1$, $R^2$, $R^3$, $R^4$ and $X_1$ are as defined hereinabove;
n' is 0, 1, 2, 3 or 4;
$R^{2'}$ is halo, $C_{1-6}$alkyl, trihalomethyl, cyano, aminocarbonyl, $C_{1-6}$alkyl substituted with cyano or aminocarbonyl.

Also particular compounds are those compounds of formula (I), (I'), (I") or (I''') wherein one or wherever possible more of the following conditions apply:
a) m is 1, 2 or 3, in particular 2 or 3, more in particular 2, even more in particular m is 2 and said two $R^4$ substituents are placed in position 2 and 6 (ortho position) in respect of the $X_1$ moiety;

b) m is 1, 2 or 3 and $R^3$ is placed in position 4 (para position) in respect of the $X_1$ moiety;

c) $X_1$ is —$NR^5$—, —NH—NH—, —N═N—, —O—, —C(═O)—, $C_{1-4}$alkanediyl, —CHOH—, —S(═O)$_p$—, —$X_2$—$C_{1-4}$alkanediyl- or —$C_{1-4}$alkanediyl-$X_2$—;

d) where applicable n' is 0;

e) where applicable n is 1 and said $R^2$ substituent is placed in position 4 (para position) in respect of the $NR^1$-linker;

f) $R^2$ is hydroxy, halo, $C_{1-6}$alkyl optionally substituted with cyano or —C(═O)$R^6$, $C_{3-7}$cycloalkyl, $C_{2-6}$alkenyl optionally substituted with one or more halogen atoms or cyano, $C_{2-6}$alkynyl optionally substituted with one or more halogen atoms or cyano, $C_{1-6}$alkyloxycarbonyl, carboxyl, cyano, nitro, amino, mono- or di($C_{1-6}$alkyl)amino, polyhalomethyl, polyhalomethylthio, —S(═O)$_p R^6$, —NH—S(═O)$_p R^6$, —NHC(═O)H, —C(═O)NHNH$_2$, —NHC(═O)$R^6$, —C(═NH)$R^6$ or a radical of formula

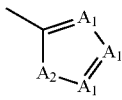

(c)

wherein each $A_1$ independently is N, CH or $CR^6$; and $A_2$ is NH, O, S or $NR^6$;

g) $R^{2'}$ is halo, $C_{1-6}$alkyl, trihalomethyl, cyano, $C_{1-6}$alkyl substituted with cyano or aminocarbonyl;

h) $R^2$ is cyano, aminocarbonyl or $C_{1-6}$alkyl substituted with cyano or aminocarbonyl, in particular cyano;

i) $R^{2'}$ is cyano, aminocarbonyl or $C_{1-6}$alkyl substituted with cyano or aminocarbonyl, in particular cyano.

A preferred embodiment encompasses those compounds of formula (I), (I'), (I'') or (I''') wherein $R^3$ is $NHR^{13}$; $NR^{13}R^{14}$; —C(═O)—$NHR^{13}$; —C(═O)—$NR^{13}R^{14}$; —C(═O)—$R^{15}$; —CH═N—NH—C(═O)—$R^{16}$; $C_{2-6}$alkyl substituted with cyano or aminocarbonyl; $C_{1-6}$alkyl substituted with $NR^9R^{10}$, —C(═O)—$NR^{9a}R^{10}$, —C(═O)—$C_{1-6}$alkyl or $R^7$; $C_{1-6}$alkyl substituted with two or more substituents each independently selected from cyano, $NR^9R^{10}$, —C(═O)—$NR^9R^{10}$, —C(═O)—$C_{1-6}$alkyl or $R^7$; $C_{1-6}$alkyl substituted with one or more substituents each independently selected from cyano, $NR^9R^{10}$, —C(═O)—$NR^9R^{10}$, —C(═O)—$C_{1-6}$alkyl or $R^7$ and wherein 2 hydrogen atoms bound at the same carbon atom are replaced by $C_{1-4}$alkanediyl; $C_{1-6}$alkyl substituted with hydroxy and a second substituent selected from cyano, $NR^9R^{10}$, —C(═O)—$NR^9R^{10}$, —C(═O)—$C_{1-6}$alkyl or $R^7$; $C_{1-6}$alkyloxy$C_{1-6}$alkyl optionally substituted with one or more substituents each independently selected from cyano, $NR^9R^{10}$, —C(═O)—$NR^9R^{10}$, —C(═O)—$C_{1-6}$alkyl or $R^7$; $C_{2-6}$alkenyl substituted with one or more substituents each independently selected from halo, cyano, $NR^9R^{10}$, —C(═O)—$NR^9R^{10}$, —C(═O)—$C_{1-6}$alkyl or $R^7$; $C_{2-6}$alkynyl substituted with one or more substituents each independently selected from halo, cyano, $NR^9R^{10}$, —C(═O)—$NR^9R^{10}$, —C(═O)—$C_{1-6}$alkyl or $R^7$; —C(═N—O—$R^8$)—$C_{1-4}$alkyl; $R^7$ or —$X_3$—$R^7$; with $R^{9a}$ representing hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl, —CH(═$NR^{11}$) or $R^7$, wherein each of the aforementioned $C_{1-6}$alkyl groups in the definition of $R^{9a}$ may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalomethyl, polyhalomethyloxy, polyhalomethylthio, —S(═O)$_p R^6$, —NH—S(═O)$_p R^6$, —C(═O)$R^6$, —NHC(═O)H, —C(═O)NHNH$_2$, —NHC(═O)$R^6$, —C(═NH) $R^6$, $R^7$; $R^{9a}$ may also be taken together with $R^{10}$ to form a bivalent or trivalent radical of formula (d-1), (d-2), (d-3), (d-4), (d-5), (d-6) or (d-7) as defined hereinabove.

A further interesting group of compounds are those compounds of formula (I), (I'), (I'') or (I''') wherein $R^3$ is $NHR^{13}$; $NR^{13}R^{14}$; —C(═O)—$NHR^{13}$; —C(═O)—$NR^{13}R^{14}$; —C(═O)—$R^{15}$; —CH═N—NH—C(═O)—$R^{16}$; $C_{1-6}$alkyl substituted with $NR^9R^{10}$, —C(═O)—$NR^{9a}R^{10}$, —C(═O)—$C_{1-6}$alkyl or $R^7$; $C_{1-6}$alkyl substituted with two or more substituents each independently selected from cyano, $NR^9R^{10}$, —C(═O)—$NR^9R^{10}$, —C(═O)—$C_{1-6}$alkyl or $R^7$; $C_{1-6}$alkyl substituted with one or more substituents each independently selected from cyano, $NR^9R^{10}$, —C(═O)—$NR^9R^{10}$, —C(═O)—$C_{1-6}$alkyl or $R^7$ and wherein 2 hydrogen atoms bound at the same carbon atom are replaced by $C_{1-4}$alkanediyl; $C_{1-6}$alkyl substituted with hydroxy and a second substituent selected from cyano, $NR^9R^{10}$, —C(═O)—$NR^9R^{10}$, —C(═O)—$C_{1-6}$alkyl or $R^7$; $C_{1-6}$alkyloxy$C_{1-6}$alkyl optionally substituted with one or more substituents each independently selected from cyano, $NR^9R^{10}$, —C(═O)—$NR^9R^{10}$, —C(═O)—$C_{1-6}$alkyl or $R^7$; $C_{2-6}$alkenyl substituted with one or more substituents each independently selected from halo, cyano, $NR^9R^{10}$, —C(═O)—$NR^9R^{10}$, —C(═O)—$C_{1-6}$alkyl or $R^7$; $C_{2-6}$alkynyl substituted with one or more substituents each independently selected from halo, cyano, $NR^9R^{10}$, —C(═O)—$NR^9R^{10}$, —C(═O)—$C_{1-6}$alkyl or $R^7$; —C(═N—O—R)—$C_{1-4}$alkyl; $R^7$ or —$X_3$—$R^7$; with $R^{9a}$ representing hydroxy; $C_{1-6}$alkyl; $C_{1-6}$alkyloxy; $C_{1-6}$alkylcarbonyl; $C_{1-6}$alkyloxycarbonyl; amino; mono- or di($C_{1-6}$alkyl)amino; mono- or di($C_{1-6}$alkyl)aminocarbonyl, —CH(═$NR^{11}$) or $R^7$, wherein each of the aforementioned $C_{1-6}$alkyl groups in the definition of $R^{9a}$ may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalomethyl, polyhalomethyloxy, polyhalomethylthio, —S(═O)$_p R^6$, —NH—S(═O)$_p R^6$, —C(═O)$R^6$, —NHC(═O)H, —C(═O)NHNH$_2$, —NHC(═O)$R^6$, —C(═NH) $R^6$, $R^7$; $R^{9a}$ may also be taken together with $R^{10}$ to form a bivalent or trivalent radical of formula (d-1), (d-2), (d-3), (d-4), (d-5), (d-6) or (d-7) as defined hereinabove.

Also an interesting group of compounds are those compounds of formula (I), (I'), (I'') or (I''') wherein $R^3$ is —CH═N—NH—C(═O)—$R^{16}$; $C_{1-6}$alkyl substituted with $NR^9R^{10}$, —C(═O)—$NR^{9a}R^{10}$, —C(═O)—$C_{1-6}$alkyl or $R^7$; $C_{1-6}$alkyl substituted with two or more substituents each independently selected from cyano, $NR^9R^{10}$, —C(═O)—$NR^9R^{10}$, —C(═O)—$C_{1-6}$alkyl or $R^7$; $C_{1-6}$alkyl substituted with one or more substituents each independently selected from cyano, $NR^9R^{10}$, —C(═O)—$NR^9R^{10}$, —C(═O)—$C_{1-6}$alkyl or $R^7$ and wherein 2 hydrogen atoms bound at the same carbon atom are replaced by $C_{1-4}$alkanediyl; $C_{1-6}$alkyl substituted with hydroxy and a second substituent selected from cyano, $NR^9R^{10}$, —C(═O)—$NR^9R^{10}$, —C(═O)—$C_{1-6}$alkyl or $R^7$; $C_{1-6}$alkyloxy$C_{1-6}$alkyl optionally substituted with one or more substituents each independently selected from cyano, $NR^9R^{10}$, —C(═O)—$NR^9R^{10}$, —C(═O)—$C_{1-6}$alkyl or $R^7$; $C_{2-6}$alkenyl substituted with one or more substituents each independently selected from halo, cyano, $NR^9R^{10}$, —C(═O)—$NR^9R^{10}$, —C(═O)—$C_{1-6}$alkyl or $R^7$; $C_{2-6}$alkynyl substituted with one or more substituents each independently selected from halo, cyano, $NR^9R^{10}$, —C(=O)—$NR^9R^{10}$, —C(=O)—$C_{1-6}$alkyl or $R^7$; —C(=N—O—$R^8$)—$C_{1-4}$alkyl; $R^7$ or —$X_3$—$R^7$; with $R^{9a}$ as defined hereinabove.

Another interesting group of compounds are those compounds of formula (I), (I'), (I") or (I'") wherein $R^3$ is $NHR^{13}$, $NR^{13}R^{14}$, —C(=O)—$R^{15}$, $C_{1-6}$alkyl substituted with one or more substituents each independently selected from cyano, $NR^9R^{10}$, —C(=O)—$NR^9R^{10}$, —C(=O)—$C_{1-6}$alkyl or $R^7$; $C_{1-6}$alkyl substituted with one or more substituents each independently selected from cyano, $NR^9R^{10}$, —C(=O)—$NR^9R^{10}$, —C(=O)—$C_{1-6}$alkyl or $R^7$ and wherein 2 hydrogen atoms bound at the same carbon atom are replaced by $C_{1-4}$alkanediyl; $C_{1-6}$alkyl substituted with hydroxy and a second substituent selected from cyano, $NR^9R^{10}$, —C(=O)—$NR^9R^{10}$, —C(=O)—$C_{1-6}$alkyl or $R^7$; $C_{1-6}$alkyloxy$C_{1-6}$alkyl optionally substituted with one or more substituents each independently selected from cyano, $NR^9R^{10}$, —C(=O)—$NR^9R^{10}$, —C(=O)—$C_{1-6}$alkyl or $R^7$; $C_{2-6}$alkenyl substituted with one or more substituents each independently selected from halo, cyano, $NR^9R^{10}$, —C(=O)—$NR^9R^{10}$, —C(=O)—$C_{1-6}$alkyl or $R^7$; $C_{2-6}$alkynyl substituted with one or more substituents each independently selected from halo, cyano, $NR^9R^{10}$, —C(=O)—$NR^9R^{10}$, —C(=O)—$C_{1-6}$alkyl or $R^7$; —C(=N—O—$R^8$)—$C_{1-4}$alkyl; $R^7$ or —$X_3$—$R^7$.

Also interesting are those compounds of formula (I), (I'), (I") or (I'") wherein $R^3$ is $C_{1-6}$alkyl substituted with $NR^9R^{10}$, —C(=O)—$NR^{9a}R^{10}$, —C(=O)—$C_{1-6}$alkyl or $R^7$; $C_{1-6}$alkyl substituted with two or more substituents each independently selected from cyano, $NR^9R^{10}$, —C(=O)—$NR^9R^{10}$, —C(=O)—$C_{1-6}$alkyl or $R^7$; $C_{1-6}$alkyl substituted with one or more substituents each independently selected from cyano, $NR^9R^{10}$, —C(=O)—$NR^9R^{10}$, —C(=O)—$C_{1-6}$alkyl or $R^7$ and wherein 2 hydrogen atoms bound at the same carbon atom are replaced by $C_{1-4}$alkanediyl; $C_{1-6}$alkyl substituted with hydroxy and a second substituent selected from cyano, $NR^9R^{10}$, —C(=O)—$NR^9R^{10}$, —C(=O)—$C_{1-6}$ alkyl or $R^7$; $C_{1-6}$alkyloxy$C_{1-6}$alkyl optionally substituted with one or more substituents each independently selected from cyano, $NR^9R^{10}$, —C(=O)—$NR^9R^{10}$, —C(=O)—$C_{1-6}$alkyl or $R^7$; $C_{2-6}$alkenyl substituted with one or more substituents each independently selected from halo, cyano, $NR^9R^{10}$, —C(=O)—$NR^9R^{10}$, —C(=O)—$C_{1-6}$ alkyl or $R^7$; $C_{2-6}$alkynyl substituted with one or more substituents each independently selected from halo, cyano, $NR^9R^{10}$, —C(=O)—$NR^9R^{10}$, —C(=O)—$C_{1-6}$alkyl or $R^7$; —C(=N—O—R)—$C_{1-4}$alkyl; $R^7$ or —$X_3$—$R^7$; with $R^{9a}$ as defined hereinabove.

Also interesting are those compounds of formula (I), (I'), (I") or (I'") wherein $R^3$ is $C_{1-6}$alkyl substituted with one or more substituents each independently selected from cyano, $NR^9R^{10}$ or $R^7$; $C_{2-6}$alkenyl substituted with one or more substituents each independently selected from cyano, $NR^9R^{10}$ or $R^7$; $C_{1-6}$alkyloxy$C_{1-6}$alkyl substituted with cyano; $C_{1-6}$alkyl substituted with hydroxy and a second substituent selected from cyano or $R^7$; —C(=N—O—$R^8$)—$C_{1-4}$alkyl; $R^7$ or —$X_3$—$R^7$.

Another interesting group of compounds are those compounds of formula (I), (I'), (I") or (I'") wherein $R^3$ is $R^7$.

Still another interesting group of compounds are those compounds of formula (I), (I'), (I") or (I'") wherein $R^3$ is $C_{1-6}$alkyl substituted with cyano, in particular $C_{2-6}$alkyl substituted with cyano, more in particular ethyl or propyl substituted with cyano; or $C_{2-6}$alkenyl substituted with cyano. Preferred is $C_{2-6}$alkenyl substituted with cyano.

Also an interesting group of compounds are those compounds of formula (I), (I'), (I") or (I'") wherein $R^3$ is $C_{1-6}$alkyl substituted with cyano and $R^7$, or $C_{2-6}$alkenyl substituted with cyano and $R^7$.

A further interesting group of compounds are those compounds of formula (I), (I'), (I") or (I'") wherein $R^3$ is $C_{1-6}$alkyl substituted with $R^7$.

Still a further interesting group of compounds are those compounds of formula (I), (I'), (I") or (I'") wherein $R^3$ is —C(=N—O—$R^8$)—$C_{1-4}$alkyl.

Also an interesting group of compounds are those compounds of formula (I), (I'), (I") or (I'") wherein $R^3$ is $C_{1-6}$alkyl substituted with hydroxy and a second substituent selected from cyano or R.

Also an interesting group of compounds are those compounds of formula (I), (I'), (I") or (I'") wherein $R^2$ or $R^{2'}$ is cyano or aminocarbonyl and $R^1$ is hydrogen.

Another interesting group of compounds are those compounds of formula (I), (I'), (I") or (I'") wherein m is 2 or 3 and $X_1$ is —$NR^5$—, —O—, —C(=O)—, —$CH_2$—, —CHOH—, —S—, —S(=O)$_p$—, in particular wherein $X_1$ is —$NR^5$—, or —O—.

Also an interesting group of compounds are those compounds of formula (I), (I'), (I") or (I'") wherein one or more, preferably all of the following restrictions apply:
a) n is at least 1, in particular 1; or n' is 0;
b) $R^2$ or $R^{2'}$ is cyano;
c) m is 1, 2 or 3;
d) $R^4$ is $C_{1-6}$alkyl, especially methyl; nitro; amino; halo; $C_{1-6}$alkyloxy or $R^7$;
e) $R^3$ is $R^7$, $NR^{13}R^{14}$, —C(=O)$R^{15}$, —CH=N—NH—C(=O)$R^{16}$, —C(=O)$NHR^{13}$, —C(=O)$NR^{13}R^{14}$, —C(=N—OR)—$C_{1-4}$alkyl, $C_{1-6}$alkyl substituted with cyano, $C_{1-6}$alkyl substituted twice with cyano, $C_{1-6}$alkyl substituted with $NR^9R^{10}$, $C_{1-6}$alkyl substituted with hydroxy and cyano, $C_{1-6}$alkyl substituted with hydroxy and $R^7$, $C_{1-6}$alkyloxy $C_{1-6}$alkyl, $C_{1-6}$alkyloxy $C_{1-6}$alkyl substituted with cyano, $C_{2-6}$alkenyl substituted with $R^7$, $C_{2-6}$alkenyl substituted with cyano, $C_{2-6}$alkenyl substituted twice with cyano, $C_{2-6}$alkenyl substituted with cyano and $R^7$, $C_{2-6}$alkenyl substituted with cyano and —C(=O)—$C_{1-6}$alkyl, $C_{2-6}$alkenyl substituted with cyano and halo, $C_{2-6}$alkenyl substituted with —C(=O)—$NR^9R^{10}$, $C_{2-6}$alkenyl substituted with halo, $C_{2-6}$alkenyl substituted twice with halo or $C_{2-6}$alkenyl substituted with $NR^9R^{10}$;
f) $X_3$ is —C(=O)—, —$CH_2$—C(=O)—, or —C(=N—$OR^8$)—$C_{1-4}$alkanediyl-;
g) $X_1$ is NH or O;
h) $R^1$ is hydrogen or $C_{1-4}$alkyl.

Preferred compounds of formula (I), (I'), (I") or (I'") are compounds 1, 25, 84, 133, 152, 179, 233, 239, 247, 248 (see Tables 3, 4 and 5), their N-oxides, pharmaceutically acceptable addition salts, quaternary amines and stereochemically isomeric forms thereof.

In general, compounds of formula (I) can be prepared by reacting an intermediate of formula (II) wherein $W_1$ is a suitable leaving group such as, for example, halo, triflate, tosylate, methylsulfonyl and the like, with an intermediate of formula (III). This reaction can be performed at elevated temperature

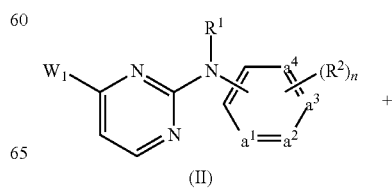

(II)

-continued

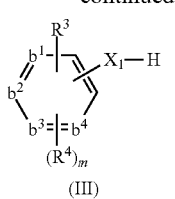

(III)

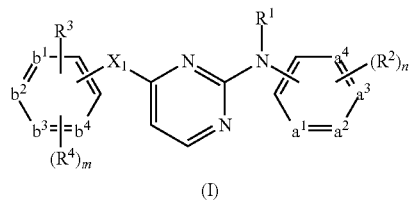

(I)

Alternatively, the above reaction can be performed in the presence of a suitable solvent. Suitable solvents are for example acetonitrile, an alcohol, such as for example ethanol, 2-propanol, 2-propanol-HCl; N,N-dimethylformamide; N,N-dimethylacetamide, 1-methyl-2-pyrrolidinone; 1,4-dioxane, propyleneglycol monomethylether. Preferably the solvent is 2-propanol, 6 N HCl in 2-propanol or acetonitrile, especially acetonitrile. Optionally, sodium hydride may be present.

In this and the following preparations, the reaction products may be isolated from the reaction medium and, if necessary, further purified according to methodologies generally known in the art such as, for example, extraction, crystallization, distillation, trituration and chromatography.

Compounds of formula (I) wherein $R^3$ is $R^7$ representing a monocyclic, bicyclic or tricyclic aromatic ring system, said $R^3$ being represented by $R^{7'}$ and said compounds being represented by formula (I-a), can be prepared by reacting an intermediate of formula (IV) wherein $W_2$ represents a suitable leaving group such as, for example, halo, hydroxy, triflate, tosylate, thiomethyl, methylsulfonyl, trifluoromethylsulfonyl and the like, with an intermediate of formula (V) wherein $R^a$ represents a boronate or a tri($C_{1-4}$alkyl)stannane, such as tributylstannane, in the presence of a suitable catalyst, such as for example palladium tetrakis(triphenylphosphine), a suitable salt, such as for example disodium carbonate, dipotassium carbonate, and $Cs_2CO_3$, and a suitable solvent, such as for example dioxane, dimethyl ether, toluene or an alcohol/water mixture, e.g. MeOH/$H_2O$. $R^a$ may also represent halo, such as for example bromo, in which case the reaction is performed in the presence of 4,4,4',4',5,5,5',5'-octamethyl-2,2'-bi-1,3,2-dioxaborolane.

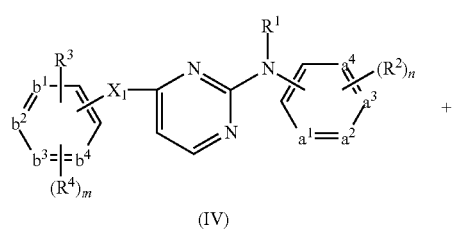

(IV)

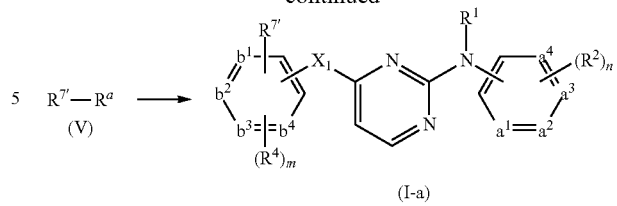

(I-a)

Compounds of formula (I) wherein $R^3$ is $R^7$ representing a monocyclic, bicyclic or tricyclic saturated ring system, said $R^3$ being represented by $R^{7''}$ and said compounds being represented by formula (I-b), can be prepared by reacting an intermediate of formula (IV) with an intermediate of formula (VI)

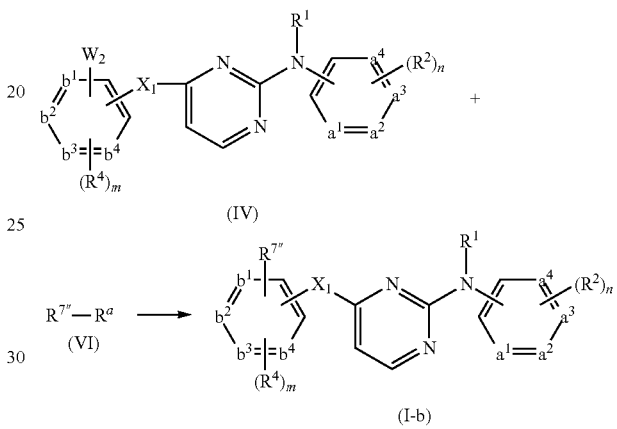

Compounds of formula (I) wherein $R^3$ represents $C_{1-6}$alkyl substituted with cyano, said $R^3$ being represented by $C_{1-6}$alkyl-CN and said compounds being represented by formula (I-c), can be prepared by reacting an intermediate of formula (VII) wherein $W_3$ represents a suitable leaving group, such as for example, halo, e.g. chloro, with a suitable cyanide salt, such as for example sodium cyanide or potassium cyanide, in the presence of a suitable solvent, such as for example N,N-dimethylformamide or dimethylsulfoxide.

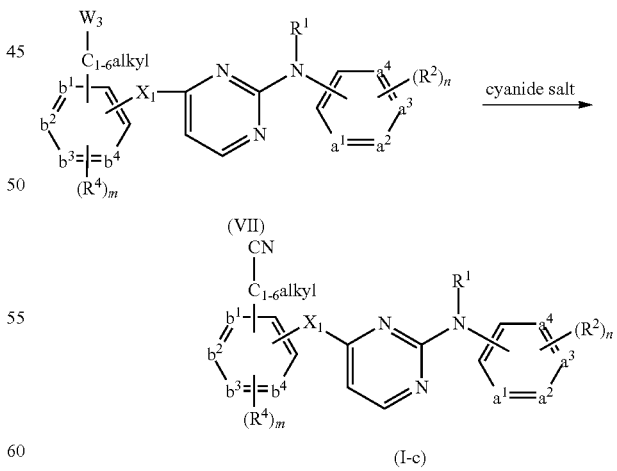

Compounds of formula (I) wherein $R^3$ represents $C_{1-6}$alkyl substituted with $R^7$; $NR^9R^{10}$ or $C_{1-6}$alkyloxy optionally substituted with CN, $R^7$ or $NR^9R^{10}$, said $R^3$ being represented by $C_{1-6}$alkyl-Q wherein Q represents $R^7$; $NR^9R^{10}$ or $C_{1-6}$alkyloxy optionally substituted with CN, $R^7$ or $NR^9R^{10}$, and said compounds being represented by formula (I-d), can be prepared by reacting an intermediate of formula (VII) with an intermediate of formula (VIII), optionally in the presence of a suitable salt, such as for example dipotassium carbonate, potassium cyanide, potassium iodide, and a suitable solvent, such as for example acetonitrile.

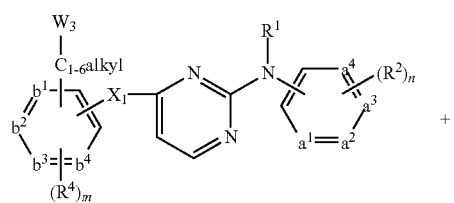

(VII)

Q—H
(VIII) →

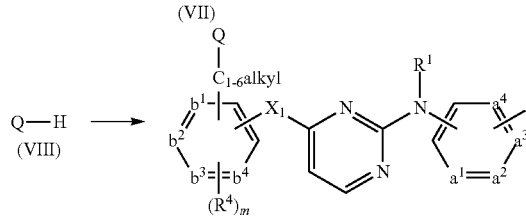

(I-d)

Compounds of formula (I) wherein $R^3$ represents —C(=N—O—R)—$C_{1-4}$alkyl, said compounds being represented by formula (I-e), can be prepared by reacting an intermediate of formula (IX) with an intermediate of formula (X) in the presence of a suitable solvent, such as an alcohol, e.g. ethanol.

(IX)

$R^8$—O—NH$_2$
(X)

(I-e)

Compounds of formula (I) wherein $R^3$ represents $CR^{c'}$=$CR^c$—CN wherein $R^c$ represents hydrogen or $C_{1-4}$alkyl and $R^{c'}$ represents hydrogen, $C_{1-4}$alkyl or $R^7$, provided that $CR^{c'}$=$CR^c$ is limited to $C_{2-6}$alkenyl, said compounds being represented by formula (I-f), can be prepared by reacting an intermediate of formula (XI) with a Wittig or Horner-Emmons reagent of formula (XII), wherein $R^b$— represents for example (Phenyl)$_3$P$^+$—Cl$^-$ or (CH$_3$CH$_2$—O)$_2$P(=O)—, which can be considered as a suitable precursor of a phosphorus ylide, in the presence of a suitable salt, such as for example potassium tert.-butoxide, and a suitable solvent, such as for example tetrahydrofuran.

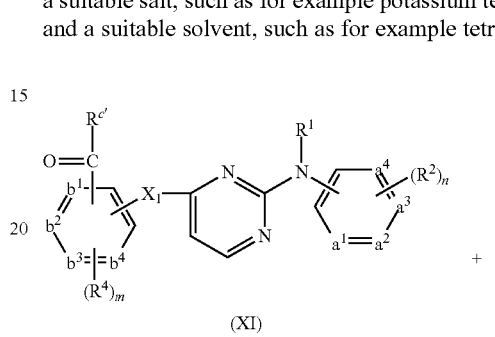

(XI)

$R^b$—CHR$^c$
|
CN
(XII)

(I-f)

Compounds of formula (I-f-1) and (I-f-2) as depicted below can be prepared by reacting an intermediate of formula (XXXIX) or an appropriate addition salt thereof, wherein $W_5$ represents a suitable leaving group, with acrylonitrile or acrylamide in the presence of a suitable palladium catalyst, a suitable base and a suitable solvent.

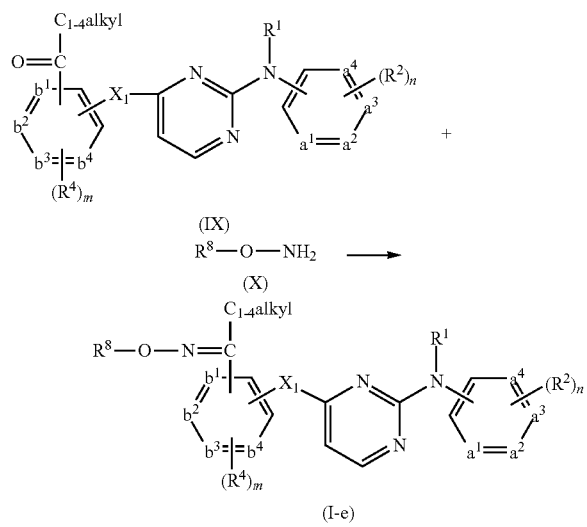

(XXXIX)

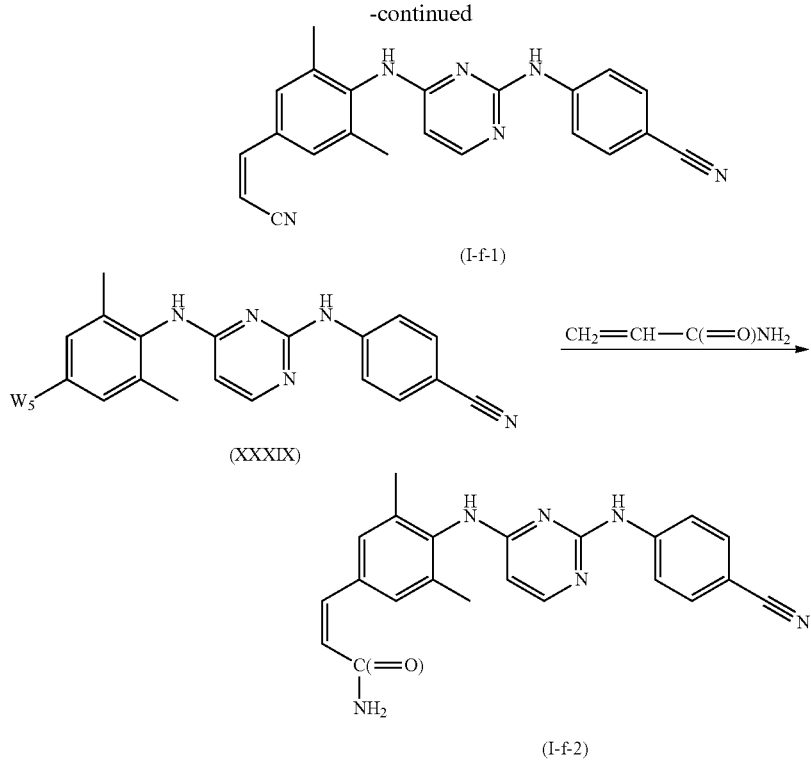

(I-f-1)

(XXXIX)

(I-f-2)

Suitable leaving groups in the above reaction are for example halo, triflate, tosylate, mesylate and the like. Preferably, $W_5$ is halo, more particularly iodo or bromo.

The palladium (Pd) catalyst may be a homogeneous Pd catalyst, such as for example $Pd(OAc)_2$, $PdCl_2$, $Pd(PPh_3)_4$, $Pd(PPh_3)_2Cl_2$, bis(dibenzylidene acetone) palladium, palladium thiomethylphenylglutaramide metallacycle and the like, or a heterogeneous Pd catalyst, such as for example palladium on charcoal, palladium on metal oxides, palladium on zeolites.

Preferably, the palladium catalyst is a heterogeneous Pd catalyst, more preferably palladium on charcoal (Pd/C). Pd/C is a recoverable catalyst, is stable and relatively inexpensive. It can be easily separated (filtration) from the reaction mixture thereby reducing the risk of Pd traces in the final product. The use of Pd/C also avoids the need for ligands, such as for example phosphine ligands, which are expensive, toxic and contaminants of the synthesized products.

Suitable bases in the above reaction are for example sodium acetate, potassium acetate, N,N-diethylethanamine, sodium hydrogencarbonate, sodium hydroxide and the like.

Suitable solvents in the above reaction are for example acetonitrile, N,N-dimethylacetamide, an ionic liquid e.g. [bmim]$PF_6$, N,N-dimethylformamide, water, tetrahydrofuran, dimethylsulphoxide, 1-methyl-2-pyrrolidinone and the like.

Compounds of formula (I) wherein $R^3$ represents $CR^c$=$CR^{c''}$—CN with $R^c$ being as defined hereinabove and $R^{c''}$ representing $NR^9R^{10}$, —C(=O)—$NR^9R^{10}$, —C(=O)—$C_{1-6}$alkyl or $R^7$, said compounds being represented by formula (I-g), can be prepared by reacting an intermediate of formula (XI-a) with an intermediate of formula (XIII) in the presence of a suitable solvent, such as for example an alcohol and an alcoholate, e.g. methanol and sodium ethanolate.

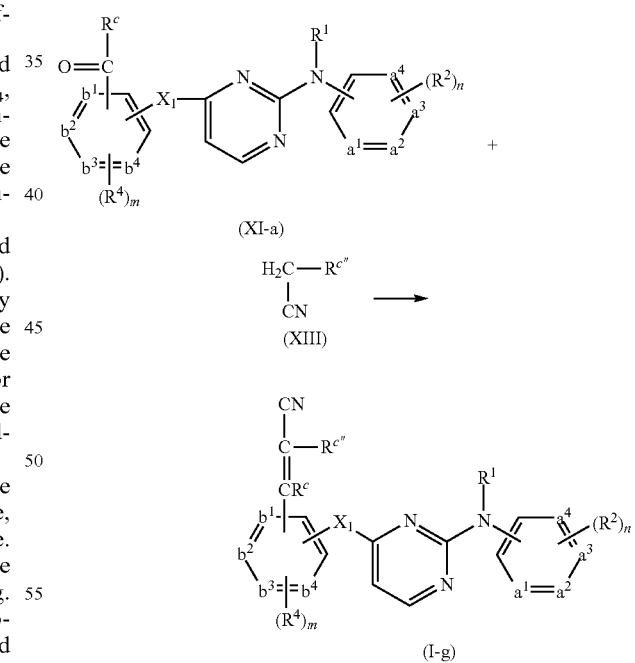

Compounds of formula (I) wherein $R^3$ represents CH=C(CN)—$CH_2$—CN, said compounds being represented by formula (I-h), can be prepared by reacting an intermediate of formula (XI-b) with 2-butenedinitrile in the presence of tributylphosphine and a suitable solvent, such as for example tetrahydrofuran.

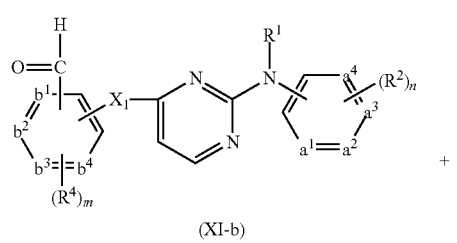

(XI-b)

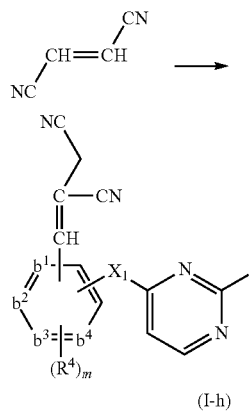

(I-h)

Compounds of formula (I) wherein $R^3$ represents CH═C(CN)$_2$, said compounds being represented by formula (I-h'), can be prepared by reacting an intermediate of formula (XI-b) with propanedinitrile in the presence of a suitable base, such as for example piperidine, and a suitable solvent, such as for example an alcohol, e.g. ethanol and the like.

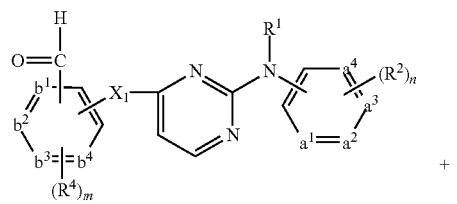

(XI-b)

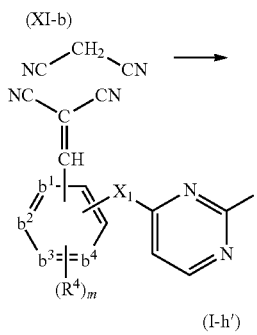

(I-h')

Compounds of formula (I) wherein $R^3$ represents —CHOH—CH$_2$—CN, said compounds being represented by formula (I-i), can be prepared by reacting an intermediate of formula (XI-b) with CH$_3$—CN in the presence of a suitable proton-abstracting agent, such as for example butyl lithium, in the presence of a suitable substrate for the proton-abstracting agent, for example N-(1-methylethyl)-2-propanamine, and in the presence of a suitable solvent, such as for example tetrahydrofuran.

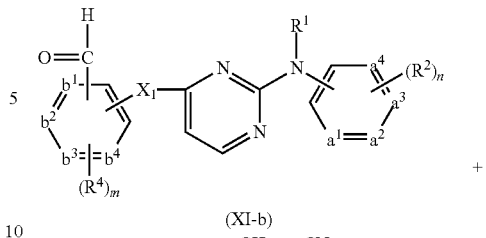

(XI-b)

CH$_3$—CN ⟶

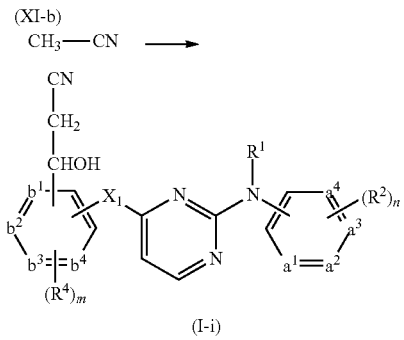

(I-i)

Compounds of formula (I) wherein $R^3$ represents CR$^{c'}$═CR$^c$-halo wherein $R^c$ represents hydrogen or C$_{1-4}$alkyl and $R^{c'}$ represents hydrogen, C$_{1-4}$alkyl or $R^7$, provided that CR$^{c'}$═CR$^c$ is limited to C$_{2-6}$alkenyl, said compounds being represented by formula (I-j), can be prepared by reacting an intermediate of formula (XI) with a Wittig or Horner-Emmons reagent of formula (XII'), wherein $R^b$— represents for example (Phenyl)$_3$P$^+$—Cl$^-$ or (CH$_3$CH$_2$—O)$_2$P(═O)—, which can be considered as a suitable precursor of a phosphorus ylide, in the presence of nBuLi, and a suitable solvent, such as for example tetrahydrofuran.

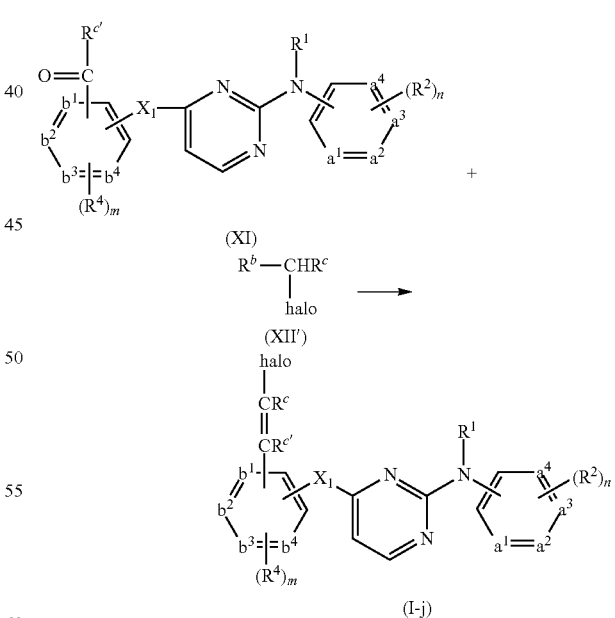

(I-j)

Compounds of formula (I) wherein $R^3$ represents CR$^c$═CR$^{c'''}$-halo with $R^c$ being as defined hereinabove and $R^{c'''}$ representing CN, NR$^9$R$^{10}$, —C(═O)—NR$^9$R$^{10}$, —C(═O)—C$_{1-6}$alkyl or $R^7$, said compounds being represented by formula (I-k), can be prepared by reacting an intermediate of formula (XI-a) with an intermediate of formula (XIII-a) in the presence of a Horner-Emmons reagent such as for example (CH₃CH₂—O)₂P(=O)—Cl, nBuLi, 1,1,1-trimethyl-N-(trimethylsilyl)-silanamine, and a suitable solvent, such as for example tetrahydrofuran.

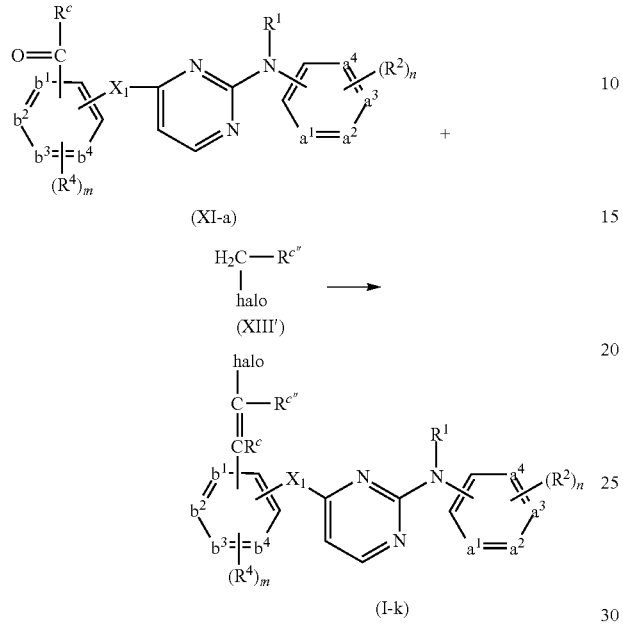

Compounds of formula (I) wherein R³ represents CH=C(Br)₂, said compounds being represented by formula (I-1), can be prepared by reacting an intermediate of formula (XVIII) with CBr₄, in the presence of a suitable catalyst salt, such as for example (CuCl)₂, and in the presence of a suitable base, such as for example NH₃, and a suitable solvent, such as for example dimethylsulfoxide.

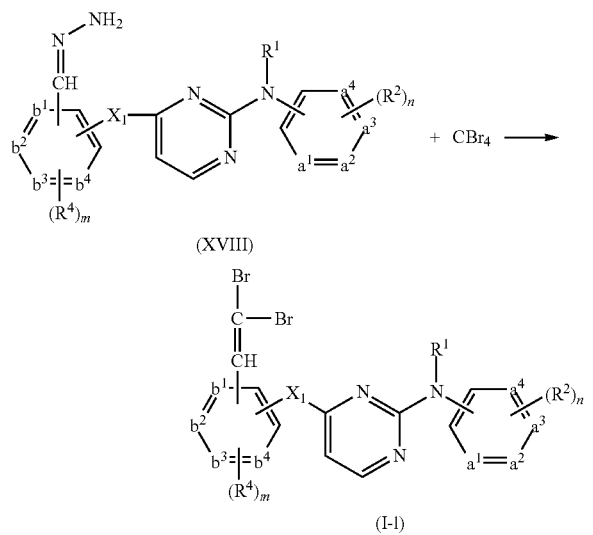

Compounds of formula (I-m) can be prepared by reacting an intermediate of formula (XIV) with Cl₂C=S in the presence of a suitable solvent, such as for example dioxane.

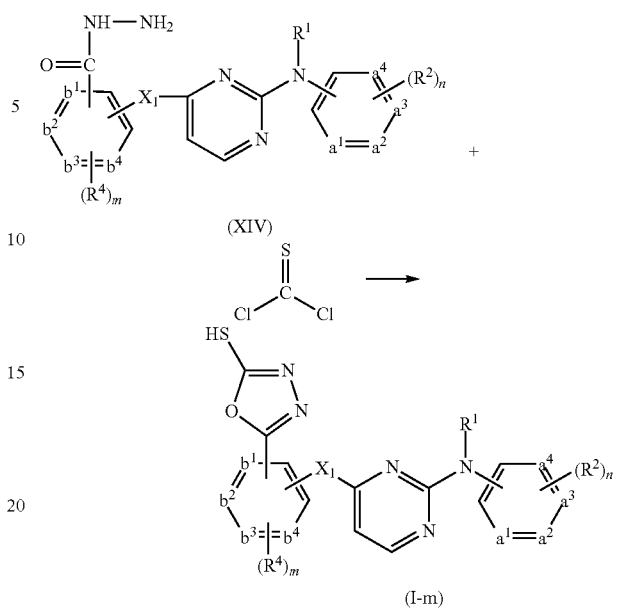

Compounds of formula (I-n) can be prepared by reacting an intermediate of formula (XV) with an intermediate of formula (XVI) in the presence of a suitable solvent, such as for example an alcohol or an alcoholate, e.g. ethanol or sodium methanolate.

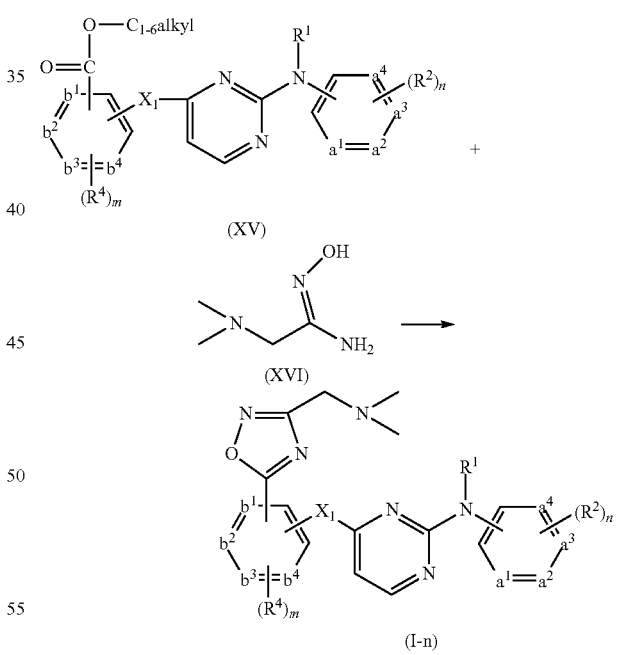

Compounds of formula (I) wherein R³ represents C₂₋₆alkenyl substituted with C(=O)NR⁹R¹⁰ and optionally further substituted with cyano, said compounds being represented by formula (I-o) wherein C₂₋₆alkenyl' represents C₂₋₆alkenyl optionally substituted with cyano, can be prepared by reacting an intermediate of formula (XXIX) with an intermediate of formula (XXX) in the presence of hydroxybenzotriazole and ethyldimethylaminopropyl carbodiimide and a suitable solvent, such as for example methylene chloride or tetrahydrofuran, and optionally in the presence of a suitable base, such as for example N,N-diethylethanamine, NH₄OH and the like.

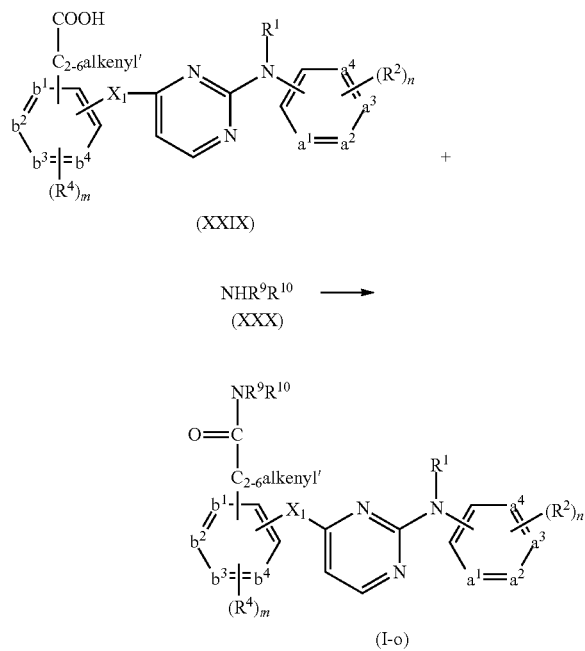

(XXIX)

NHR⁹R¹⁰
(XXX)

(I-o)

Compounds of formula (I) wherein $R^3$ represents —C(=O)NR¹³R¹⁴ or —C(=O)NHR¹³, said compounds being represented by formula (I-p-1) and (I-p-2) can be prepared by reacting an intermediate of formula (XXXI) with an intermediate of formula (XXXII-1) or (XXXII-2) in the presence of hydroxybenzotriazole and ethyldimethylaminopropyl carbodiimide and a suitable solvent, such as for example methylene chloride or tetrahydrofuran, and optionally in the presence of a suitable base, such as for example N,N-diethyl ethanamine.

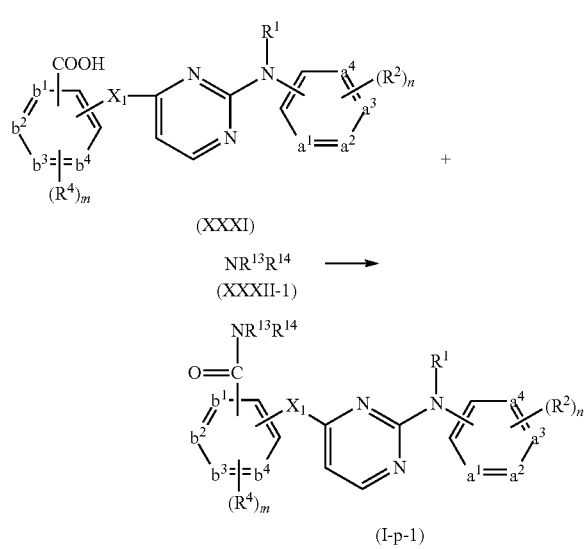

(XXXI)

NR¹³R¹⁴
(XXXII-1)

(I-p-1)

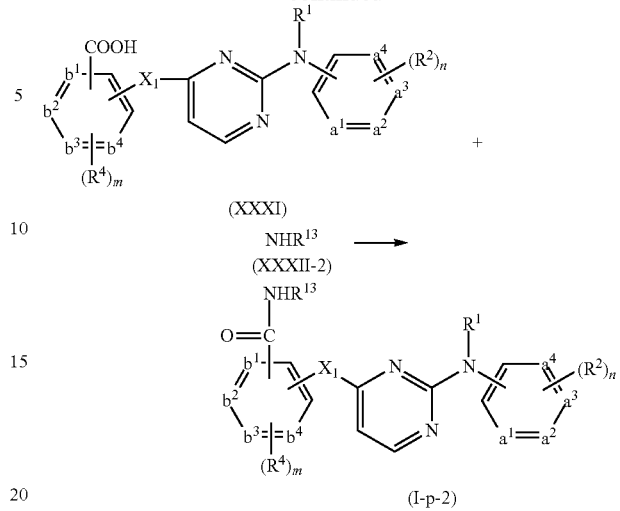

(XXXI)

NHR¹³
(XXXII-2)

(I-p-2)

Compounds of formula (I) wherein $R^3$ represents CH=N—NH—C(=O)—R¹⁶, said compounds being represented by formula (I-q), can be prepared by reacting an intermediate of formula (XI-b) with an intermediate of formula (XXXIII) in the presence of a suitable solvent, such as for example methylene chloride and an alcohol, e.g. methanol, ethanol and the like.

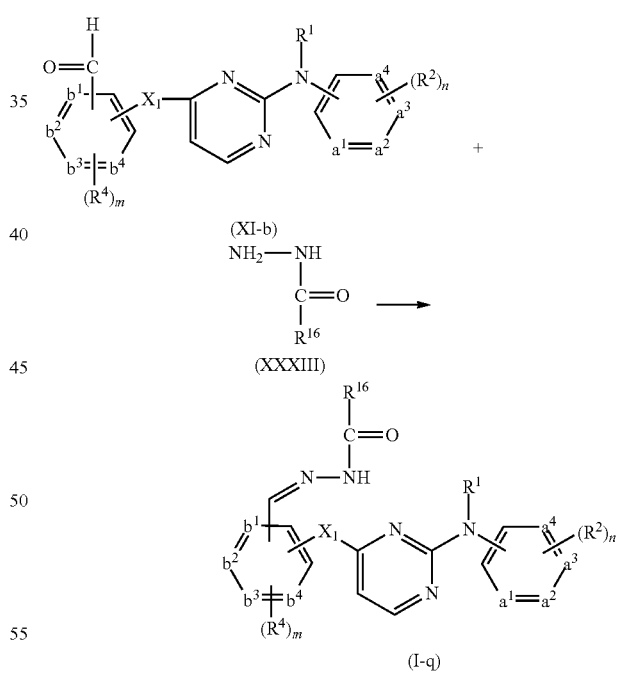

(XI-b)

(XXXIII)

(I-q)

Compounds of formula (I) wherein $R^3$ represents N(CH₃)₂, said compounds being represented by formula (I-r), can be prepared by reductive methylation of an intermediate of formula (XXXIV) with formaldehyde in the presence of a suitable catalyst, such as for example a suitable acid, i.e. acetic acid and the like, palladium on charcoal, Raney Nickel, and in the presence of a suitable reductive agent, such as for example sodium cyanoborohydride or H₂, and a suitable solvent, such as for example acetonitrile.

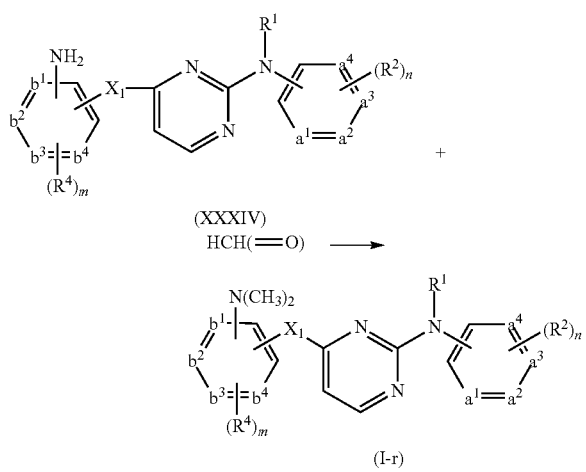

(XXXIV)
HCH(=O) →

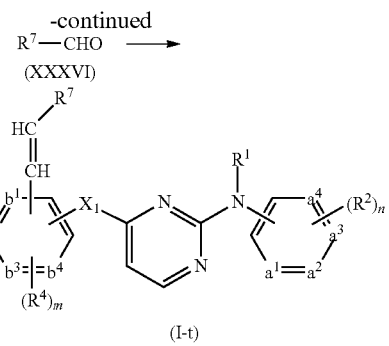

(I-t)

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^3$ represents pyrrolyl, said compounds being represented by formula (I-s), can be prepared by reacting an intermediate of formula (XXXIV) with 2,5-dimethoxytetrahydrofuran in the presence of a suitable acid, such as for example acetic acid.

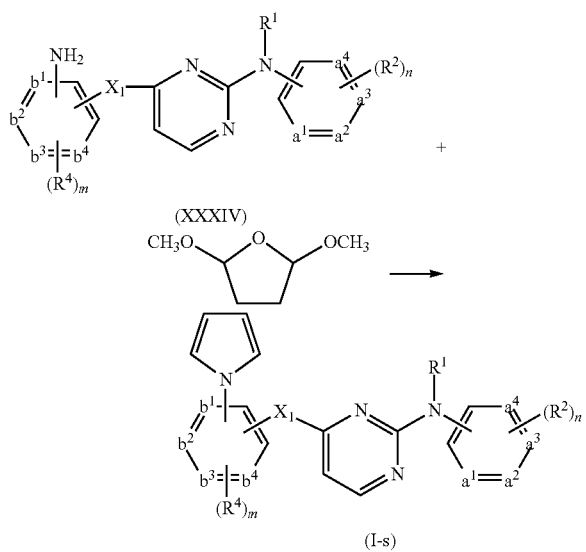

(I-s)

Compounds of formula (I) wherein $R^3$ represents CH=CH—$R^7$, said compounds being represented by formula (I-t), can be prepared by reacting an intermediate of formula (XXXV) (Ph indicates phenyl) with an intermediate of formula (XXXVI) in the presence of nBuLi and a suitable solvent, such as for example tetrahydrofuran.

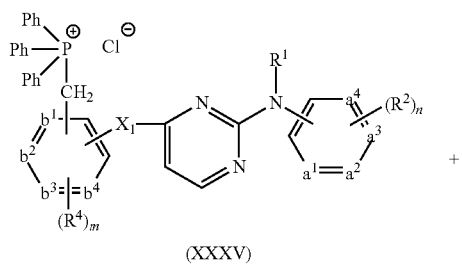

(XXXV)

For instance, a compound of formula (I) wherein $R^3$ comprises cyano, can be converted into a compound of formula (I) wherein $R^3$ comprises aminocarbonyl, by reaction with HCOOH, in the presence of a suitable acid, such as hydrochloric acid. A compound of formula (I) wherein $R^3$ comprises cyano, can also further be converted into a compound of formula (I) wherein $R^3$ comprises tetrazolyl, by reaction with sodium azide in the presence of ammonium chloride and N,N-dimethylacetamide.

Compounds of formula (I) wherein $R^3$ comprises aminocarbonyl, can be converted into a compound of formula (I) wherein $R^3$ comprises cyano, in the presence of a suitable dehydrating agent. The dehydration can be performed according to methodologies well-known to the person skilled in the art, such as the ones disclosed in "Comprehensive Organic Transformations. A guide to functional group preparations" by Richard C. Larock, John Wiley & Sons, Inc, 1999, p 1983-1985, which is incorporated herein as reference. Different suitable reagents are enumerated in said reference, such as for example $SOCl_2$, $HOSO_2NH_2$, $ClSO_2NCO$, $MeO_2CNSO_2NEt_3$, $PhSO_2Cl$, TsCl, $P_2O_5$, $(Ph_3PO_3SCF_3)O_3SCF_3$, polyphosphate ester, $(EtO)_2POP(OEt)_2$, $(EtO)_3PI_2$, 2-chloro-1,3,2-dioxaphospholane, 2,2,2-trichloro-2,2-dihydro-1,3,2-dioxaphospholane, $POCl_3$, $PPh_3$, $P(NCl_2)_3$, $P(NEt_2)_3$, $COCl_2$, $NaCl.AlCl_3$, $ClCOCOCl$, $ClCO_2Me$, $Cl_3CCOCl$, $(CF_3CO)_2O$, $Cl_3CN=CCl_2$, 2,4,6-trichloro-1,3,5-triazine, $NaCl.AlCl_3$, $HN(SiMe_2)_3$, $N(SiMe_2)_4$, $LiAlH_4$ and the like. All the reagents listed in said publication are incorporated herein as reference.

Compounds of formula (I) wherein $R^3$ comprises $C_{2-6}$alkenyl can be converted into a compound of formula (I)

wherein R³ comprises C$_{1-6}$alkyl by reduction in the presence of a suitable reducing agent, such as for example H$_2$, in the presence of a suitable catalyst, such as for example palladium on charcoal, and in the presence of a suitable solvent, such as for example an alcohol, e.g. methanol.

Compounds of formula (I) wherein R³ represents CH(OH)—R¹⁶, can be converted into a compound of formula (I) wherein R³ represents C(=O)—R¹⁶ by reaction with Jones's reagent in the presence of a suitable solvent, such as for example 2-propanone.

Compound of formula (I) wherein R³ represents C(=O)—CH$_2$—R$^{16a}$, wherein R$^{16a}$ represents cyano or aminocarbonyl, can be converted into a compound of formula (I) wherein R³ represents C(Cl)=CH—R$^{16a}$ by reaction with POCl$_3$.

Compounds of formula (I) wherein R³ represents a monocyclic, bicyclic or tricyclic saturated, partially saturated or aromatic carbocycle or a monocyclic, bicyclic or tricyclic saturated, partially saturated or aromatic heterocycle substituted with formyl can be converted into compounds of formula (I) wherein R³ represents a monocyclic, bicyclic or tricyclic saturated, partially saturated or aromatic carbocycle or a monocyclic, bicyclic or tricyclic saturated, partially saturated or aromatic heterocycle substituted with CH(=N—O—R⁸) by reaction with NH$_2$OR⁸ in the presence of a suitable base, such as for example sodium hydroxide and a suitable solvent, such as for example an alcohol, e.g. ethanol and the like. Compounds of formula (I) wherein R³ represents a monocyclic, bicyclic or tricyclic saturated, partially saturated or aromatic carbocycle or a monocyclic, bicyclic or tricyclic saturated, partially saturated or aromatic heterocycle substituted with CH(=N—O—R⁸) can be converted into a compound of formula (I) wherein R³ represents a monocyclic, bicyclic or tricyclic saturated, partially saturated or aromatic carbocycle or a monocyclic, bicyclic or tricyclic saturated, partially saturated or aromatic heterocycle substituted with CN by reaction with a carbodiimide in the presence of a suitable solvent, such as for example tetrahydrofuran.

Compounds of formula (I) wherein R⁴ represents nitro, can be converted into a compound of formula (I) wherein R⁴ is amino, in the presence of a suitable reducing agent, such as for example H$_2$, in the presence of a suitable catalyst, such as for example Raney Nickel, and in the presence of a suitable solvent, such as for example an alcohol, e.g. methanol.

Compounds of formula (I) wherein R¹ is hydrogen, can be converted into a compound of formula (I) wherein R¹ is C$_{1-6}$alkyl, by reaction with a suitable alkylating agent, such as for example iodo-C$_{1-6}$alkyl, in the presence of a suitable base, such as for example sodium hydride, and a suitable solvent, such as for example tetrahydrofuran.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures or some of the compounds of formula (I) or the described intermediates may be prepared according to the procedures described in WO 99/50250 and WO 00/27825.

Intermediates of formula (II) can be prepared by reacting an intermediate of formula (XVII) with a leaving group introducing agent of formula (XIX) wherein W$_1$ represents the leaving group and R represents the remaining of the leaving group introducing agent, such as for example POCl$_3$.

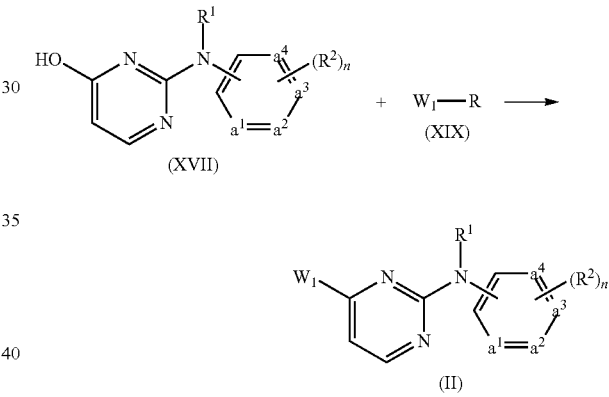

Intermediates of formula (III) wherein X$_1$ represents NH, said intermediates being represented by formula (III-a), can be prepared from an intermediate of formula (XX) in the presence of ZnCl$_2$ and in the presence of a suitable solvent, such as for example an alcohol, for example ethanol.

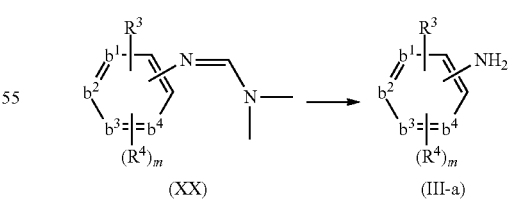

Intermediates of formula (III'-a) as depicted below can be prepared from an intermediate of formula (XX) wherein R³ represents C$_{2-6}$alkenyl substituted with CN, said intermediate being represented by formula (XX-a), in the presence of ZnCl$_2$ and in the presence of a suitable C$_{1-4}$alkyl-OH, such as for example ethanol.

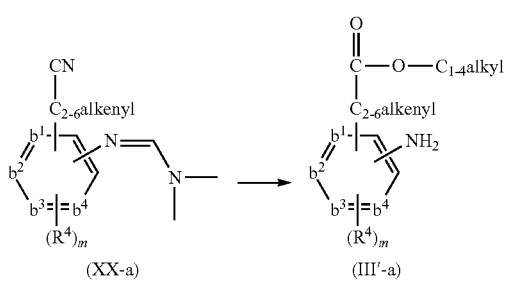

Intermediates of formula (III-b-1) and (III-b-2) as depicted below can be prepared by reacting an intermediate of formula (XLI) or an appropriate acid addition salt thereof, wherein $W_6$ represents a suitable leaving group, with acrylonitrile or acrylamide in the presence of a suitable palladium catalyst, a suitable base and a suitable solvent.

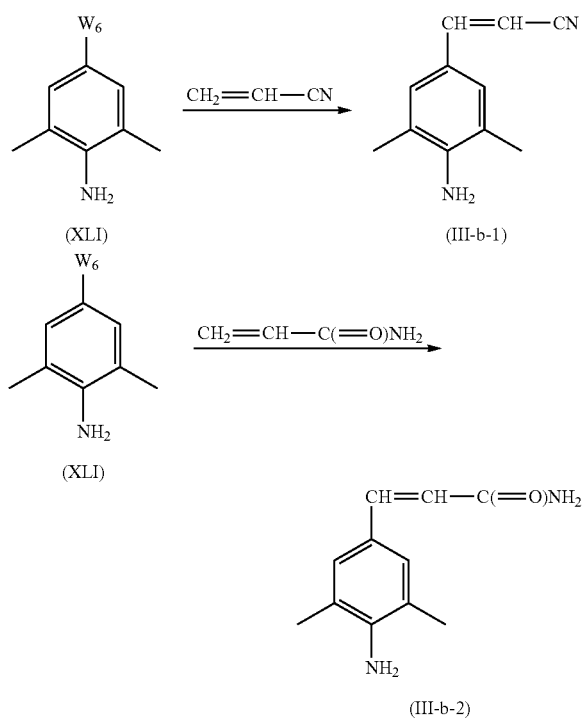

Suitable leaving groups in the above reaction are for example halo, triflate, tosylate, mesylate and the like. Preferably, $W_6$ is halo, more preferably iodo or bromo.

The palladium (Pd) catalyst may be a homogeneous Pd catalyst, such as for example $Pd(OAc)_2$, $PdCl_2$, $Pd(PPh_3)_4$, $Pd(PPh_3)_2Cl_2$, bis(dibenzylidene acetone) palladium, palladium thiomethylphenylglutaramide metallacycle and the like, or a heterogeneous Pd catalyst, such as for example palladium on charcoal, palladium on metal oxides, palladium on zeolites.

Preferably, the palladium catalyst is a heterogeneous Pd catalyst, more preferably palladium on charcoal (Pd/C). Pd/C is a recoverable catalyst, is stable and relatively inexpensive. It can be easily separated (filtration) from the reaction mixture thereby reducing the risk of Pd traces in the final product. The use of Pd/C also avoids the need for ligands, such as for example phosphine ligands, which are expensive, toxic and contaminants of the synthesized products.

Suitable bases in the above reaction are for example sodium acetate, potassium acetate, N,N-diethylethanamine, sodium hydrogencarbonate, sodium hydroxide and the like.

Suitable solvents in the above reaction are for example acetonitrile, N,N-dimethylacetamide, an ionic liquid e.g. [bmim]$PF_6$, N,N-dimethylformamide, water, tetrahydrofuran, dimethylsulphoxide, 1-methyl-2-pyrrolidinone and the like.

Intermediates of formula (III-b-2) can be converted into an intermediate of formula (III-b-1) in the presence of a suitable dehydrating agent. The dehydration can be performed according to methodologies well-known to the person skilled in the art, such as the ones disclosed in "Comprehensive Organic Transformations. A guide to functional group preparations" by Richard C. Larock, John Wiley & Sons, Inc, 1999, p 1983-1985, which is incorporated herein as reference. Different suitable reagents are enumerated in said reference, such as for example $SOCl_2$, $HOSO_2NH_2$, $ClSO_2NCO$, $MeO_2CNSO_2NEt_3$, $PhSO_2Cl$, $TsCl$, $P_2O_5$, $(Ph_3PO_3SCF_3)O_3SCF_3$, polyphosphate ester, $(EtO)_2POP(OEt)_2$, $(EtO)_3PI_2$, 2-chloro-1,3,2-dioxaphospholane, 2,2,2-trichloro-2,2-dihydro-1,3,2-dioxaphospholane, $POCl_3$, $PPh_3$, $P(NCl_2)_3$, $P(NEt_2)_3$, $COCl_2$, $NaCl.AlCl_3$, $ClCOCOCl$, $ClCO_2Me$, $Cl_3CCOCl$, $(CF_3CO)_2O$, $Cl_3CN=CCl_2$, 2,4,6-trichloro-1,3,5-triazine, $NaCl.AlCl_3$, $HN(SiMe_2)_3$, $N(SiMe_2)_4$, $LiAlH_4$ and the like. All the reagents listed in said publication are incorporated herein as reference.

Intermediates of formula (XX) wherein $R^3$ represents $CR^{c'}=CR^c$—CN with $R^c$ and $R^{c'}$ as described hereinabove, said intermediates being represented by formula (XX-b), can be prepared from an intermediate of formula (XXI) by the reaction described above for the preparation of a compound of formula (I-f).

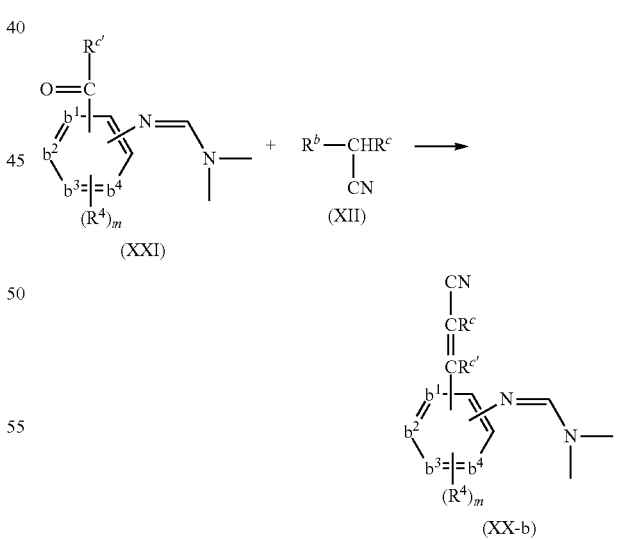

Intermediates of formula (XXI) can be prepared by oxidation of an intermediate of formula (XXII) in the presence of a suitable oxidizing agent, such as for example $KMnO_4$, in the presence of a suitable solvent, such as for example methylene chloride and tris[2-(2-methoxy ethoxy)ethyl]amine

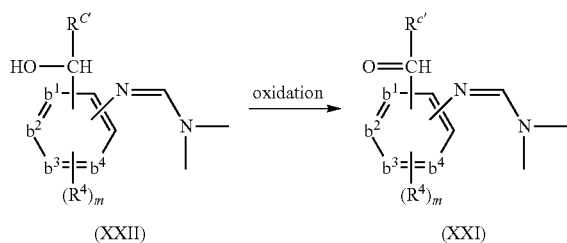

Intermediates of formula (XXI) wherein $R^{c'}$ is H, said intermediates being represented by formula (XXI-a), can also be prepared by reacting an intermediate of formula (XXIII) wherein $W_4$ represents a suitable leaving group, such as halo, e.g. bromo, with N,N-dimethylformamide in the presence of nBuLi and in the presence of a suitable solvent, such as for example tetrahydrofuran.

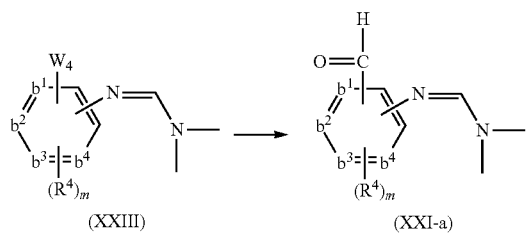

Intermediates of formula (XXII) wherein $R^{c'}$ represents $C_{1-4}$alkyl, said intermediates being represented by formula (XXII-a), can be prepared by reacting an intermediate of formula (XXIII) with an intermediate of formula (XXIV) in the presence of nBuLi and in the presence of a suitable solvent, such as for example tetrahydrofuran.

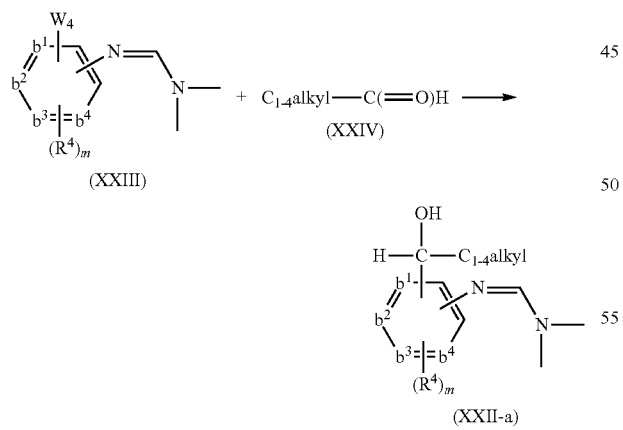

Intermediates of formula (XI) can be prepared by reacting an intermediate of formula (XXV) with an intermediate of formula (II), optionally in the presence of a suitable base, such as for example 1-methyl-pyrrolidin-2-one, or a suitable acid, such as for example hydrochloric acid.

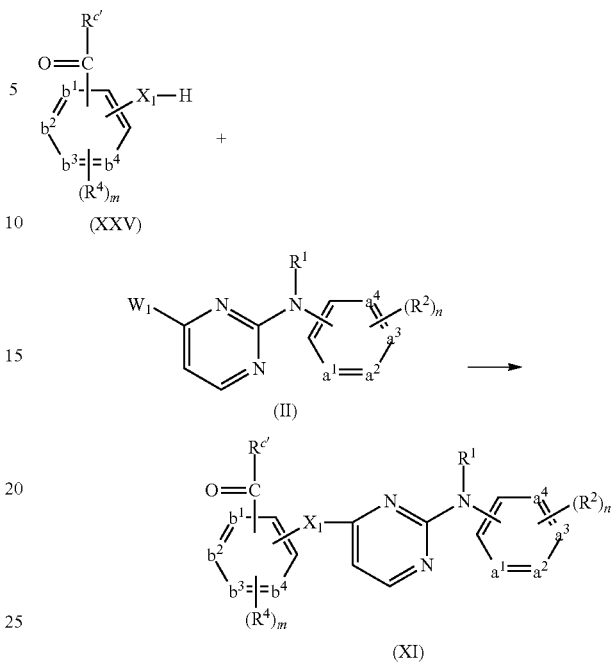

Intermediates of formula (XV) can be prepared by reacting an intermediate of formula (XXVI) with an intermediate of formula (II) in the presence of a suitable base, such as for example 1-methyl-pyrrolidin-2-one and sodium hydride and a suitable solvent, such as for example dioxane.

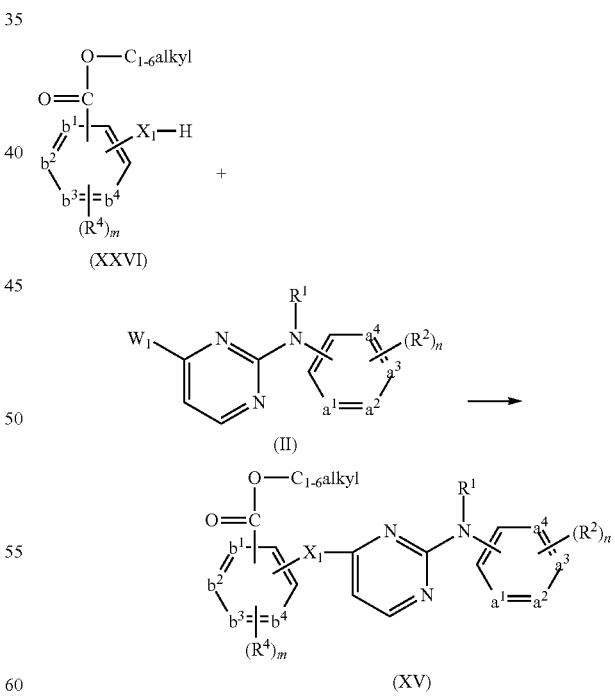

Intermediates of formula (VII) can be prepared by reacting an intermediate of formula (XXVII) with a leaving group introducing agent of formula (XIX'), such as for example $SOCl_2$, in the presence of a suitable solvent, such as for example methylene chloride.

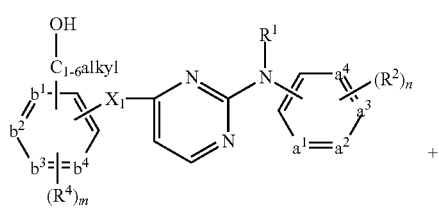

(XXVII)

$W_3—R$ (XIX')

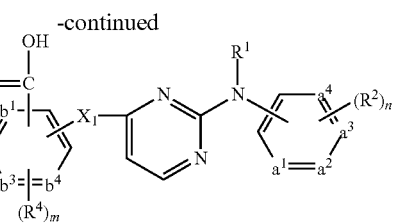

(XXXI)

Intermediates of formula (XI-b) can be prepared by oxidizing an intermediate of formula (XXVII-a) in the presence of a suitable oxidizing agent, such as for example $MnO_2$, and a suitable solvent, such as for example methylene chloride, N,N-dimethylformamide.

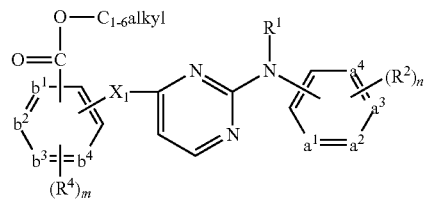

(VII)

Intermediates of formula (XXVII) wherein $C_{1-6}$alkyl represents $CH_2$, said intermediates being represented by formula (XXVII-a), can be prepared by reducing an intermediate of formula (XV) or formula (XXXI) with a suitable reducing agent, such as for example $LiAlH_4$, in the presence of a suitable solvent, such as for example tetrahydrofuran.

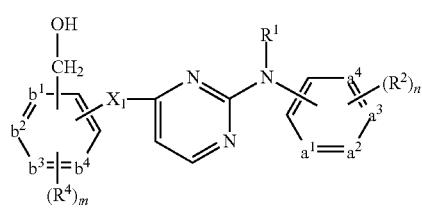

Intermediates of formula (XXVII-a) can be converted to an intermediate of formula (XXXI) by reaction with Jones reagent in the presence of a suitable solvent, such as for example acetone.

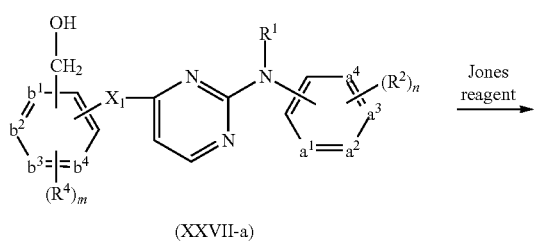

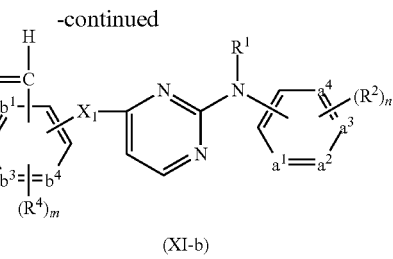

(XI-b)

Intermediates of formula (XIV) can be prepared by reacting an intermediate of formula (XV) with $H_2N—NH_2$ in the presence of a suitable solvent, such as for example an alcohol, e.g. ethanol and the like.

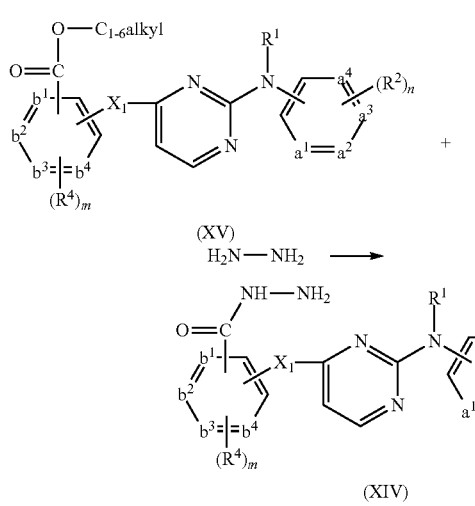

(XV)

H₂N—NH₂ →

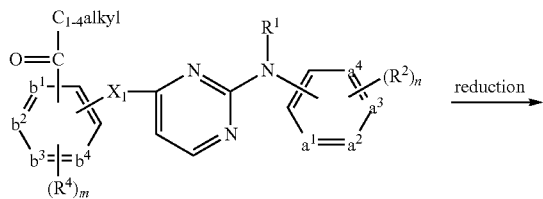

(XIV)

Intermediates of formula (IX) and (XI-a) can be reduced to an intermediate of formula (XXVII'-a) and (XXVII'-b) in the presence of a suitable reducing agent, such as for example NaBH₄, LiAlH₄ or BuLi and a suitable solvent, such as for example tetrahydrofuran or an alcohol, e.g. methanol, ethanol and the like.

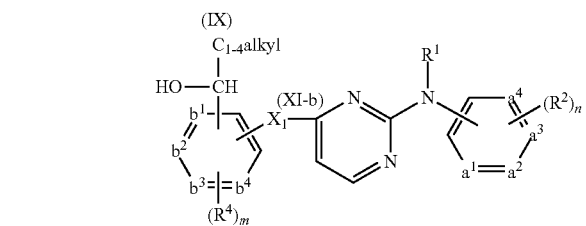

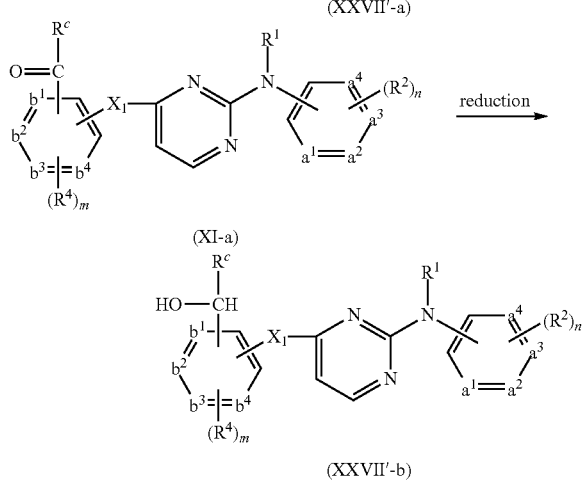

An intermediate of formula (XI-b) can be converted into an intermediate of formula (XXVII'-a) by reaction with C₁₋₄alkyl-Iodide in the presence of Mg and a suitable solvent, such as for example diethylether and tetrahydrofuran.

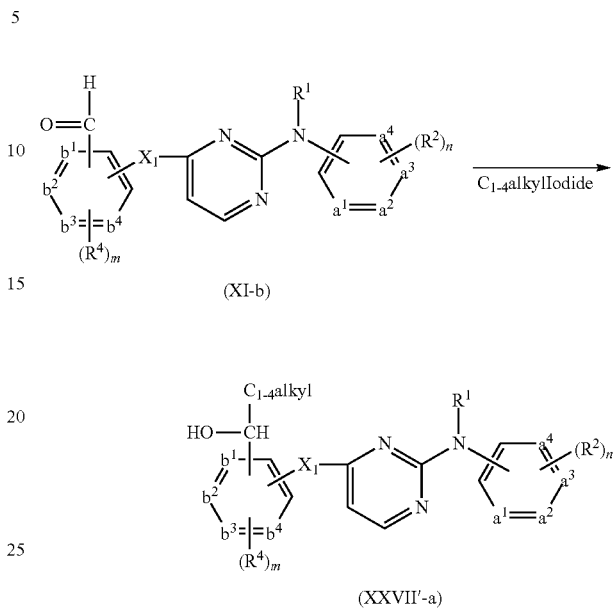

Intermediates of formula (XVIII) can be prepared by reacting an intermediate of formula (XI-b) with H₂N—NH₂ in the presence of a suitable solvent, such as for example an alcohol, e.g. ethanol and the like.

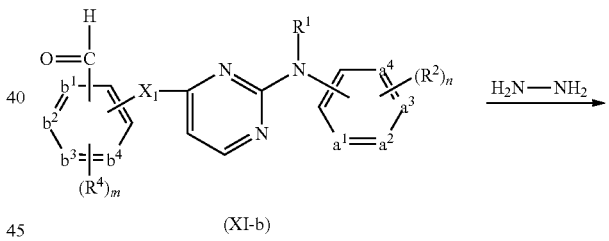

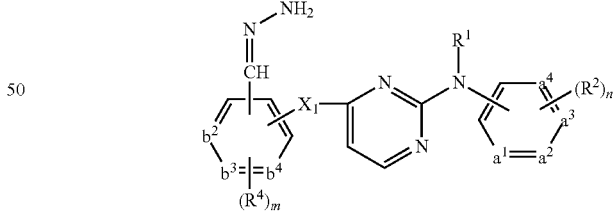

Intermediates of formula (XXIX) or (XXXI) can be prepared by hydrolizing an intermediate of formula (XXXVII) wherein C₂₋₆alkenyl' represents C₂₋₆alkenyl optionally substituted cyano, or an intermediate of formula (XV) in the presence of a suitable aqueous acid solution, such as for example hydrochloric acid 2N and the like, and in the presence of a suitable solvent, such as for example an alcohol, e.g. isopropanol and the like.

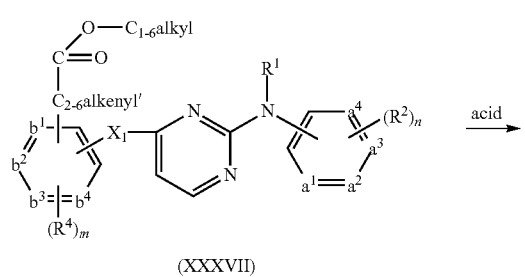

(XXXVII)

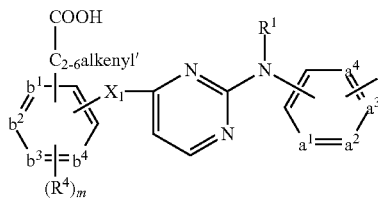

(XXIX)

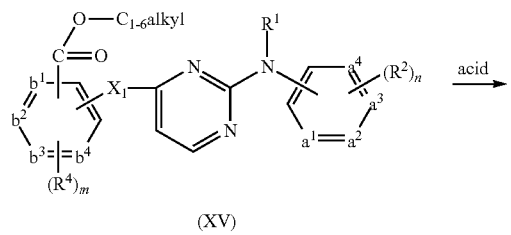

(XV)

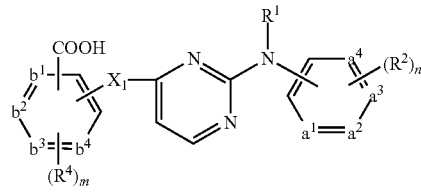

(XXXI)

Intermediates of formula (XXXVII) wherein $C_{2-6}$alkenyl is CH=CH, said intermediates being represented by formula (XXXVII-a), can be prepared by reacting an intermediate of formula (XI-b) with a Wittig or Horner-Emmons reagent of formula (XII″), wherein $R^b$ represents for example $(Phenyl)_3P^+$—Cl⁻ or $(CH_3CH_2—O)_2P(=O)$—, which can be considered as a suitable precursor of a phosphorus ylide, in the presence of a suitable solvent, such as for example tetrahydrofuran.

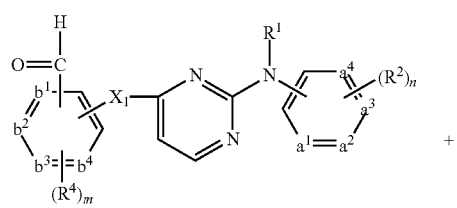

(XI-b)

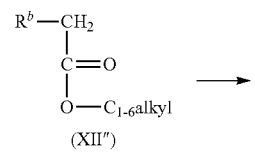

(XII″)

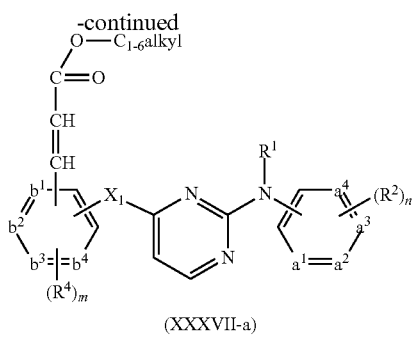

(XXXVII-a)

Intermediates of formula (XXXVII) wherein $C_{2-6}$alkenyl' is —CH=C(CN)—, said intermediates being represented by formula (XXXVII-b), can be prepared by reacting an intermediate of formula (XI-b) with NC—CH₂—C(=O)O—$C_{1-6}$alkyl, in the presence of a suitable base, such as for example piperidine, and a suitable solvent, such as for example an alcohol, e.g. ethanol.

(XI-b)

NC—CH₂
|
C=O
|
O—$C_{1-6}$alkyl (XXXVII-b)

Intermediates of formula (XXXIV) can be prepared by reducing an intermediate of formula (XXXVIII) in the presence H₂ and a suitable catalyst, such as for example palladium on charcoal or Raney Nickel, and in the presence of a suitable solvent, such as for example an alcohol, e.g. methanol and the like.

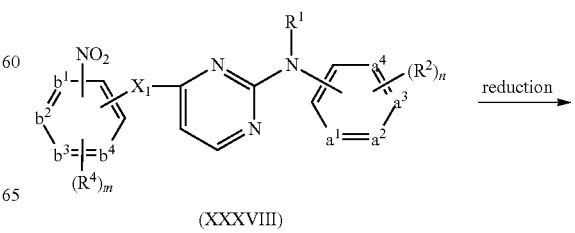

(XXXVIII)

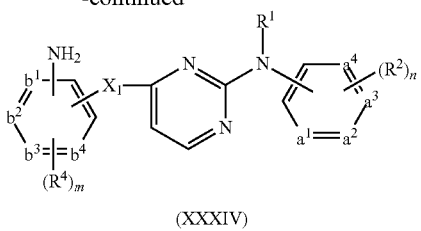

(XXXIV)

Intermediates of formula (XXXV) can be prepared by reacting an intermediate of formula (VII-a) in the presence of triphenylphosphine and a suitable solvent, such as for example acetonitrile.

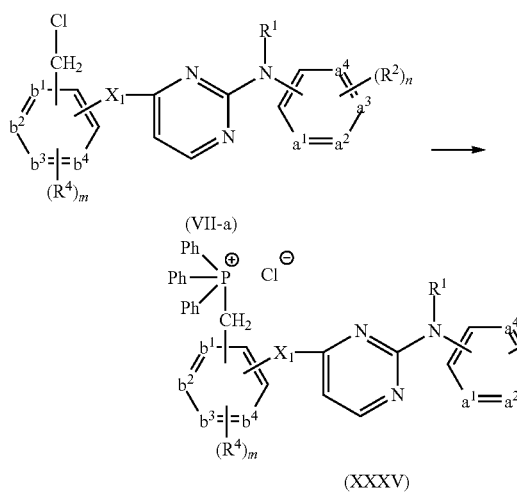

Intermediates of formula (XXXIX) can be prepared by reacting an intermediate of formula (XL) with an intermediate of formula (II-a) wherein $W_5$ and $W_1$ are as defined hereinbefore.

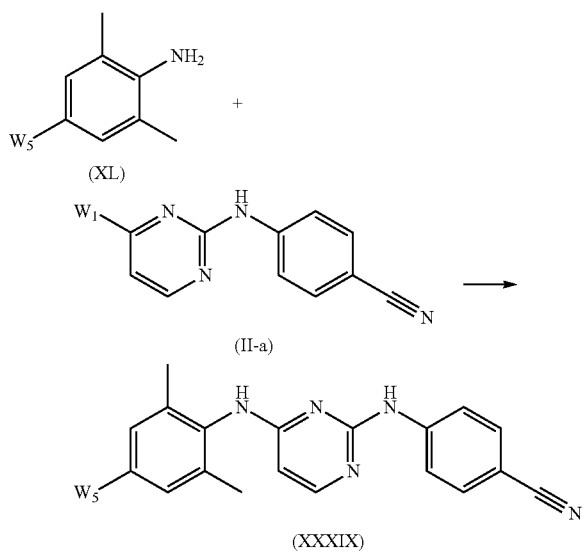

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{1-6}$alkyl or benzyl esters.

The protection and deprotection of functional groups may take place before or after a reaction step.

The use of protecting groups is fully described in 'Protective Groups in Organic Chemistry', edited by J W F McOmie, Plenum Press (1973), and 'Protective Groups in Organic Synthesis' $2^{nd}$ edition, T W Greene & P G M Wutz, Wiley Interscience (1991).

The present invention also concerns new compounds of formula (VII), (XXVII), (XXIX) and (XXXVII) which can be used as intermediates in the synthesis of the compounds of formula (I) and which also exhibit HIV replication inhibiting activity.

In particular, the present invention also relates to a compound of formula

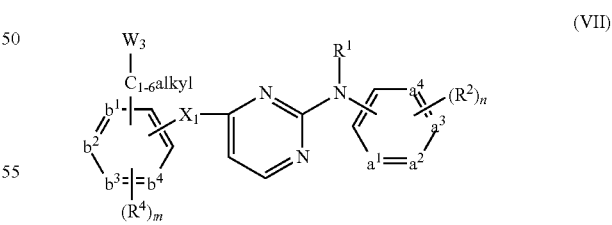

(VII)

a N-oxide, a pharmaceutically acceptable addition salt, a quaternary amine and a stereochemically isomeric form thereof, wherein $R^1$, $R^2$, $R^4$, $X_1$, m, n, $-a^1=a^2-a^3=a^4-$ and $-b^1=b^2-b^3=b^4-$ are as defined hereinabove for the compounds of formula (I) and $W_3$ represents a suitable leaving group such as for example halo, e.g. chloro and the like.

The present invention also relates to a compound of formula

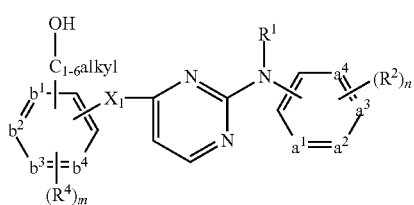

(XXVII)

a N-oxide, a pharmaceutically acceptable addition salt, a quaternary amine and a stereochemically isomeric form thereof, wherein $R^1$, $R^2$, $R^4$, $X_1$, m, n, -$a^1$=$a^2$-$a^3$=$a^4$- and -$b^1$=$b^2$-$b^3$=$b^4$- are as defined hereinabove for the compounds of formula (I).

The present invention also relates to a compound of formula

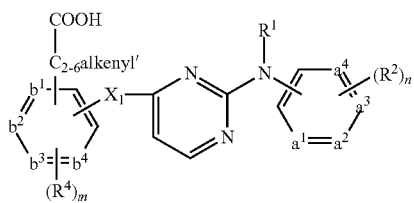

(XXIX)

a N-oxide, a pharmaceutically acceptable addition salt, a quaternary amine and a stereochemically isomeric form thereof, wherein $R^1$, $R^2$, $R^4$, $X_1$, m, n, -$a^1$=$a^2$-$a^3$=$a^4$- and -$b^1$=$b^2$-$b^3$=$b^4$- are as defined hereinabove for the compounds of formula (I) and $C_{2-6}$alkenyl' represents $C_{2-6}$alkenyl optionally substituted with cyano.

The present invention also relates to a compound of formula

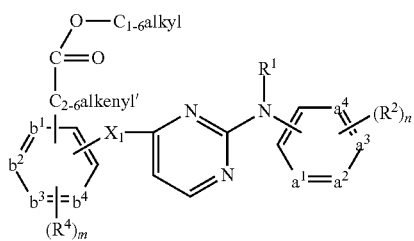

(XXXVII)

a N-oxide, a pharmaceutically acceptable addition salt, a quaternary amine and a stereochemically isomeric form thereof, wherein $R^1$, $R^2$, $R^4$, $X_1$, m, n, -$a^1$=$a^2$-$a^3$=$a^4$- and -$b^1$=$b^2$-$b^3$=$b^4$- are as defined hereinabove for the compounds of formula (I) and $C_{2-6}$alkenyl' represents $C_{2-6}$alkenyl optionally substituted with cyano.

Compounds of formula (III-b) as depicted below intervene in the synthesis of compounds of formula (I).

Therefore, the present invention also relates to a compound of formula (III-b)

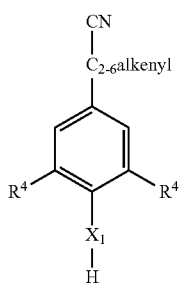

(III-b)

a N-oxide, a pharmaceutically acceptable addition salt, a quaternary amine and a stereochemically isomeric form thereof, wherein $R^4$ and $X_1$ are as defined hereinabove for the compounds of formula (I).

Preferred compounds of formula (III-b) are those compounds wherein $X_1$ represents NH. More preferred compounds of formula (III-b) are those compounds wherein $X_1$ represents NH and $C_{2-6}$alkenyl represents CH=CH. Most preferred compounds of formula (III-b) are the compounds of formula (III-b-1) as described hereinabove.

The compounds of formula (I), (I'), (I''), (I'''), (VII), (XXVII), (XXIX) and (XXXVII) show antiretroviral properties (reverse transcriptase inhibiting properties), in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against (multi) drug resistant HIV strains, in particular (multi) drug resistant HIV-1 strains, more in particular the present compounds show activity against HIV strains, especially HIV-1 strains, that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and in particular commercial non-nucleoside reverse transcriptase inhibitors. The present compounds also have little or no binding affinity to human α-1 acid glycoprotein; human α-1 acid glycoprotein does not or only weakly affect the anti HIV activity of the present compounds.

Due to their antiretroviral properties, particularly their anti-HIV properties, especially their anti-HIV-1-activity, the compounds of formula (I), their N-oxides, pharmaceutically acceptable addition salts, quaternary amines and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In view of the utility of the compounds of formula (I), there is provided a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated f-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated α-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermo-dynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:
a) dissolving the compound of formula (I) and the water-soluble polymer in an appropriate solvent, optionally at elevated temperatures;
b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
a) mixing a compound of formula (I) and an appropriate water-soluble polymer,
b) optionally blending additives with the thus obtained mixture,
c) heating and compounding the thus obtained blend until one obtains a homogenous melt,
d) forcing the thus obtained melt through one or more nozzles; and
e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 µm, preferably less than 400 µm and most preferably less than 125 µm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa·s more preferably of 1 to 700 mPa·s, and most preferred of 1 to 100 mPa·s. For example, suitable water-soluble polymers include alkylcelluloses, hydroxyalkyl-celluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γcyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxy-methyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins is sulfobutylcyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) can be used alone or in combination with other therapeutic agents, such as anti-virals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of an antiretroviral compound and a compound of formula (I) can be used as a medicine. Thus, the present invention also relates to a product containing (a) a compound of formula (I), and (b) another antiretroviral compound, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as suramine, pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir and the like; non-nucleoside reverse transcriptase inhibitors such as nevirapine (11-cyclopropyl-5,11-dihydro-4-methyl-6H-dipyrido-[3,2-b:2', 3'-e][1,4]diazepin-6-one), efavirenz, delavirdine, TMC-120, TMC-125 and the like; phosphonate reverse transcriptase inhibitors, e.g. tenofovir and the like; compounds of the TIBO (tetrahydro-imidazo[4,5,1-j k][1,4]-benzodiazepine-2 (1H)-one and thione)-type e.g. (S)-8-chloro-4,5,6,7-tetrahydro-5-methyl-6-(3-methyl-2-butenyl)-imidazo-[4,5,1-jk] [1,4]benzodiazepine-2(1H)-thione; compounds of the α-APA (α-anilino phenyl acetamide) type e.g. α-[(2-nitrophenyl)amino]-2,6-di-chlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-126, BMS-232632, VX-175 and the like; fusion inhibitors, e.g. T-20, T-1249 and the like; CXCR4 receptor antagonists, e.g. AMD-3100 and the like; inhibitors of the viral integrase; nucleotide-like reverse transcriptase inhibitors, e.g. tenofovir and the like; ribonucleotide reductase inhibitors, e.g. hydroxyurea and the like.

By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional antiretroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia. A compound of formula (I) can also be combined with another compound of formula (I).

Although the present invention focuses on the use of the present compounds for preventing or treating HIV infections, the present compounds may also be used as inhibitory agents for other viruses which depend on similar reverse transcriptases for obligatory events in their life cycle.

EXAMPLES

The following examples are intended to illustrate the present invention.

Experimental Part

Hereinafter, "DMF" is defined as N,N-dimethylformamide, "DIPE" is defined as diisopropyl ether, "THF" is defined as tetrahydrofurane, "DMA" is defined as N,N-dimethylacetamide, "DMSO" is defined as dimethylsulfoxide, "DME" is defined as dimethyl ether, "EtOAc" is defined as ethylacetate, "EDCI" is defined as N'-(ethylcarbonimidoyl)-N,N-dimethyl-1,3-propanediamine.

A. Preparation of the Intermediate Compounds

Example A1 a) The Preparation of Intermediate 1

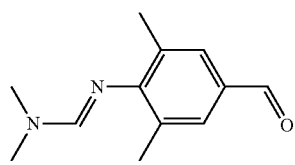

nBuLi (0.012 mol) was added dropwise at −70° C. to a mixture of N'-(4-bromo-2,6-dimethylphenyl)-N,N-dimethylmethanimidamide (0.0078 mol) in THF (20 ml) under N₂ flow. The mixture was stirred at −30° C. for 30 minutes, then cooled to −70° C. A mixture of DMF (0.078 mol) in THF (30 ml) was added dropwise. The mixture was stirred at −70° C. for 2 hours, then brought to 0° C., poured out into H₂O and extracted with ethyl acetate. The organic layer was separated, dried (MgSO₄), filtered and the solvent was evaporated. Yield: 1.8 g of intermediate 1.

b) The Preparation of Intermediate 2

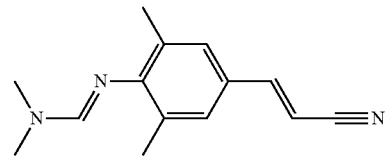 [SMILES: Cc1cc(/C=C/C#N)cc(C)c1/N=C/N(C)C]

A mixture of diethyl (cyanomethyl)phosphonate (0.0037 mol) in THF (10 ml) was cooled to 5° C. under N₂ flow. Potassium tert.-butoxide (0.0037 mol) was added portionwise. The mixture was stirred at 5° C. for 30 minutes, then stirred at room temperature for 30 minutes. A mixture of intermediate 1 (0.0024 mol) in THF (10 ml) was added. The mixture was stirred at room temperature for 1 hour, then poured out into H₂O and extracted with CH₂Cl₂. The organic layer was separated, dried (MgSO₄), filtered and the solvent was evaporated. Yield: 0.82 g (100%) of intermediate 2.

c) The Preparation of Intermediate 3 and Intermediate 22

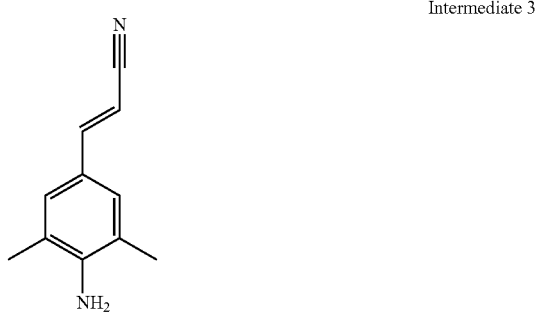

Intermediate 3

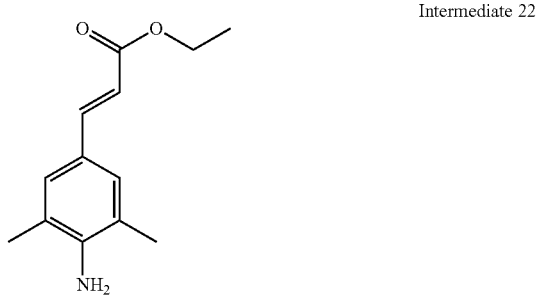

Intermediate 22

A mixture of intermediate 2 (0.059 mol) and ZnCl₂ (0.299 mol) in ethanol (150 ml) was stirred and refluxed for 24 hours, then poured out into K₂CO₃ solution (10% in water)

and extracted with CH$_2$Cl$_2$. The organic layer was separated, dried (MgSO$_4$), filtered and the solvent was evaporated. The residue (9 g) was crystallized from DIPE. The precipitate was filtered off and dried. Yield: 0.8 g (6%) of intermediate 22. The filtrate was concentrated and recrystallized from DIPE to obtain 6 g of intermediate 3.

Alternatively, intermediate 3 was also prepared as follows:

To a solution of 159 g of 4-iodo-2,6-dimethyl-benzenamine was added 63.8 g of sodium acetate. The reaction mixture was kept under nitrogen atmosphere. 7 g of moistered palladium on charcoal (Pd/C 10%) and 64.4 ml of acrylonitrile was added. The reaction mixture was heated to 130° C. and stirred overnight. After cooling to room temperature, 0.5 l of toluene and 0.5 l of N,N-dimethylacetamide was added. The reaction mixture was filtered over Dicalite and the filter was washed with 0.5 l of toluene. Water (6 l) was added to the mixture which was stirred for 30 minutes. The layers were separated. To the aqueous layer, 1 l of toluene was added and the mixture was stirred for 30 minutes. The layers were separated again. The separated organic layers were collected and the solvent was evaporated, yielding 123 g of intermediate 3.

Intermediate 3 was converted into its hydrochloric acid salt as follows:

To a mixture of 123 g of intermediate 3 in 630 ml of ethanol was added 1.25 l of diisopropyl ether. The reaction mixture was kept under nitrogen atmosphere. The mixture was heated to 60° C. and stirred for 30 minutes. 120 ml of a 6 N solution of hydrochloric acid in 2-propanol was added and the mixture was stirred for 30 minutes. After cooling to room temperature, the reaction mixture was filtered and the residue was washed with 100 ml of 2-propanol. The resulting residue was dried under reduced pressure at 50° C. Yield: 103 g (77%) of the hydrochloric acid salt (1:1) of intermediate 3.

Intermediate 3 (E) was prepared as follows:

x) Preparation of Intermediate 3a (E)

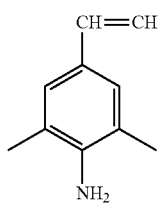

Intermediate 3a (E)

In 10 ml acetonitrile, dry, was dissolved 2.00 g (10.0 mol) of 4-bromo-2,6-dimethylaniline, 1.07 g (1.5 eq) of acrylamide, 224 mg (0.1 eq) of Pd(OAc)$_2$, 609 mg (0.2 eq) of tris(2-methylphenyl)phosphine and 1.52 g of N,N-diethylethanamine. The mixture was purged with N$_2$ for 20 minutes and stirred overnight at 70° C. The mixture was diluted with 150 ml of methylene chloride, washed with saturated aqueous NaHCO$_3$ solution, dried (sat. NaCl, Na$_2$SO$_4$) and filtered. The solvent was evaporated and the residue was stirred in diisopropyl ether followed by filtration. Yield: 1.51 g (79.5%) of intermediate 3a (E).

y) Preparation of Intermediate 3 (E)

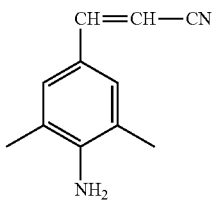

Intermediate 3 (E)

POCl$_3$ (3 ml) was cooled to 0° C. and 500 mg (2.63 mmol) of intermediate 3a (E) was added. After 30 minutes, the cooling bath was removed and the mixture was stirred overnight at 20° C. The mixture was added dropwise to 150 ml of diisopropyl ether while stirring vigorously. The precipitate was filtered and washed with diisopropyl ether. The residue was added to 100 ml ethyl acetate/100 ml of saturated aqueous NaHCO$_3$ solution and stirred. The ethyl acetate layer was separated, dried (sat. NaCl, Na$_2$SO$_4$) and filtered. The solvent was evaporated. Yield: 380 mg (84%) of intermediate 3 (E).

d) The Preparation of Intermediate 4

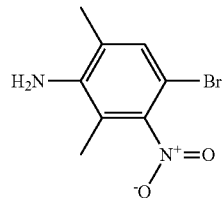

A mixture of 4-bromo-2,6-dimethylbenzenamine (0.024 mol) in H$_2$SO$_4$ (30 ml) was stirred at −5° C. KNO$_3$ (0.024 mol) was added slowly. The mixture was stirred at −5° C. for 30 minutes, poured out into H$_2$O and extracted with ethyl acetate. The organic layer was washed with H$_2$O, separated, dried (MgSO$_4$), filtered and the solvent was evaporated. The residue (0.058 g, 95%) was purified by column chromatography over silica gel (eluent: cyclohexane/ethyl acetate; 70/30; 15-40 μm). The pure fractions were collected and the solvent was evaporated. Yield: 4.1 g of intermediate 4.

Example A1A

The Preparation of Intermediate 28

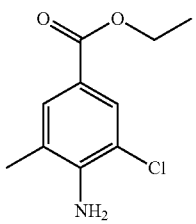

1-chloro-pyrrolidine-2,5-dione (0.032 mol) was added at 60° C. to a mixture of 4-amino-3-methyl-benzoic acid ethyl ester [CAS 40800-65-5] (0.029 mol) in CH$_3$CN (50 ml). The mixture was stirred and refluxed slowly. K$_2$CO$_3$ 10% was added. The mixture was extracted with CH$_2$Cl$_2$. The organic layer was evaporated. The residue (6.6 g) was purified by column chromatography over silica gel (eluent: cyclohexane/EtOAc 85/15; 15-40 μm). The pure fractions were collected and the solvent was evaporated. Yield: 5.2 g of intermediate 28 (84%).

Example A2

A mixture of 4-[(1,4-dihydro-4-oxo-2-pyrimidinyl)amino]benzonitrile (0.12 mol) in POCl$_3$ (90 ml) was stirred and refluxed under Argon for 20 minutes. The reaction mixture was slowly poured onto 750 ml ice/water, and the solid was separated by filtration. The solid was suspended in 500 ml water, and the pH of the suspension was adjusted to neutral by adding a 20% NaOH solution. The solid was again separated by filtration, suspended in 200 ml 2-propanone, and 1000 ml CH$_2$Cl$_2$ was added. The mixture was heated until all solid had dissolved. After cooling to room temperature, the aqueous layer was separated, and the organic layer was dried. During removal of the drying agent by filtration, a white solid formed in the filtrate. Further cooling of the filtrate in the freezer, followed by filtration, yielded 21.38 g (77.2%) of [4-[(4-chloro-2-pyrimidinyl)amino]benzonitrile (interm. 5).

Example A3 a) The Preparation of Intermediate 6

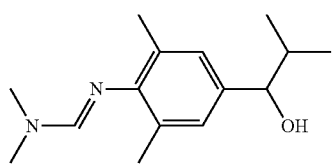 [SMILES: Cc1cc(C(O)C(C)C)cc(C)c1/N=C/N(C)C]

nBuLi (0.024 mol) was added dropwise at −70° C. to a mixture of N'-(4-bromo-2,6-dimethylphenyl)-N,N-dimethylmethanimidamide (0.0157 mol) in THF (50 ml) under N$_2$ flow. The mixture was stirred at −30° C. for 30 minutes, then cooled to −70° C. A solution of 2-methylpropanal (0.055 mol) in THF (50 ml) was added. The mixture was stirred at −70° C. for 2 hours, then brought to 0° C., poured out into H$_2$O and extracted with CH$_2$Cl$_2$. The organic layer was separated, dried (MgSO$_4$), filtered and the solvent was evaporated. The residue (6.7 g) was purified by column chromatography over silica gel (eluent: CH$_2$Cl$_2$/CH$_3$OH/NH$_4$OH 95/5/0.5; 15-40 μm). Two fractions were collected and the solvent was evaporated. Fraction 1: yield: 1.5 g of intermediate 6 (38%).

b) The Preparation of Intermediate 7

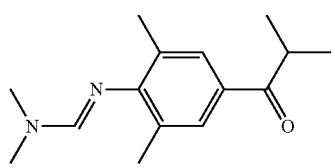 [SMILES: Cc1cc(C(=O)C(C)C)cc(C)c1/N=C/N(C)C]

Tris[2-(2-methoxyethoxy)ethyl]amine (0.0193 mol) was added at room temperature to a solution of intermediate 6 (0.0048 mol) in CH$_2$Cl$_2$ (20 ml). KMnO$_4$ (0.0193 mol) was added portionwise. The mixture was stirred at room temperature overnight, then filtered over celite and washed with CH$_2$Cl$_2$. The organic layer was washed with K$_2$CO$_3$ 10%, separated, dried (MgSO$_4$), filtered and the solvent was evaporated. Yield: 1.2 g (100%) of intermediate 7.

c) The Preparation of Intermediate 8

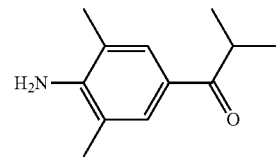

A mixture of intermediate 7 (0.0043 mol) and ZnCl$_2$ (0.017 mol) in ethanol (20 ml) was stirred and refluxed overnight, poured out into H$_2$O and extracted with CH$_2$Cl$_2$/CH$_3$OH. The organic layer was separated, dried (MgSO$_4$), filtered and the solvent was evaporated. Yield: 0.94 g (82%) of intermediate 8.

d-1) the Preparation of Intermediate 9

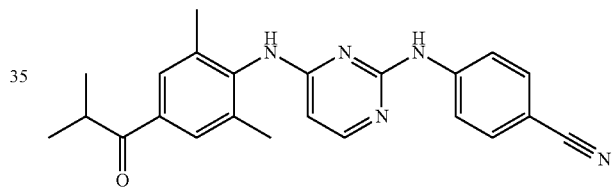

A mixture of intermediate 8 (0.0049 mol) and intermediate 5 (0.0025 mol) was stirred at 150° C. for 2 hours and taken up in K$_2$CO$_3$ 10%/CH$_2$Cl$_2$/CH$_3$OH. The organic layer was separated, dried (MgSO$_4$), filtered and the solvent was evaporated. The residue (1.3 g) was crystallized from DIPE. The precipitate was filtered off and dried. The mother layer was purified by column chromatography over silica gel (eluent: CH$_2$Cl$_2$/CH$_3$OH 98.5/1.5; 15-40 μm). The pure fractions were collected and the solvent was evaporated. Yield: 0.21 g of intermediate 9.

d-2) the Preparation of Intermediate 29

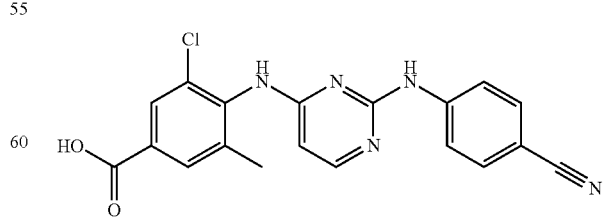

A mixture of intermediate 28 (0.023 mol) and intermediate 5 (prepared according to A2) (0.025 mol) in HCl 3N (10 ml) was stirred at 105° C. then brought to room temperature and filtered. The precipitate was washed with DIPE and dried. Yield: 8.4 g of intermediate 29 (96%)

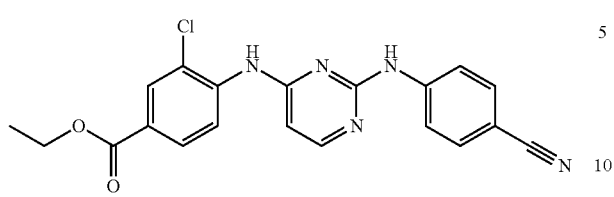

d-3) the Preparation of Intermediate 30

A mixture of 4-amino-3-chloro benzoic acid ethyl ester [CAS 82765-44-4] (0.02 mol) and intermediate 5 (prepared according to A2) (0.0243 mol) in 1-methyl-pyrrolidin-2-one (40 ml) was stirred at 180° C. for 2 hours, then poured out into H$_2$O and extracted three times with EtOAc (80 ml). The organic layer was separated, dried (MgSO$_4$), filtered and the solvent was evaporated. The residue (10 g) was purified by column chromatography over silica gel (eluent: CH$_2$Cl$_2$ 100; 15-30 μm).

Two fractions were collected and the solvent was evaporated. Yield: 1.7 g F1 and 1 g F2. F2 was taken up in diethyl ether. The precipitate was filtered off and dried. Yield: 0.95 g of intermediate 30 (12%).

e-1) the Preparation of Intermediate 17

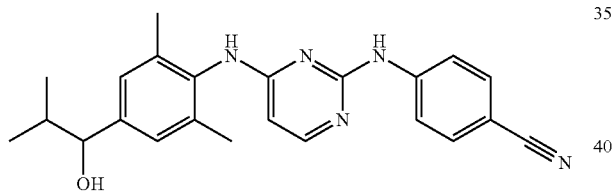

NaBH$_4$ (0.0001 mol) was added portionwise at 5° C. to a mixture of intermediate 9 (0.0001 mol) in ethanol (7 ml) under N$_2$ flow. The mixture was stirred at 5° C. for 1 hour, poured out on ice and extracted with CH$_2$Cl$_2$. The organic layer was separated, dried (MgSO$_4$), filtered, and the solvent was evaporated. The residue (0.1 g) was crystallized from DIPE. The precipitate was filtered off and dried. Yield: 0.044 g of intermediate 17.

e-2) the Preparation of Intermediate 32

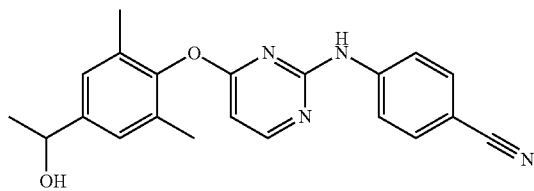 [SMILES: Cc1cc(C(C)O)cc(C)c1Oc1ccnc(Nc2ccc(C#N)cc2)n1]

BuLi 1.6 M (0.009 mol) was added at −78° C. to a mixture of

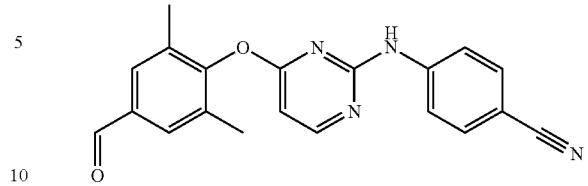

(intermediate 31)

(prepared according to A4a) (0.0029 mol) in THF (25 ml) under N$_2$ flow. The mixture was stirred at −78° C. for 10 minutes, then brought to room temperature and stirred for 3 hours. H$_2$O was added. The mixture was extracted with CH$_2$Cl$_2$. The organic layer was separated, dried (MgSO$_4$), filtered, and the solvent was evaporated. The residue (1.28 g) was purified by column chromatography over silica gel (eluent: CH$_2$Cl$_2$/CH$_3$OH/NH$_4$OH 98/2/0.1; 15-40 μm). Three fractions were collected and the solvent was evaporated. Yield: 0.189 g of fraction 1, 0.14 g of fraction 2 and 0.5 g of fraction 3 (48%). Fraction 3 was purified by column chromatography over kromasil (eluent: CH$_2$Cl$_2$/EtOAc 80/20; 10 μm). Two fractions (F1, F2) were collected and the solvent was evaporated. Yield: 0.25 g F1 (24%) and 0.1 g of F2. F1 was crystallized from diethyl ether. The precipitate was filtered off and dried. Yield: 0.21 g of intermediate 32 (20%).

e-3) the Preparation of Intermediate 34

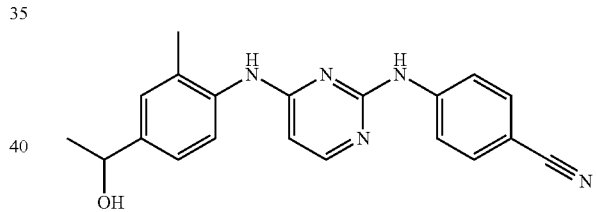

A solution of methylmagnesium iodide (1.0M solution in diethylether) (0.6 ml) was added to a solution of

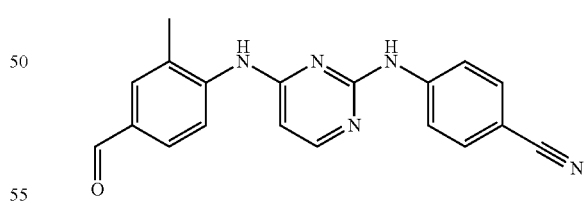

intermediate 33 (prepared according to A5.a) (0.0006 mol) in THF (3 ml). The mixture was stirred for 2 hours. H$_2$O was added. The mixture was filtered over celite. H$_2$O was added. The mixture was extracted with EtOAc. The organic layer was separated, dried (MgSO$_4$), filtered, and the solvent was evaporated. The residue (0.05 g) was purified by column chromatography over silica gel (eluent: CH$_2$Cl$_2$/CH$_3$OH 96/4; 15-40 μm). The pure fractions were collected and the solvent was evaporated. Yield: 0.015 g of intermediate 34 (7.2%).

Example A4 a) The Preparation of Intermediate 10

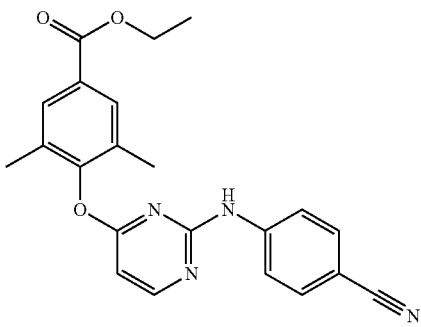 [SMILES: CCOC(=O)c1cc(C)c(Oc2ccnc(Nc3ccc(C#N)cc3)n2)c(C)c1]

A mixture of ethyl 3,5-dimethyl-4-hydroxy benzoate (0.0025 mol) in 1,4-dioxane (2.5 ml) was stirred at room temperature under $N_2$ flow. Sodium hydride (0.0033 mol) was added. The mixture was stirred for 2 minutes. Intermediate 5 (0.0028 mol) was added. The mixture was stirred for 10 minutes. 1-methyl-2-pyrrolidinone (2.5 ml) was added. The mixture was stirred at 150° C. for 12 hours, poured out into $H_2O$ and extracted with $CH_2Cl_2/CH_3OH$. The organic layer was separated, dried ($MgSO_4$), filtered and the solvent was evaporated. The residue (1.7 g) was purified by column chromatography over silica gel (eluent: $CH_2Cl_2/CH_3OH$ 92/8; 15-40 μm). The pure fractions were collected and the solvent was evaporated. Yield: 0.7 g of intermediate 10 (70%).

b-1) the Preparation of Intermediate 11

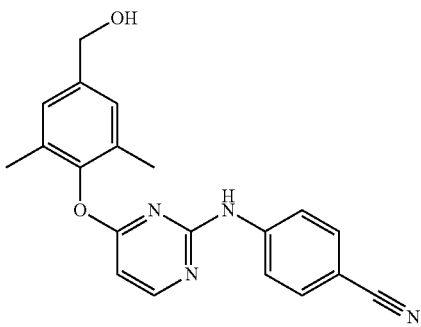 [SMILES: Cc1cc(CO)cc(C)c1Oc1ccnc(Nc2ccc(C#N)cc2)n1]

A solution of intermediate 10 (0.0005 mol) in THF (5 ml) was added dropwise at 0° C. to a suspension of $LiAlH_4$ (0.001 mol) in THF (5 ml) under $N_2$ flow. The mixture was stirred at 0° C. for 1 hour and poured out into $H_2O$ (0.5 ml). $CH_2Cl_2$ was added. The organic layer was separated, dried ($MgSO_4$), filtered, and the solvent was evaporated. The residue was purified by column chromatography over kromasil (eluent: $CH_2Cl_2$ 100 to $CH_2Cl_2/CH_3OH$ 99/1; 5 μm). The pure fractions were collected and the solvent was evaporated. The residue (0.1 g) was crystallized from diethyl ether. The precipitate was filtered off and dried. Yield: 0.043 g of intermediate 11 (24%).

b-2) the Preparation of Intermediate 37

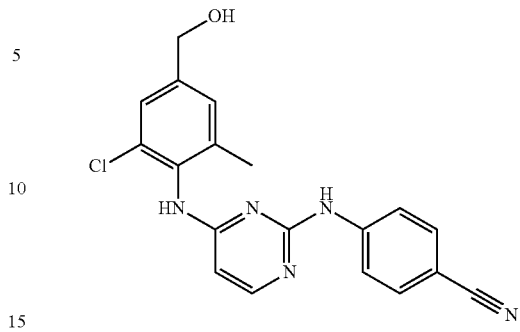

$LiAlH_4$ (0.0196 mol, 0.75 g) was added portionwise at 5° C. to a mixture of intermediate 29 (prepared according to A3d-2) (0.0098 mol) in THF (100 ml) under $N_2$ flow. The mixture was stirred at room temperature overnight, poured out into EtOAc, then into $H_2O$ and filtered over celite. The organic layer was separated, dried ($MgSO_4$), filtered, and the solvent was evaporated. Yield: 3.4 g. This fraction was purified by column chromatography over kromasil (eluent: $CH_2Cl_2/CH_3OH/NH_4OH$ 97/3/0.1; 15-40 μm). The pure fractions were collected and the solvent was evaporated. Yield 1 g (27%). This fraction was crystallized from DIPE/$CH_3CN$. The precipitate was filtered off and dried. Yield: 0.03 g of intermediate 37.

c) The Preparation of Intermediate 12

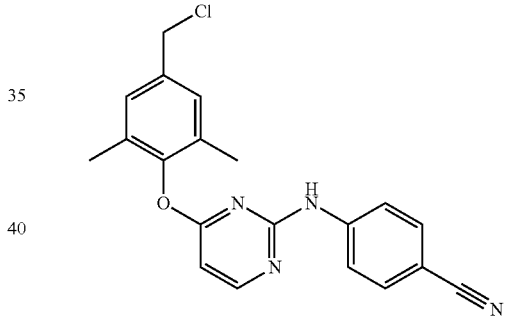

A mixture of intermediate 11 (0.0043 mol) in $CH_2Cl_2$ (50 ml) was stirred at 0° C. $SOCl_2$ (0.0206 mol) was added dropwise. The mixture was poured out into ice water/$K_2CO_3$. The mixture was stirred at room temperature for 5 minutes. The organic layer was separated, dried ($MgSO_4$), filtered, and the solvent was evaporated. Yield: 1.5 g of intermediate 12 (98%).

d) The Preparation of Intermediate 55

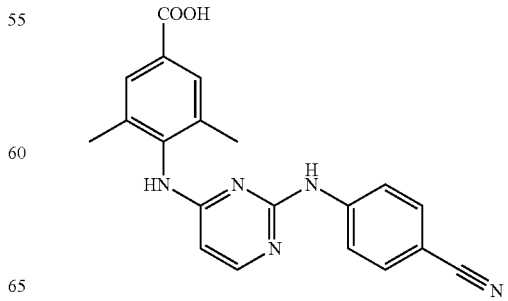

Jones's reagent (0.0084 mol) was added to a mixture of intermediate 19 (see Table 1) (prepared according to A4b-1) (0.0028 mol) in acetone (50 ml). The mixture was stirred at room temperature for 2 hours then poured out into H₂O and basified with NaHCO₃. The precipitate was filtered off and dried. Yield: 1.39 g. The residue (0.1 g) was purified by column chromatography over silica gel (eluent: CH₂Cl₂/CH₃OH/NH₄OH 85/15/1 then CH₃OH 100). The pure fraction was crystallized from isopropanol/DIPE. Yield: 0.071 g of intermediate 55.

Example A5 a) The Preparation of Intermediate 13

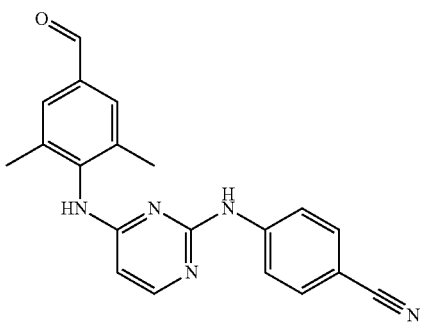 [SMILES: Cc1cc(C=O)cc(C)c1Nc1ccnc(Nc2ccc(C#N)cc2)n1]

A mixture of intermediate 19 (see Table 1) (prepared according to A4.b-1) (0.0037 mol) and MnO₂ (0.0185 mol) in CH₂Cl₂ (100 ml) was stirred at room temperature overnight, then filtered over celite. The filtrate was evaporated. Yield: 1.3 g of intermediate 13.

b) The Preparation of Intermediate 21

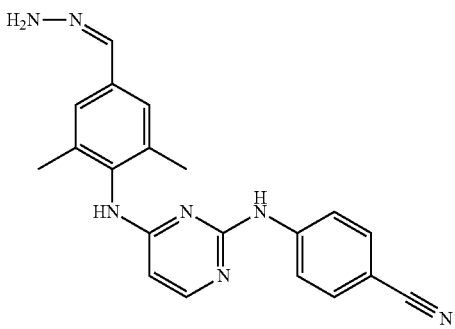 [SMILES: Cc1cc(/C=N\N)cc(C)c1Nc1ccnc(Nc2ccc(C#N)cc2)n1]

A mixture of intermediate 13 (prepared according to A5.a) (0.0029 mol) and H₂N—NH₂, H₂O (0.0058 mol) in EtOH (10 ml) was stirred at room temperature overnight. The solvent was evaporated till dryness. Yield: 0.53 g of intermediate 21.

Example A6

The Preparation of Intermediate 14

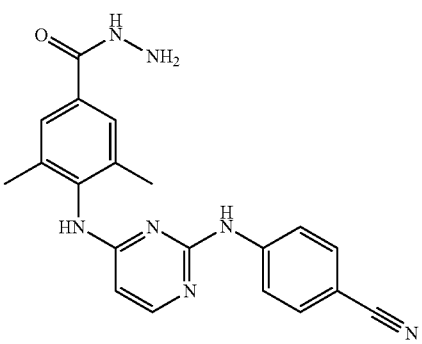 [SMILES: Cc1cc(C(=O)NN)cc(C)c1Nc1ccnc(Nc2ccc(C#N)cc2)n1]

Hydrazine (0.0077 mol) was added to a mixture of

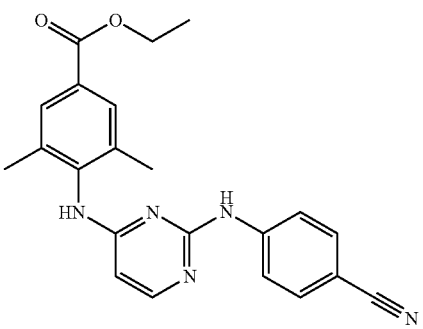 [SMILES: CCOC(=O)c1cc(C)c(Nc2ccnc(Nc3ccc(C#N)cc3)n2)c(C)c1]

(prepared according to A3.d-1) (0.0005 mol) in EtOH (10 ml). The mixture was stirred and refluxed overnight. Hydrazine (0.028 mol) was added. The mixture was stirred and refluxed overnight. Yield: 0.28 g of intermediate 14.

Example A7 a) The Preparation of Intermediate 23

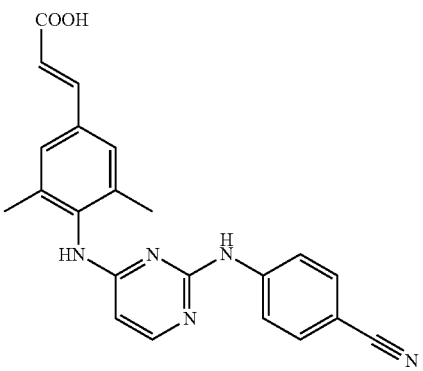 [SMILES: Cc1cc(/C=C/C(=O)O)cc(C)c1Nc1ccnc(Nc2ccc(C#N)cc2)n1]

A mixture of intermediate 35

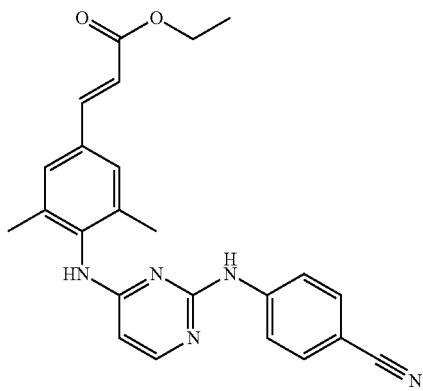 [SMILES: CCOC(=O)/C=C/c1cc(C)c(Nc2ccnc(Nc3ccc(C#N)cc3)n2)c(C)c1]

(prepared according to A3.d-1) (0.0056 mol) in HCl 3N (60 ml) and iPrOH (15 ml) was stirred and refluxed overnight. The precipitate was filtered, washed with H₂O, taken up in DIPE and dried. Yield: 2.3 g of intermediate 23 (100%).

b) The Preparation of Intermediate 56

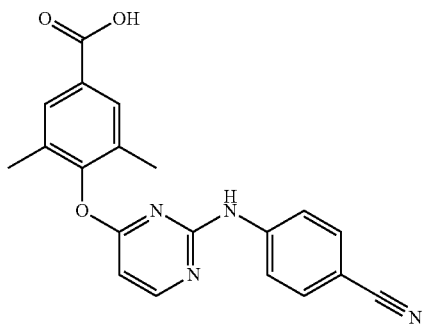 [SMILES: Cc1cc(C(=O)O)cc(C)c1Oc1ccnc(Nc2ccc(C#N)cc2)n1]

A mixture of intermediate 10 (prepared according to A4.a) (0.0012 mol) in HCl 3N (26 ml) and iPrOH (4 ml) was stirred and refluxed for 12 hours. The solvent was evaporated till dryness. The residue was taken up in (CH₃)₂CO. The solvent was evaporated. The residue was taken up in diethyl ether. The precipitate was filtered off and dried. Yield: 0.4 g (78.5%). This fraction was stirred at 60° C. for 20 minutes. Yield: 0.19 g. This fraction was crystallized from H₂O/2-propanone. The precipitate was filtered off and dried. Yield: 0.12 g of intermediate 56 (26%).

Example A8 a) The Preparation of Intermediate 24

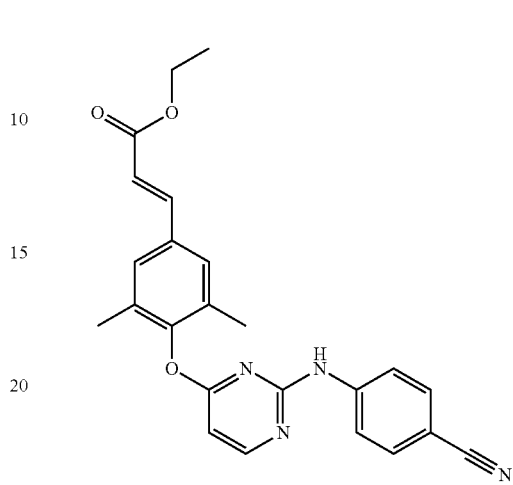

A mixture of intermediate 31 (prepared according to A4.a) (0.0005 mol) and (triphenylphosphoranylidene)acetic acid ethyl ester [CAS 1099-45-2] (0.0006 mol in THF (5 ml) was stirred at 80° C. for 48 hours, poured out into H₂O and extracted with CH₂Cl₂. The organic layer was separated, dried (MgSO₄), filtered and the solvent was evaporated. The residue (0.4 g) was crystallized from DIPE. The precipitate was filtered off and dried. Yield: 0.08 g (33%). This fraction was crystallized from DIPE/CH₃CN. The precipitate was filtered off and dried. Yield: intermediate 24 (33%).

b) The Preparation of Intermediate 25

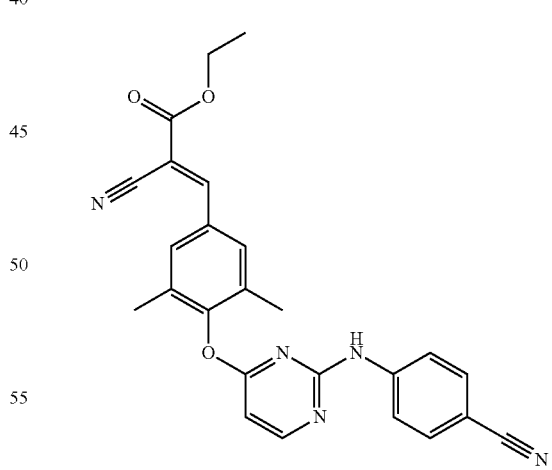

Piperidine (0.0011 mol) was added at room temperature for 30 minutes. Intermediate 31 (prepared according to A4.a) (0.0005 mol) was added. The mixture was stirred at room temperature for 1 hour, poured out into H₂O and extracted with CH₂Cl₂. The precipitate was filtered off and dried. The residue (0.2 g) was crystallized from CH₃CN/DIPE. The precipitate was filtered off and dried. Yield: 0.048 g of intermediate 25 (19%) (mp. 222° C.).

Example A9

The Preparation of Intermediate 26

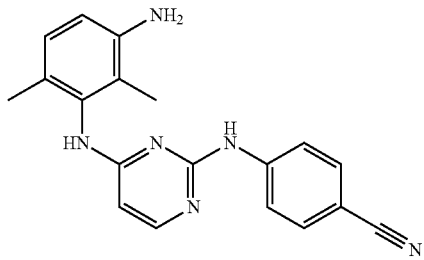 [SMILES: Cc1ccc(N)c(C)c1Nc1ccnc(Nc2ccc(C#N)cc2)n1]

A mixture of

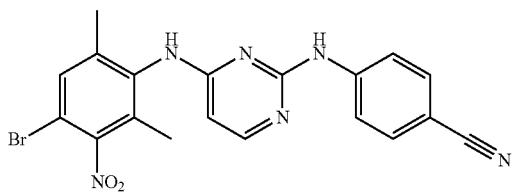

(prepared according to A3.d-1) (0.0011 mol) and Pd/C (0.2 g) in methanol (30 ml) was hydrogenated at room temperature for 2 hours under one bar pressure, then filtered over celite. Celite was washed with CH₃OH. The filtrate was evaporated till dryness. The residue (0.3 g) was crystallized from 2-propanone/CH₃OH/diethyl ether. The precipitate was filtered off and dried. Yield: 0.07 g of fraction 1. Fraction 1 was purified by column chromatography over kromasyl (eluent: CH$_2$Cl$_2$/CH$_3$OH 99.5/0.5; 5 µm). Three fractions 9F1, F2, F3) were collected and the solvent was evaporated. Yield: 0.0516 g F1, 0.1 g F2 and 0.15 g F3. F1 was taken up in diethyl ether. The precipitate was filtered off and dried. Yield: 0.028 g of intermediate 26 (8%) (mp. 272° C.).

Example A10

The Preparation of Intermediate 27

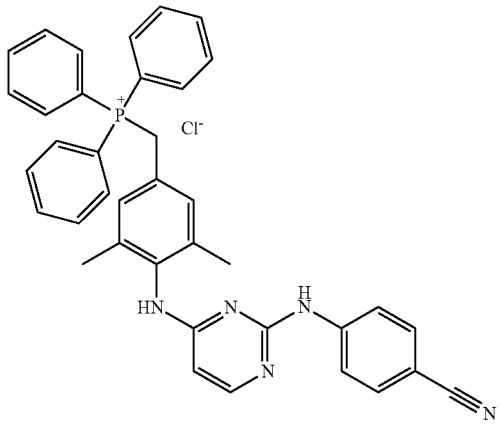

A mixture of

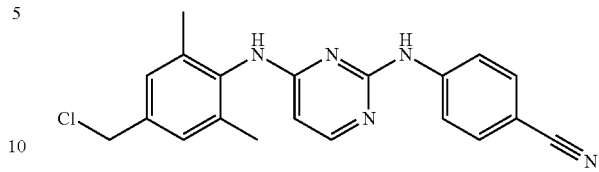

(prepared according to A4.c) (0.0005 mol) and triphenylphosphine (0.0005 mol) in CH$_3$CN (10 ml) was stirred and refluxed for a week end. The solvent was evaporated till dryness. The residue was taken up in diethyl ether. The precipitate was filtered off and dried. Yield: 0.34 g of intermediate 27 (94%).

Example A11

The Preparation of Intermediate 58

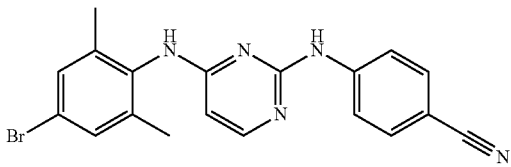 [SMILES: Cc1cc(Br)cc(C)c1Nc1ccnc(Nc2ccc(C#N)cc2)n1]

A mixture of 4-bromo-2,6-dimethylbenzenamine (0.013 mol) and intermediate 5 (0.013 mol) was stirred at 150° C. for 1 hour. The mixture was poured into K$_2$CO$_3$ 10% aqueous solution and extracted with CH$_2$Cl$_2$/MeOH (95/5). The organic layer was separated, dried (MgSO$_4$), filtered and the solvent was evaporated. The residue was crystallized from diisopropyl ether. The precipitate was filtered off and dried. Yield: 2.3 g (45%). The mother layer was purified by column chromatography over silica gel (eluent: CH$_2$Cl$_2$/CH$_3$OH—NH$_{40}$H 98.5/1.5; 15-40 µm). The pure fractions were collected and the solvent was evaporated. Yield: 0.90 g (17%). The global yield of intermediate 5 was: 3.2 g (62%).

Intermediate 59 was prepared analogously.

Intermediate 59

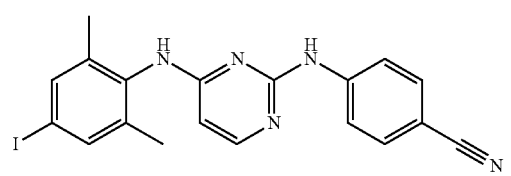

Table 1 and 2 list intermediates which intervene in the preparation of compounds of the present invention.

TABLE 1

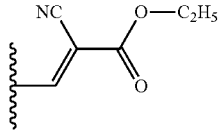 [SMILES: */C=C(\C#N)C(=O)OCC]

| Interm. No. | Ex. No. | $X_1$ | $R^3$ | $R^{4a}$ | $R^{4b}$ | Physical data |
|---|---|---|---|---|---|---|
| 11 | A4b-1 | O | —CH₂—OH | CH₃ | CH₃ | |
| 12 | A4c | O | —CH₂—Cl | CH₃ | CH₃ | |
| 16 | A3e | NH | —CH(OH)—CH₃ | CH₃ | CH₃ | |
| 17 | A3e | NH | —CH(OH)—CH(CH₃)₂ | CH₃ | CH₃ | |
| 18 | A3e | NH | —CH(OH)—CH₂—CH₃ | CH₃ | CH₃ | |
| 19 | A4b-1 | NH | —CH₂—OH | CH₃ | CH₃ | |
| 15 | A4c | NH | —CH₂—Cl | CH₃ | CH₃ | |
| 24 | A8a | O | —CH=CH—C(=O)—O—C₂H₅ | CH₃ | CH₃ | mp. 180° C.; (E) |
| 25 | A8b | O | NC, O—C₂H₅ (structure) | CH₃ | CH₃ | mp. 222° C.; (A) |
| 35 | A3d-1 | NH | —CH=CH—C(=O)—O—C₂H₅ | CH₃ | CH₃ | mp. 200° C.; (E) |
| 23 | A7a | NH | —CH=CH—COOH | CH₃ | CH₃ | |
| 34 | A3e-3 | NH | —CH(OH)—CH₃ | CH₃ | H | mp. 182° C. |
| 36 | A4b-1 | NH | —CH₂—OH | CH₃ | H | mp. 210° C. |
| 37 | A4b-2 | NH | —CH₂—OH | Cl | CH₃ | |
| 38 | A4b-1 | NH | —CH₂—OH | Cl | H | mp. 226° C. |
| 39 | A3e-1 | O | —CH(OH)—CH₃ | CH₃ | H | mp. 160° C. |
| 40 | A4b-1 | S | —CH₂—OH | CH₃ | CH₃ | mp. 173° C. |
| 41 | A4b-1 | NH | —CH₂—OH | Br | H | mp. 234° C. |
| 32 | A3e-2 | O | —CH(OH)—CH₃ | CH₃ | CH₃ | mp. 193° C. |
| 42 | A4b-1 | NH | —CH₂—OH | Br | CH₃ | mp. 250° C. |
| 43 | A4b-1 | NH | —CH₂—OH | OH | H | mp. 124° C. |
| 44 | A4b-1 | NH | —CH₂—OH | H | H | mp. 215° C. |
| 45 | A4b-1 | NH | —CH₂—OH | O—CH₃ | H | |
| 46 | A4b-1 | NH | —CH₂—OH | CF₃ | H | mp. 194° C. |
| 47 | A4c | NH | —CH₂—Cl | Cl | CH₃ | |
| 48 | A4c | NH | —CH₂—Cl | Cl | H | |
| 49 | A3e-1 | O | —CH₂—OH | CH₃ | H | |
| 50 | A4c | O | —CH₂—Cl | CH₃ | H | |
| 51 | A4b-1 | NH | —CH₂—OH | C(CH₃)₃ | H | |
| 52 | A4c | NH | —CH₂—Cl | CH₃ | H | |
| 53 | A4b-1 | NH | —CH₂—OH | 2-furanyl | CH₃ | |
| 54 | A4c | NH | —CH₂—Cl | Br | CH₃ | |
| 57 | A7b | O | —CH=CH—COOH | CH₃ | CH₃ | |

TABLE 2

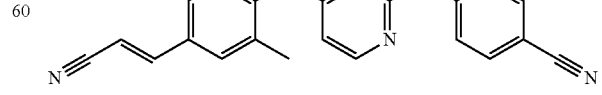

| Interm. No. | Ex. No. | $X_1$ | $R^3$ | Physical data |
|---|---|---|---|---|
| 20 | A3e | NH | —CHOH—CH₃ | |

B. Preparation of the Final Compounds

Example B1

The Preparation of Compound 1

A mixture of intermediate 3 (0.034 mol) and intermediate 5 (0.0174 mol) was stirred at 150° C. for 1 hour and taken up in K₂CO₃ 10%/CH₂Cl₂/CH₃OH. The organic layer was separated, dried (MgSO$_4$), filtered, and the solvent was evaporated. The residue (10 g) was purified by column chromatography over silica gel (eluent: CH$_2$Cl$_2$/ethyl acetate 80/20; 15-40 μm). Fraction 1 was crystallized from iPrOH. The precipitate was filtered off and dried. Yield: 1.3 g of 4-[[4-[[4-(2-cyanoethenyl)-2,6-dimethylphenyl]amino]-2-pyrimidinyl]amino]benzonitrile (E) (compound 1) (20%).

Example B1A

Compound 1 was also prepared as follows:

A mixture of 93.9 g (0.45 mol) of the hydrochloric acid salt of intermediate 3, prepared according to Example A1c), and 109 g (0.4725 mol) of intermediate 5 in 1.8 l of acetonitrile was prepared under nitrogen atmosphere. The mixture was stirred and refluxed for 69 hours, then allowed to cool to 55° C. The mixture was filtered and the residue was washed with 200 ml of acetonitrile, followed by drying under reduced pressure at 50° C. overnight. 144.6 g (0.3666 mol) of the obtained solid was brought in 1 l of K$_2$CO$_3$ 10% aqueous solution. The mixture was stirred at room temperature followed by filtration. The obtained residue was washed twice with water followed by drying at 50° C. under reduced pressure. The residue was brought in 6.55 l isopropanol and the mixture was refluxed, then stirred overnight and filtered at room temperature. The residue was was dried at 50° C. under reduced pressure. Yield: 113.2 g (68.6%) of 4-[[4-[[4-(2-cyanoethenyl)-2,6-dimethylphenyl]amino]-2-pyrimidinyl]amino]benzonitrile (E) (compound 1).

Example B1B

Alternatively, compound 1 was also prepared as follows:

a) A mixture of intermediate 58 (0.00021 mol), prepared according to Example A11, acrylonitrile (CH$_2$=CH—CN) (0.00213 mol), Pd(OAc)$_2$ (0.000043 mol), N,N-diethylethanamine (0.000043 mol) and tris(2-methylphenyl)phosphine (0.00021 mol) in CH$_3$CN (7 ml) was stirred in a sealed vessel at 150° C. overnight. H$_2$O was added. The mixture was extracted with CH$_2$Cl$_2$. The organic layer was separated, dried (MgSO$_4$), filtered and the solvent was evaporated. The residue (0.15 g) was purified by column chromatography over silica gel (eluent: CH$_2$Cl$_2$/ethyl acetate 80/20; 15-40 μm). Fraction 1 was collected and the solvent was evaporated, yielding 0.045 g of 4-[[4-[[4-(2-cyanoethenyl)-2,6-dimethylphenyl]amino]-2-pyrimidinyl]amino]benzonitrile (E/Z=80/20). The solid was crystallized from diethylether. Yield: 0.035 g of 4-[[4-[[4-(2-cyanoethenyl)-2,6-dimethylphenyl]amino]-2-pyrimidinyl]amino]benzonitrile (E) (compound 1) (55%).

b) 4.41 g (10 mmol) of intermediate 59 and 15 ml of N,N-dimethylacetamide were brought in a 100 ml flask under nitrogen. To this mixture were added 0.98 g of sodium acetate (12 mmol), 107 mg (0.1 mmol Pd) of Pd/C 10% (wet) and 1 ml (15 mmol) of acrylonitrile. The mixture was heated at 140° C. and the evolution of the reaction was followed by liquid chromatography. The reaction yielded 4-[[4-[[4-(2-cyanoethenyl)-2,6-dimethylphenyl]amino]-2-pyrimidinyl]amino]benzonitrile (E/Z=80/20) which can be converted to 4-[[4-[[4-(2-cyanoethenyl)-2,6-dimethylphenyl]amino]-2-pyrimidinyl]amino]benzonitrile (E) as described above in Example B1Ba).

Example B2 a) The Preparation of Compound 2

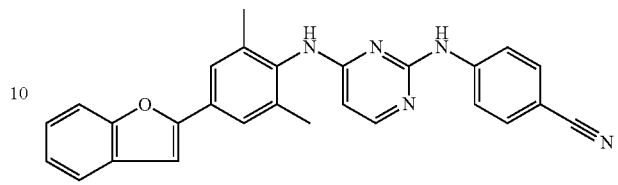

A mixture of

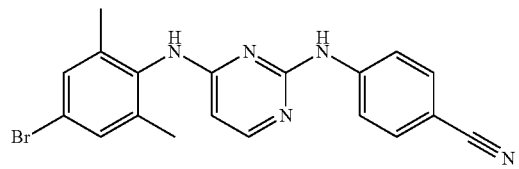 [SMILES: Cc1cc(Br)cc(C)c1Nc1ccnc(Nc2ccc(C#N)cc2)n1]

(prepared according to A3.d-1) (0.0002 mol), 2-benzofuranylboronic acid (0.0005 mol), Pd(PPh$_3$)$_4$ (0.00002 mol) and Na$_2$CO$_3$ (0.0007 mol) in DME (3 ml) was stirred and refluxed in a scelled tube for 3 hours. H$_2$O was added. The mixture was extracted with ethyl acetate. The organic layer was separated, dried (MgSO$_4$), filtered and the solvent was evaporated. The residue (0.126 g) was purified by column chromatography over silica gel (eluent: CH$_2$Cl$_2$/CH$_3$OH 98/2; 15-40 μm). The pure fractions were collected and the solvent was evaporated.

Yield: 0.011 g of compound 2 (10%).

b) The Preparation of Compound 3

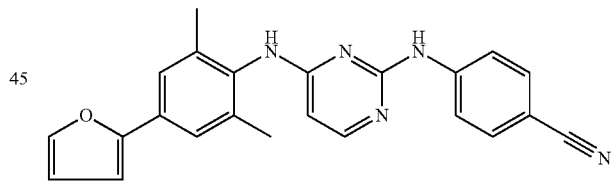

A mixture of

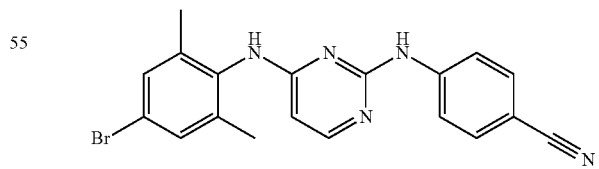

(prepared according to A3.d-1) (0.0002 mol), tributyl-2-furanylstannane (0.0005 mol) and Pd(PPh$_3$)$_4$ (0.00001 mol) in dioxane (5 ml) was stirred at 80° C. The solvent was evaporated. The residue was purified by column chromatography over silica gel (eluent: CH$_2$Cl$_2$/CH$_3$OH 98/2; 15-40 μm). The pure fractions were collected and the solvent was evaporated. The residue (0.025 g) was crystallized from DIPE. The precipitate was filtered off and dried. Yield: 0.021 g of compound 3 (22%).

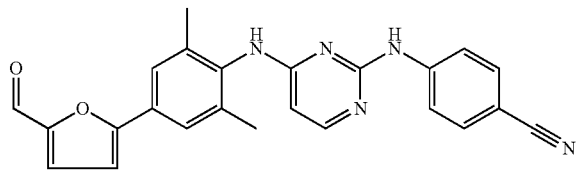 [SMILES: Cc1cc(-c2ccc(C=O)o2)cc(C)c1Nc1ccnc(Nc2ccc(C#N)cc2)n1]

c) The Preparation of Compound 104

A mixture of

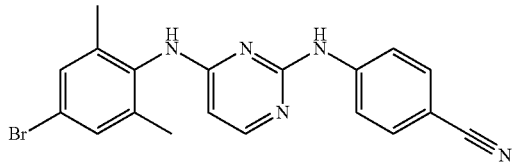 [SMILES: Cc1cc(Br)cc(C)c1Nc1ccnc(Nc2ccc(C#N)cc2)n1]

(prepared according to A3.d) (0.005 mol),

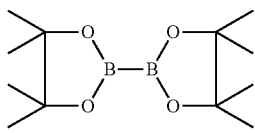

[CAS 73183-34-3] (0.0055 mol), Pd(PPh$_3$)$_4$ (0.29 g) and K$_2$CO$_3$ (2.8 g, 0.02 mol) in toluene (100 ml) and ethanol/water (5 to 10 ml) was stirred and refluxed for a weekend. 5-Bromo-furan-2-carbaldehyde (0.0055 mol) and K$_2$CO$_3$ (1.4 g, 0.01 mol) were added. The mixture was stirred and refluxed overnight. The mixture (2.25 g) was purified by column chromatography over silica gel (eluent: CH$_2$Cl$_2$/CH$_3$OH 100/0 to 99/1; 15-40 mm). The pure fractions were collected and the solvent was evaporated. Yield: 0.135 g of compound 104 (6%).

Example B3

The Preparation of Compound 4

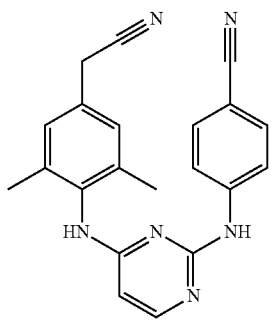 [SMILES: Cc1cc(CC#N)cc(C)c1Nc1ccnc(Nc2ccc(C#N)cc2)n1]

A mixture of intermediate 15 (see Table 1) (prepared according to A4.c) (0.0005 mol) and NaCN (0.0011 mol) in DMF (5 ml) was stirred at 80° C. overnight, poured out into H$_2$O and extracted with ethyl acetate. The organic layer was separated, dried (MgSO$_4$), filtered, and the solvent was evaporated. The residue (0.15 g) was purified by column chromatography over kromasil (eluent: CH$_2$Cl$_2$/CH$_3$OH 99/1; 10 μm). The pure fractions were collected and the solvent was evaporated. The residue (0.024 g) was purified by column chromatography over hypersil (eluent: acetonitrile/H$_2$O 52/48; 8 μm). The pure fractions were collected and the solvent was evaporated. Yield: 0.02 g of compound 4 (10%).

Example B4 a) The Preparation of Compound 5

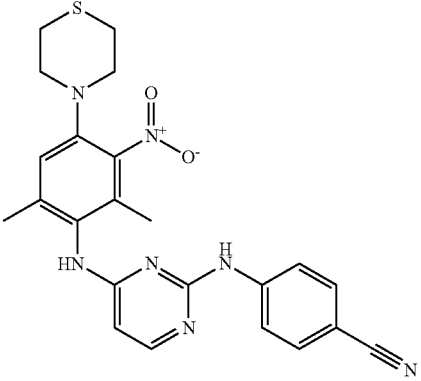 [SMILES: Cc1cc(N2CCSCC2)c([N+](=O)[O-])c(C)c1Nc1ccnc(Nc2ccc(C#N)cc2)n1]

A mixture of

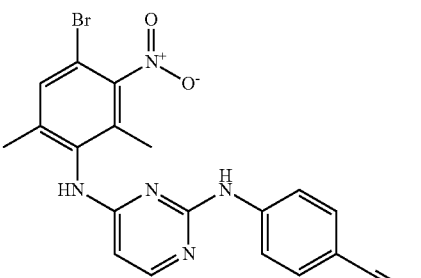

(prepared according to A3.d) (0.0006 mol) and thiomorpholine (0.5 g) was stirred at 120° C. for 48 hours, taken up in CH$_2$Cl$_2$ and the solvent was evaporated. The residue (0.44 g) was purified by column chromatography over kromasyl (eluent: CH$_2$Cl$_2$/CH$_3$OH 99/1; 10 μm). The pure fractions were collected and the solvent was evaporated. Yield: 0.06 g (20%). This fraction was crystallized from diethyl ether/2-propanone. The precipitate was filtered off and dried. Yield: 0.035 g of compound 5.

b) The Preparation of Compound 6

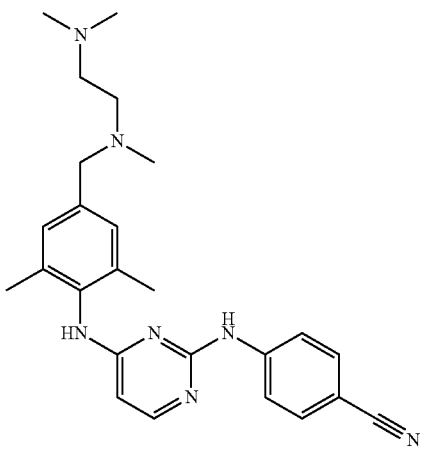 [SMILES: Cc1cc(CN(C)CCN(C)C)cc(C)c1Nc1ccnc(Nc2ccc(C#N)cc2)n1]

A mixture of intermediate 15 (see Table 1) (prepared according to A4.c) (0.000137 mol), N,N,N'-trimethyl-1,2-ethanediamine (2 equiv, 0.000275 mol) and $K_2CO_3$ (2 equiv, 0.000275 mol) in $CH_3CN$ (q.s.) was stirred at 80° C. for 12 hours. $H_2O$ was added. The mixture was extracted with $CH_2Cl_2$. The extract's solvent was evaporated. The residue was purified by chromatography. The product fractions were collected and the solvent was evaporated. Yield: 0.006 g of compound 6 (10.16%).

c) The Preparation of Compound 7

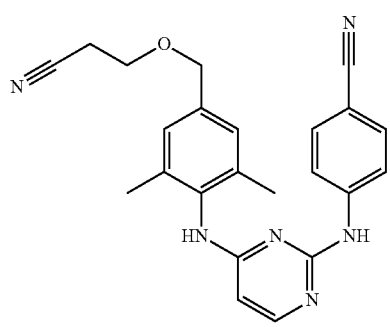 [SMILES: Cc1cc(COCCC#N)cc(C)c1Nc1ccnc(Nc2ccc(C#N)cc2)n1]

A mixture of intermediate 15 (see Table 1) (prepared according to A4.c) (0.0005 mol) in 3-hydroxy-propanenitrile (2 ml) was stirred overnight, poured out into $H_2O$ and extracted with $CH_2Cl_2$. The organic layer was separated, dried ($MgSO_4$), filtered, and the solvent was evaporated. The residue was purified by column chromatography over silica gel (eluent: $CH_2Cl_2/CH_3OH/NH_4OH$ 99/1/0.1; 15-40 μm). Two fractions (F1, F2) were collected and the solvent was evaporated. Yield: 0.034 g F1 and 0.514 g F2. F2 was washed with HCl 3N and extracted with $CH_2Cl_2$. The organic layer was separated, dried ($MgSO_4$), filtered, and the solvent was evaporated. The residue was crystallized from DIPE. The precipitate was filtered off and dried. Yield: 0.039 g of compound 7 (18%)

d) The Preparation of Compound 105

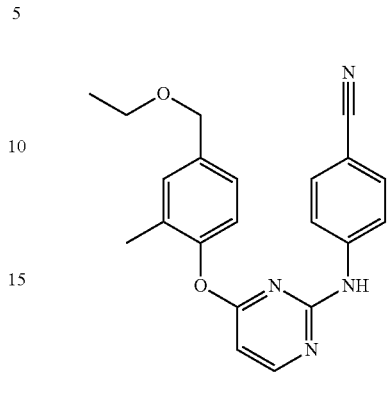

A mixture of intermediate 50 (prepared according to A4c) (0.001 mol), KCN (0.0011 mol) and KI (0.00005 mol) in EtOH (15 ml) was stirred and refluxed for 4 hours. The solvent was evaporated till dryness. The residue was taken up in $CH_2Cl_2/H_2O$. The mixture was extracted with $CH_2Cl_2$. The organic layer was separated, dried ($MgSO_4$), filtered, and the solvent was evaporated. The residue (0.31 g) was purified by column chromatography over kromasil (eluent: cyclohexane/EtOAc 70/30; 10 μm). Three fractions were collected and the solvent was evaporated. Yield: 0.044 g of fraction 1, 0.11 g of fraction 2 and 0.055 g of fraction 3. Fraction 3 was crystallized from DIPE. The precipitate was filtered off and dried. Yield: 0.046 g of compound 105 (12%) (mp. 140° C.).

Example B5 a) The Preparation of Compound 8

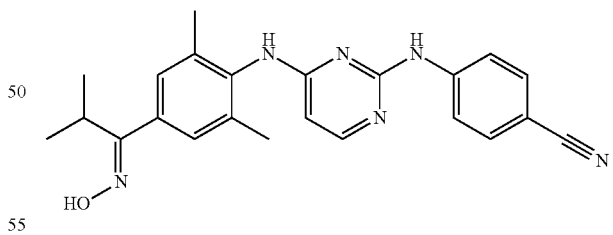

A mixture of intermediate 9 (0.0001 mol) and hydroxylamine (0.0002 mol) in EtOH (7 ml) was stirred at room temperature for 3 hours, poured out into $K_2CO_3$ 10% and extracted with $CH_2Cl_2$. The organic layer was separated, dried ($MgSO_4$), filtered and the solvent was evaporated. The residue (0.1 g) was crystallized from DIPE/$CH_3CN$. The precipitate was filtered off and dried. Yield: 0.026 g of compound 8.

b) The Preparation of Compound 9

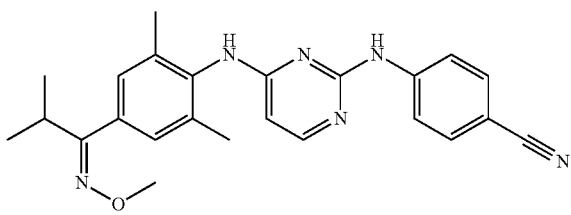 [SMILES: CO/N=C(\c1cc(C)c(Nc2ccnc(Nc3ccc(C#N)cc3)n2)c(C)c1)C(C)C]

A mixture of intermediate 9 (0.0002 mol) and O-methyl-hydroxylamine (0.0003 mol) in EtOH (10 ml) was stirred at room temperature overnight, poured out into H$_2$O and extracted with CH$_2$Cl$_2$. The organic layer was separated, dried (MgSO$_4$), filtered and the solvent was evaporated. The residue (0.13 g) was purified by column chromatography over kromasyl (eluent: cyclohexane/iPrOH/NH$_4$OH; 5 μm). The pure fractions were collected and the solvent was evaporated. The residue (0.06 g) was crystallized from DIPE. The precipitate was filtered off and dried. Yield: 0.036 g of compound 9 (34%).

Example B6 a) The Preparation of Compound 1 and 10

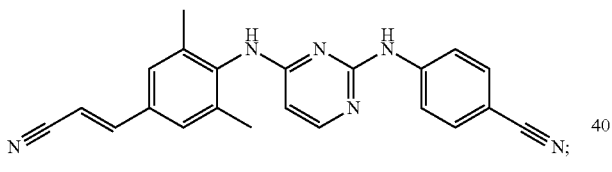

Compound 1 = (E) compound 10 = (Z)

A mixture of (cyanomethyl)triphenylphosphonium chloride (0.0022 mol) and potassium tert.-butoxide (0.0022 mol) in THF (7 ml) was stirred at 5° C. for 30 minutes under N$_2$ flow, then stirred at 5° C. for 30 minutes. A mixture of intermediate 13 (0.0015 mol) in THF (7 ml) was added. The mixture was stirred for 8 hours in darkness, poured out into H$_2$O and extracted with CH$_2$Cl$_2$. The organic layer was separated, dried (MgSO$_4$), filtered and the solvent was evaporated. The residue (1.4 g) was purified by column chromatography over silica gel (eluent: toluene/iPrOH/NH$_4$OH 96/4/0.1; 15-40 μm). Two fractions (F1, F2) were collected and the solvent was evaporated. Yield: 0.165 g of F1 (E/Z=32/68) (30%) and 0.225 g of F2 (E/Z=90/10) (41%). F2 was crystallized from CH$_3$CN/diethyl ether. Yield: 0.036 g of compound 1 (7%). F1 was purified by column chromatography over kromasyl (eluent: toluene/iPrOH 98/2; 5 μm). The pure fractions were collected and the solvent was evaporated. Yield: 0.029 g of compound 10 (5%).

b) The Preparation of Compound 11 (Z) and Compound 103 (E)

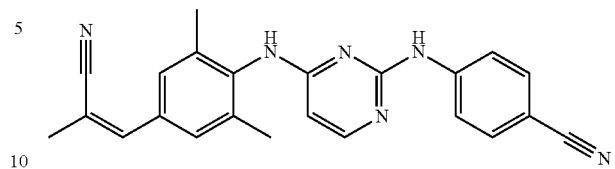

Potassium tert-tertbutoxide (0.0196 mol) was added portionwise at 5° C. to a mixture of (1-cyanoethyl)-phosphonic acid diethyl ester (0.0196 mol) in THF (25 ml) under N$_2$ flow. The mixture was stirred at 5° C. for 30 minutes, then at room temperature for 30 minutes. A solution of intermediate 13 (0.0130 mol) in THF (25 ml) was added. The mixture was stirred at room temperature overnight, poured out into H$_2$O and extracted with CH$_2$Cl$_2$. The organic layer was separated, dried (MgSO$_4$), filtered, and the solvent was evaporated. The residue (5.8 g) was purified by column chromatography over silica gel (eluent: toluene/iPrOH/NH$_4$OH 92/8/0.5; 15-40 μm). Four fractions (F1, F2, F3, F4) were collected and the solvent was evaporated. Yield: 0.21 g of F1 (mixture Z/E=90/10), 0.836 g of F2 (mixture Z/E=57/43), 0.9 g of F3 and 0.87 g of F4. F3 was crystallized from DIPE/iPrOH to give 0.7 g of compound 11 (14%). F4 was crystallized from DIPE/iPrOH to give 0.67 g of compound 103 (13%).

c) The Preparation of Compound 12 and 13

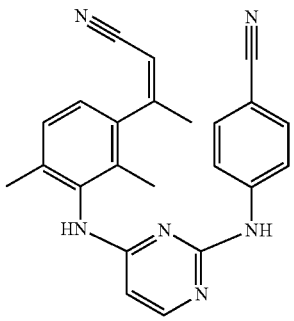

compound 12 = (E)
compound 13 = (Z)

Potassium tert.-butoxide (0.0008 mol) was added portionwise at 5° C. to a mixture of (cyanomethyl)phosphonic acid diethyl ester (0.0005 mol) in THF (20 ml) under N$_2$ flow. The mixture was stirred at room temperature for 30 minutes. A solution of

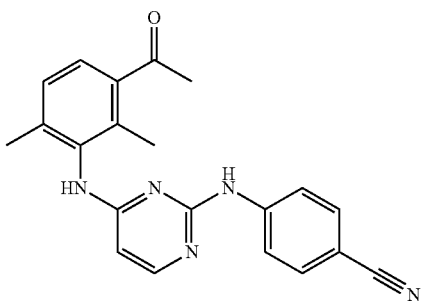 [SMILES: CC(=O)c1ccc(C)c(Nc2ccnc(Nc3ccc(C#N)cc3)n2)c1C]

(prepared according to A3.d-1) (0.0005 mol) in THF (4 ml) was added dropwise. The mixture was stirred at room temperature for 4 hours, poured out into H₂O and extracted with CH₂Cl₂. The organic layer was separated, dried (MgSO₄), filtered and the solvent was evaporated. Yield: 0.3 g. This fraction was purified by column chromatography over kromasil (eluent: CH₂Cl₂/CH₃OH 99/1; 5 μm). The pure fractions were collected and the solvent was evaporated. Yield: 0.21 g. This fraction was purified by column chromatography over kromasil (eluent: cyclohexane/ethyl acetate 50/50; 10 μm). Two fractions (F1, F2) were collected and the solvent was evaporated. Yield: 0.04 g of F1 and 0.047 g F2. F1 was dried at 70° C. for 2 hours. Yield: 0.038 g of compound 13 (18%). F2 was dried at 70° C. for 2 hours. Yield: 0.041 g of compound 12 (20%).

d) The Preparation of Compound 14

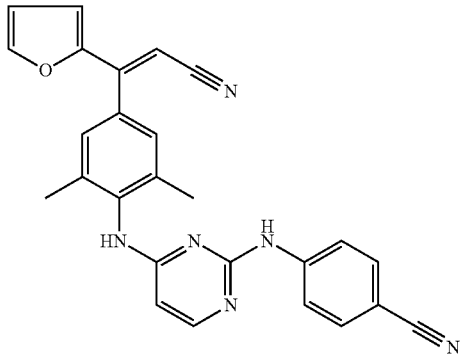 [SMILES: Cc1cc(/C(=C\C#N)c2ccco2)cc(C)c1Nc1ccnc(Nc2ccc(C#N)cc2)n1]

Potassium tert.-butoxide (0.0013 mol) was added at 5° C. to a mixture of (cyanomethyl)phosphonic acid diethyl ester (0.0013 mol) in THF (10 ml) under N₂ flow. The mixture was stirred at 5° C. for 30 minutes. A mixture of

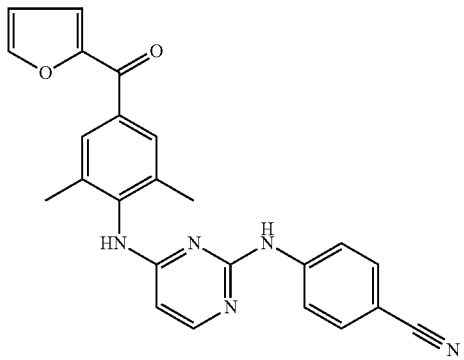 [SMILES: Cc1cc(C(=O)c2ccco2)cc(C)c1Nc1ccnc(Nc2ccc(C#N)cc2)n1]

(prepared according to A3.d-1) (0.0009 mol) in THF (10 ml) was added. The mixture was stirred at room temperature for 4 hours, poured out into H₂O and extracted with ethyl acetate. The organic layer was separated, dried (MgSO₄), filtered, and the solvent was evaporated. The residue (0.17 g) was purified by column chromatography over kromasil (eluent: CH₂Cl₂ 100 to CH₂Cl₂/CH₃OH 99/1; 5 μm). Two fractions (F1, F2) were collected and the solvent was evaporated. Yield: 0.054 g F1 and 0.05 g F2. F1 was crystallized from DIPE/CH₃CN. The precipitate was filtered off and dried. Yield: 0.046 g of compound 14 (12%).

e) The Preparation of Compound 15

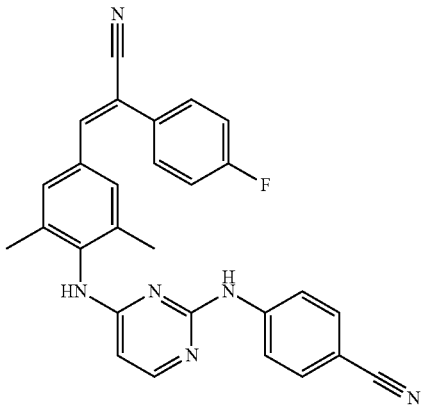 [SMILES: Cc1cc(/C=C(/C#N)c2ccc(F)cc2)cc(C)c1Nc1ccnc(Nc2ccc(C#N)cc2)n1]

4-Fluorobenzeneacetonitrile (1.2 equiv, 0.000175 ml) was added to a mixture of intermediate 13 (0.000146 mol) in CH₃OH (1 ml). NaOCH₃/CH₃OH (1.2 equiv, 0.000175 mol) was added at room temperature. The mixture was stirred at 60° C. for 2 hours, then poured out into ice-water and extracted with CH₂Cl₂. The solvent was evaporated. The residue was purified by chromatography. The product fractions were collected and the solvent was evaporated. Yield: 0.009 g of compound 15 (13.42%).

f) The Preparation of Compound 106

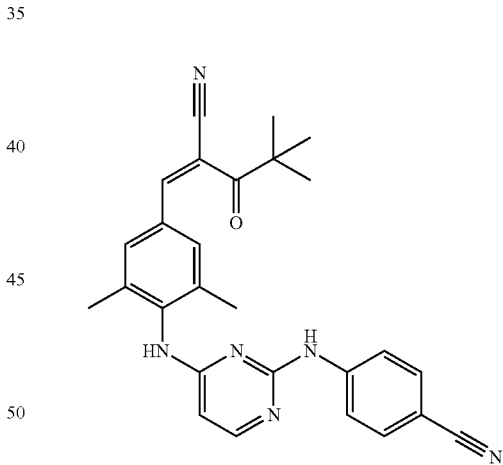

A mixture of intermediate 13 (prepared according to A5.a) (0.0005 mol) and piperidine (0.0005 mol) in ethanol (5 ml) was stirred at room temperature for 30 minutes. 4,4-dimethyl-3-oxo-pentanenitrile (0.0011 mol) was added. The mixture was stirred at room temperature overnight, poured out into H₂O and extracted with CH₂Cl₂. The organic layer was separated, dried (MgSO₄), filtered, and the solvent was evaporated. The residue (0.3 g) was purified by column chromatography over kromasil (eluent: CH₂Cl₂/CH₃OH 99/1; 10 μm). The pure fractions were collected and the solvent was evaporated. The residue (0.2 g) was crystallized from DIPE. The precipitate was filtered off and dried. Yield: 0.141 g of compound 106 (54%) (mp. 193° C.).

Example B7

The Preparation of Compound 16

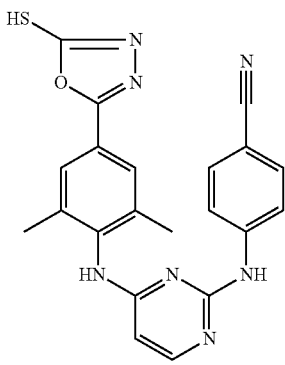 [SMILES: Cc1cc(-c2nnc(S)o2)cc(C)c1Nc1ccnc(Nc2ccc(C#N)cc2)n1]

A mixture of intermediate 14 (0.00005 mol) and carbonothioic dichloride (0.001 mol) in dioxane (10 ml) was stirred at room temperature. H₂O was added. The mixture was extracted with CH₂Cl₂. This fraction was purified by column chromatography over silica gel (eluent: CH₂Cl₂/CH₃OH/NH₄OH 90/10/0.1; 15-40 μm). The pure fractions were collected and the solvent was evaporated. Yield: 0.027 g of compound 16 (95.6%).

Example B8

The Preparation of Compound 17

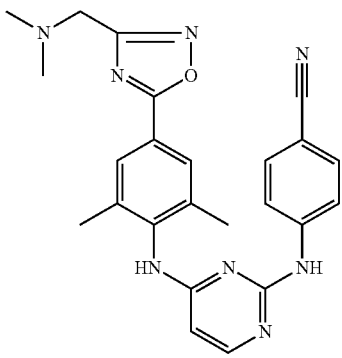 [SMILES: Cc1cc(-c2nc(CN(C)C)no2)cc(C)c1Nc1ccnc(Nc2ccc(C#N)cc2)n1]

The mixture of NaOCH₃ (0.001 mol) and 2-(dimethylamino)-N-hydroxy-ethanimidamide (0.001 mol) in EtOH (10 ml) was stirred at room temperature for 30 minutes.

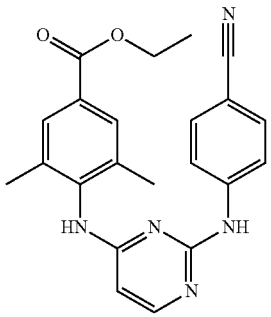 [SMILES: CCOC(=O)c1cc(C)c(Nc2ccnc(Nc3ccc(C#N)cc3)n2)c(C)c1]

(prepared according to A3.d-1) (0.0005 mol) was added. The mixture was stirred and refluxed overnight. H₂O was added. The mixture was extracted with CH₂Cl₂. The residue was purified by column chromatography over silica gel (eluent: CH₂Cl₂/CH₃OH/NH₄OH 95/5/0.1; 15-40 μm). The pure fractions were collected and the solvent was evaporated. Yield: 0.07 g of compound 17 (31%).

Example B9

The Preparation of Compound 18

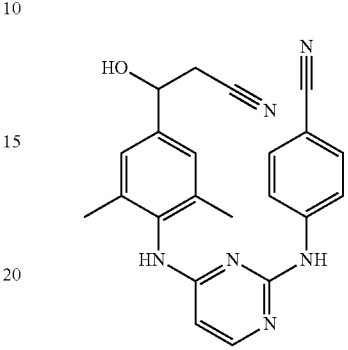

nBuLi (0.0038 mol) was added dropwise at −70° C. to a mixture of iPr₂NH (0.0038 mol) in THF (5 ml) under N₂ flow. The mixture was brought to −20° C., stirred for 30 minutes and cooled again to −70° C. A solution of CH₃CN (0.0038 mol) in THF (6 ml) was added dropwise. The mixture was brought to −20° C., stirred for 1 hour, cooled again to −70° C. A mixture of intermediate 13 (0.0009 mol) in THF (1 ml) was added. The mixture was stirred for 2 hours, poured out on ice at −30° C. and extracted with ethyl acetate. The organic layer was separated, dried (MgSO₄), filtered, and the solvent was evaporated. The residue (0.433 g) was purified by column chromatography over silica gel (eluent: CH₂Cl₂/CH₃OH 98/2; 35-70 μm). Two fractions were collected and the solvent was evaporated. Yield: 0.056 g F1 and 0.23 g F2 (78%). F1 was crystallized from DIPE/CH₃CN. The precipitate was filtered off and dried. Yield: 0.036 g of compound 18.

Example B9A a) The Preparation of Compound 107

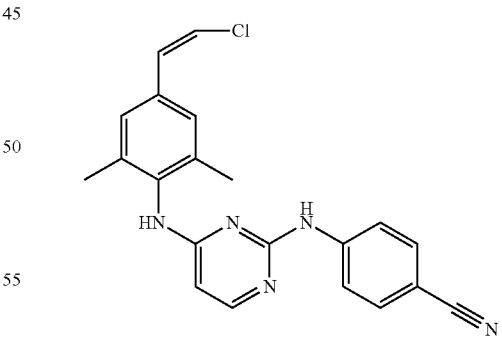

nBuLi[1.6] (0.0026 mol) was added dropwise at −70° C. to a mixture of intermediate 13 (prepared according to A5.a) (0.0008 mol) in THF (10 ml) under N₂ flow. The mixture was stirred at −70° C. for 30 minutes. A solution of (chloromethyl)triphenylphosphonium chloride (0.0026 mol) in THF (5 ml) was added dropwise. The mixture was stirred at room temperature overnight, poured out into H₂O and extracted with EtOAc. The organic layer was separated, dried (MgSO₄), filtered and the solvent was evaporated. The residue (0.7 g) was purified by column chromatography over kromasil (eluent: $CH_2Cl_2/CH_3OH$ 99/1; 10 μm). The pure fractions were collected and the solvent was evaporated. The residue (0.155 g) was purified by column chromatography over C18 (eluent: $CH_3CN/NH_4Ac$ 0.5% 60/40). The pure fractions were collected and the solvent was evaporated. The residue (0.051 g) was crystallized from DIPE. The precipitate was filtered off and dried. Yield: 0.029 g of compound 107 (9%). (mp. 250° C.)

b) The Preparation of Compound 108 and 109 compound 108

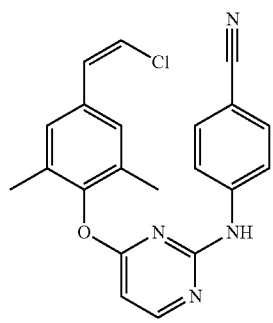

(Z)

compound 109

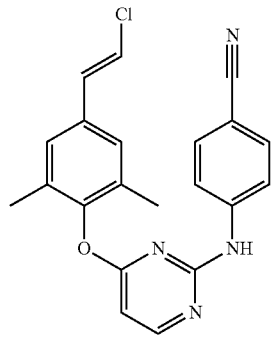

(E)

nBuLi[1.6] (0.00261 mol) was added dropwise at −70° C. to a mixture of (chloromethyl)triphenylphosphonium chloride (0.00261 mol) in THF (10 ml) under $N_2$ flow. The mixture was stirred for 30 minutes. A solution of intermediate 31 (prepared according to A4.a) (0.00087 mol) in THF (5 ml) was added dropwise. The mixture was stirred at room temperature overnight, then poured out into $H_2O$ and extracted with EtOAc. The organic layer was separated, dried ($MgSO_4$), filtered, and the solvent was evaporated. The residue (1.1 g) was purified by column chromatography over silica gel (eluent: $CH_2Cl_2/CH_3OH/NH_4OH$ 98/2/0.1; 15-40 μm). The pure fractions were collected and the solvent was evaporated. The residue (0.3 g) was purified by column chromatography over hypersil C18 (eluent: $CH_3OH/NH_4Ac$ 0.5% 70/30). Two fractions (F1, F2) were collected and the solvent was evaporated. Yield: 0.097 g F1 and 0.085 g F2. F1 was crystallized from DIPE. The precipitate was filtered off and dried.

Yield: 0.045 g of compound 108 (14%) (mp. 165° C.). F2 was crystallized from DIPE. The precipitate was filtered off and dried. Yield: 0.049 g of compound 109 (15%) (mp. 200° C.).

c) The Preparation of Compound 110

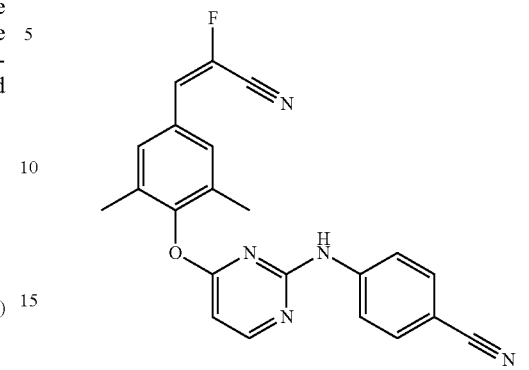

(E)

nBuLi[1.6] (1.1 ml, 0.0017 mol) was added dropwise at −70° C. to a mixture of 1,1,1,3,3,3-hexamethyldisilazane (HN(TMS)$_2$)(0.0017 mol) in THF (6 ml). The mixture was stirred at −70° C. for 30 minutes. Cyanofluoromethyl (0.0017 mol) was added. The mixture was stirred for 30 minutes. Phosphorochloridic acid diethyl ester (0.0017 mol) was added. The mixture was stirred at −70° C. for 15 minutes. nBuLi[1.6](1.1 ml, 0.0017 mol) was added dropwise. The mixture was stirred for 30 minutes. A solution of intermediate 31 (prepared according to A4.a) (0.0008 mol) in THF (4 ml) was added. The mixture was stirred at room temperature overnight, poured out into $H_2O$ and extracted with $CH_2Cl_2$. The organic layer was separated, dried ($MgSO_4$), filtered, and the solvent was evaporated. The residue (0.5 g) was purified by column chromatography over silica gel (eluent: $CH_2Cl_2$/EtOAc 95/5; 15-40 μm). Four fractions (F1, F2, F3, F4) were collected and the solvent was evaporated. Yield: 0.026 g of compound 110 (8%) (mp. 254° C.).

d) The Preparation of Compound 111

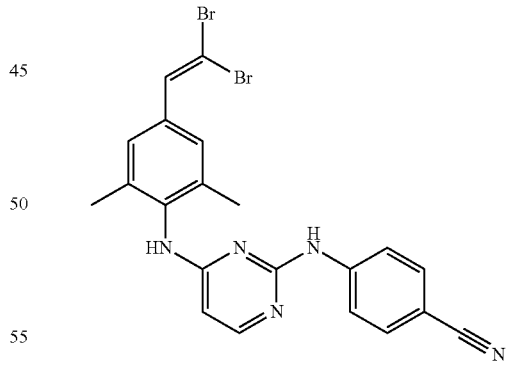

A solution of (CuCl)$_2$ (0.00015 mol) in $NH_3$ aqueous (500 μl) was added to a mixture of intermediate 21 (prepared according to A5.b) (0.0014 mol) in DMSO (1 ml). A solution of CBr$_4$ (0.0044 mol) in DMSO (1.5 ml) was added at 0° C. The mixture was stirred at room temperature overnight, poured out on ice and filtered. The organic layer was washed with $CH_2Cl_2$, dried ($MgSO_4$), filtered and the solvent was evaporated. The residue (2.73 g) was purified by column chromatography over silica gel (eluent: $CH_2Cl_2/CH_3OH$ 100/0 to 99/1; 15-40 μm). Two fractions were collected and the solvent was evaporated. Yield: 0.007 g of fraction 1 and 0.11 g of fraction 2. Fraction 2 was crystallized from DIPE. The precipitate was filtered off and dried. Yield: 0.075 g of compound 111 (mp. 223° C.).

Example B9B a) The Preparation of Compound 112

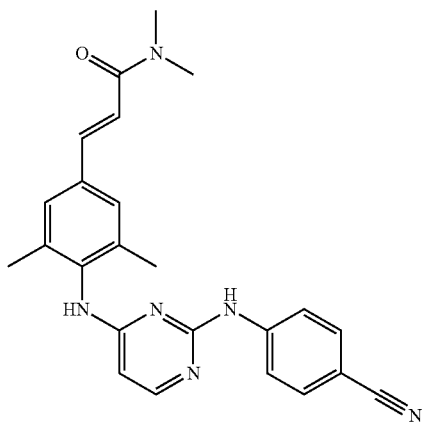

A mixture of intermediate 23 (0.0005 mol), 1-hydroxybenzotnazole 0.000 mol) and EDCI (0.0007 mol) in CH$_2$Cl$_2$ (10 ml) and THF (2 ml) was stirred. A solution of NH(CH$_3$)$_2$.HCl (0.0006 mol) and Et$_3$N (0.0005 mol) was added. The mixture was stirred at room temperature for 12 hours. H$_2$O was added. The mixture was extracted with CH$_2$Cl$_2$. The organic layer was separated, dried (MgSO$_4$), filtered, and the solvent was evaporated. The residue was purified by column chromatography over kromasil (eluent: CH$_2$Cl$_2$/CH$_3$OH 100/0 to 90/10; 5 μm). The pure fractions were collected and the solvent was evaporated. Yield: 0.124 g (58%). This fraction was purified by column chromatography over kromasil (eluent: CH$_2$Cl$_2$/CH$_3$OH 99/1; 5 μm). The pure fractions were collected and the solvent was evaporated. Yield: 0.045 g of compound 112 (21%) (mp.>264° C.).

b) The Preparation of Compound 113

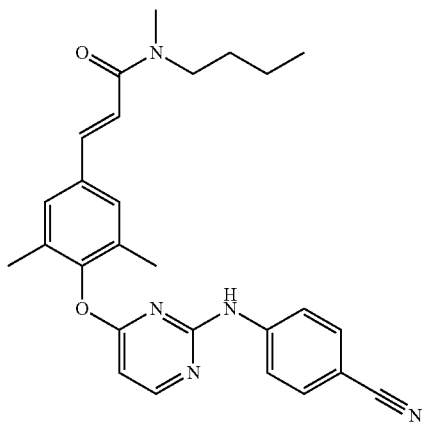

A mixture of intermediate 57 (prepared according to A7.b) (0.0002 mol), 1-hydroxybenzotriazole (0.0003 mol) and EDCI (0.0003 mol) in CH$_2$Cl$_2$ (10 ml) was stirred. N-methyl-1-butanamine [CAS 110-68-9] (0.0002 mol) was added. The mixture was stirred at room temperature for 12 hours. H$_2$O was added. The mixture was extracted with CH$_2$Cl$_2$. The organic layer was separated, dried (MgSO$_4$), filtered, and the solvent was evaporated. Yield: 0.149 g. This fraction was purified by column chromatography over kromasil (eluent: CH$_2$Cl$_2$/CH$_3$OH 100/0 to 90/10; 5 μm). The pure fractions were collected and the solvent was evaporated. Yield: 0.065 g. This fraction was taken up in DIPE. The precipitate was filtered off and dried. Yield: 0.035 g of compound 113 (30%) (mp. 212° C.).

c) The Preparation of Compound 114

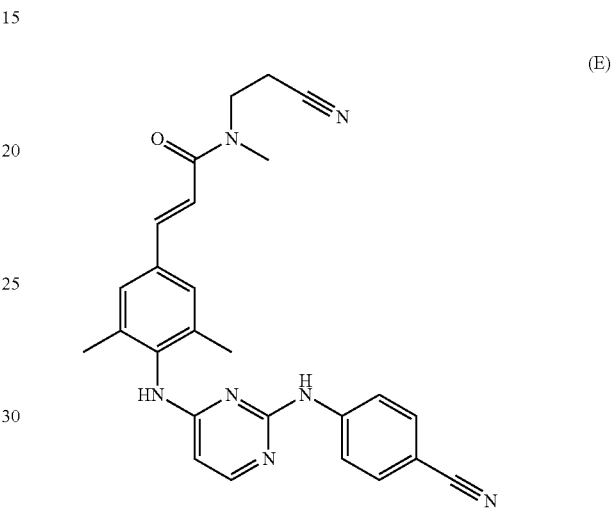

A mixture of intermediate 23 (prepared according A7.a) (0.0005 mol), 1-hydroxybenzotriazole (0.0007 mol) and EDCI (0.0007 mol) in CH$_2$Cl$_2$ (10 ml) and THF (2 ml) was stirred. 3-(methylamino)propanenitrile (0.0006 mol) was added. The mixture was stirred at room temperature for 12 hours. H$_2$O was added. The mixture was extracted with CH$_2$Cl$_2$. The organic layer was separated, dried (MgSO$_4$), filtered, and the solvent was evaporated. The residue was purified by column chromatography over kromasil (eluent: CH$_2$Cl$_2$/CH$_3$OH 100/0 to 90/10; 5 μm). The pure fractions were collected and the solvent was evaporated. Yield: 0.068 g. This fraction was crystallized from DIPE. The precipitate was filtered off and dried. Yield: 0.032 g of compound 114 (14%) (mp. 168° C.).

d) The Preparation of Compound 115

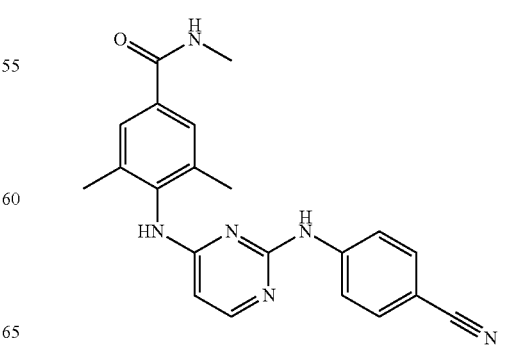

A mixture of

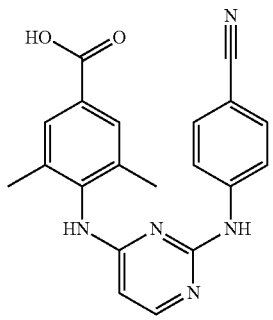 [SMILES: Cc1cc(C(=O)O)cc(C)c1Nc1ccnc(Nc2ccc(C#N)cc2)n1]

(0.000195 mol) and methylamine (2 equiv, 0.000390 mol) in THF (5 ml) and Et$_3$N (0.054 ml) was stirred at room temperature. EDCI (2 equiv, 0.000390 mol) and 1-hydroxybenzotriazole (2 equiv, 0.000390 mol) were added. The reaction mixture was stirred at room temperature for 12 hours and taken up into H$_2$O. The organic layer was separated, dried, filtered and the solvent evaporated. The product was isolated and purified by column chromatography. Yield: 0.026 g of compound 115 (17.92%).

Example B9C

The Preparation of Compound 116

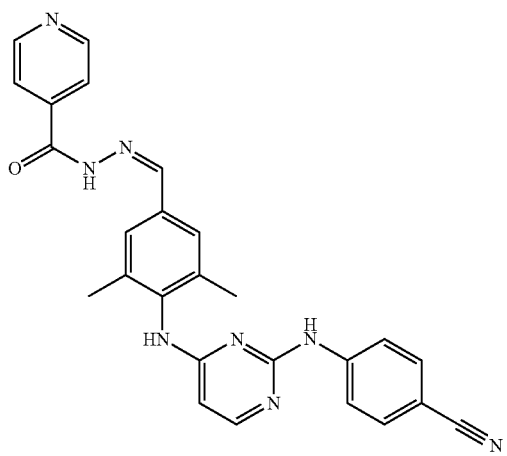 [SMILES: Cc1cc(/C=N\NC(=O)c2ccncc2)cc(C)c1Nc1ccnc(Nc2ccc(C#N)cc2)n1]

A mixture of intermediate 13 (prepared according to A5.a) (0.000291 mol) and isonicotinic acid hydrazide (2.5 equiv., 0.000728 mol) in ethanol (1 ml) and CH$_2$Cl$_2$ (2 ml) was stirred and refluxed for 12 hours. The solvent was evaporated till dryness. The residue was purified by chromatography. Yield: 0.033 g of compound 116 (24.50%).

Example B9D a) The Preparation of Compound 117

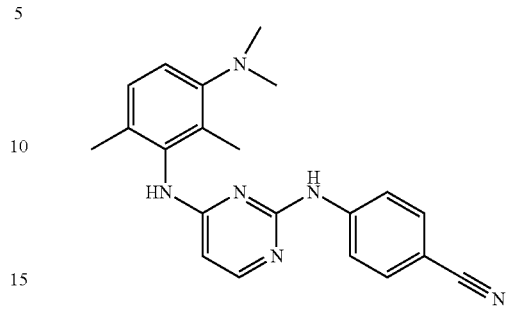

Sodium cyanoborohydride (0.0024 mol) was added at room temperature to a solution of intermediate 26 (prepared according to A9) (0.0008 mol) in formaldehyde (0.5 ml) and CH$_3$CN (20 ml) under N$_2$ flow. Acetic acid (0.5 ml) was added. The mixture was stirred at room temperature for 2 hours, poured out into H$_2$O/K$_2$CO$_3$ 10% and extracted with CH$_2$Cl$_2$. The organic layer was separated, dried (MgSO$_4$), filtered, and the solvent was evaporated. The residue (0.3 g) was purified by column chromatography over hypersol (eluent: CH$_2$Cl$_2$/CH$_3$OH 97/3; 5 μm). The pure fractions were collected and the solvent was evaporated. Yield: 0.08 g (28%). This fraction was crystallized from 2-propanone/diethyl ether. The precipitate was filtered off and dried. Yield: 0.012 g of compound 117 (5%) (mp. 132° C.).

b) The Preparation of Compound 118

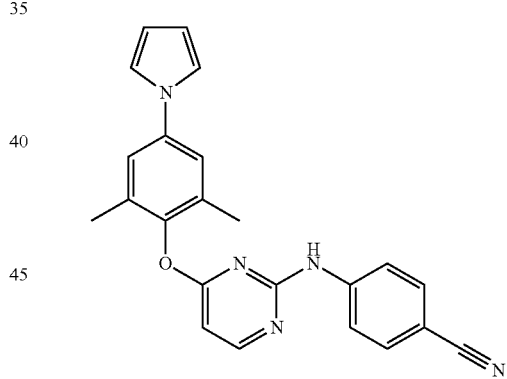

A mixture of

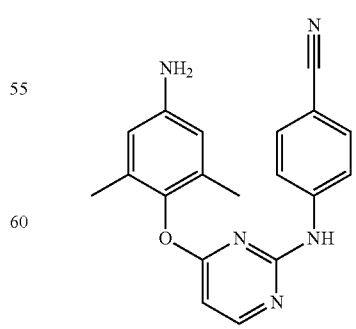

(prepared according to A9) (0.0015 mol) and tetrahydro-2,5-dimethoxyfuran (0.0077 mol) in acetic acid (10 ml) was stirred and refluxed for 1 hour, then poured out into ice water and K$_2$CO$_3$ and extracted with CH$_2$Cl$_2$. The organic layer was separated, dried (MgSO$_4$), filtered, and the solvent was evaporated. The residue (1 g) was purified by column chromatography over silica gel (eluent: cyclohexane/EtOAc 95/5; 15-40 μm). The pure fractions were collected and the solvent was evaporated. Yield: 0.23 g. This fraction was crystallized from DIPE/diethyl ether. The precipitate was filtered off and dried. Yield: 0.075 g. This fraction was crystallized again from DIPE/diethyl ether. The precipitate was filtered off and dried. Yield: 0.027 g of compound 118 (5%).

Example B9E a) The Preparation of Compound 119

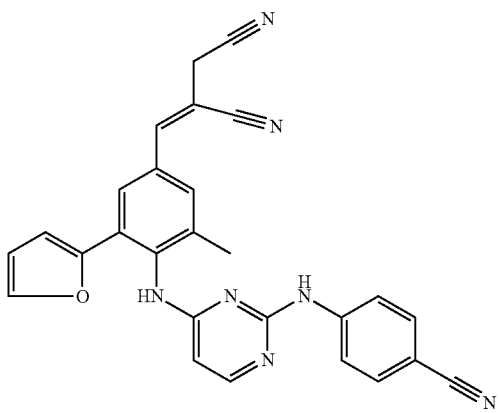 [SMILES: Cc1cc(/C=C(\C#N)CC#N)cc(-c2ccco2)c1Nc1ccnc(Nc2ccc(C#N)cc2)n1]

Tributylphoshine (0.0015 mol) was added to a mixture of but-2-enedinitrile (0.0015 mol) in THF (8 ml). The mixture was stirred and refluxed for 2 hours.

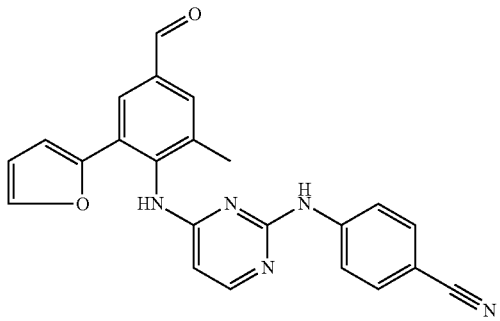 [SMILES: Cc1cc(C=O)cc(-c2ccco2)c1Nc1ccnc(Nc2ccc(C#N)cc2)n1]

prepared according to A5.a) (0.0005 mol) was added. The mixture was stirred and refluxed overnight. H$_2$O was added. The mixture was extracted with CH$_2$Cl$_2$. The organic layer was separated, dried (MgSO$_4$), filtered and the solvent was evaporated. The residue (0.618 g) was purified by column chromatography over kromasil (eluent: CH$_2$Cl$_2$ 100; 10 μm). Two fractions were collected and the solvent was evaporated. Yield: 0.03 g of compound 119 (13%).

b) The Preparation of Compound 120

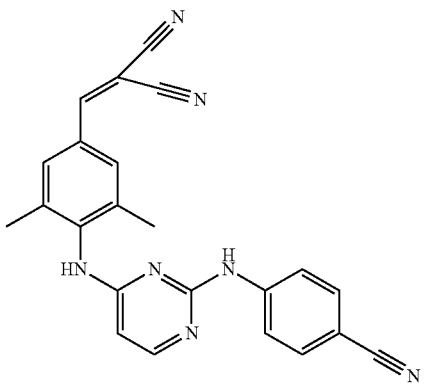 [SMILES: Cc1cc(C=C(C#N)C#N)cc(C)c1Nc1ccnc(Nc2ccc(C#N)cc2)n1]

Intermediate 13 (prepared according to A5.a) (0.002 mol) was added to a mixture of propanedinitrile (0.004 mol) and piperidine (0.004 mol) in ethanol (10 ml). The mixture was stirred at room temperature for 5 minutes. The solvent was evaporated. The residue was taken up in CH$_2$Cl$_2$ and purified by column chromatography over silica gel (eluent: CH$_2$Cl$_2$/CH$_3$OH 98/2; 15-40 μm). The pure fractions were collected and the solvent was evaporated. Yield: 0.6 g of compound 120.

Example B9F

The Preparation of Compound 122

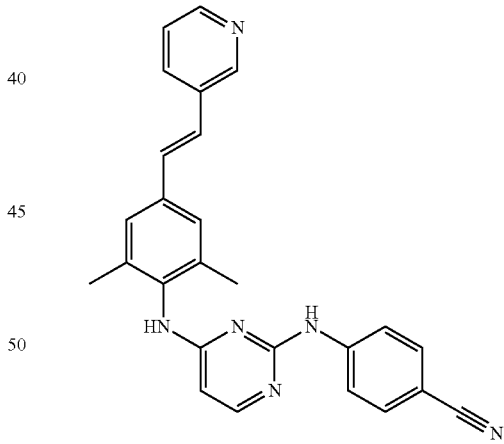

nBuLi [1.6 M] (0.0016 mol) was added dropwise at −78° C. to a mixture of intermediate 27 (prepared according to A10) (0.0004 mol) in THF (10 ml) under N$_2$ flow. The mixture was stirred at −78° C. for 1 hour, then brought to room temperature, stirred for 30 minutes and cooled to −78° C. A solution of 2-pyridinecarboxaldehyde (0.0004 mol) in THF (10 ml) was added. The mixture was stirred at room temperature for 2 hours, poured out on ice and extracted with EtOAc. The organic layer was separated, dried (MgSO$_4$), filtered, and the solvent was evaporated. The residue (0.32 g) was purified by column chromatography over silica gel (eluent: CH$_2$Cl$_2$/CH$_3$OH/NH$_4$OH 98/2/0.1;

10 µm). Two fractions were collected and the solvent was evaporated. Yield: 0.021 g of compound 122 (10.4%) (mp. 120° C.).

Example B10

The Preparation of Compound 20

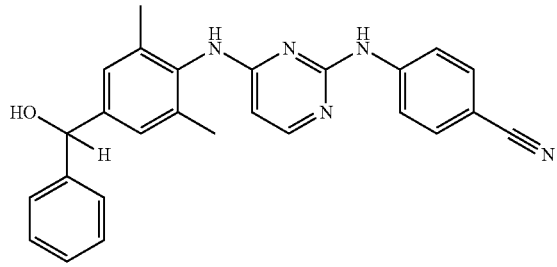 [SMILES: Cc1cc(C(O)c2ccccc2)cc(C)c1Nc1ccnc(Nc2ccc(C#N)cc2)n1]

NaBH₄ (0.0015 mol) was added portionwise at 5° C. to a mixture of compound 19 (see table 3) (prepared according to B1) (0.0014 mol) in CH₃OH (15 ml) under N₂ flow.

The mixture was stirred at 5° C. for 1 hour, poured out into H₂O and extracted with CH₂Cl₂. The organic layer was separated, dried (MgSO₄), filtered, and the solvent was evaporated. The residue (0.15 g) was purified by column chromatography over silica gel (eluent: CH₂Cl₂/CH₃OH 99/1; 10 µm). The pure fractions were collected and the solvent was evaporated. The residue (0.068 g, 12%) was crystallized from DIPE. The precipitate was filtered off and dried. Yield: 0.032 g of compound 20.

Example B11

The Preparation of Compound 21

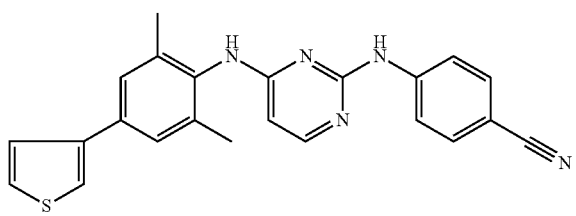 [SMILES: Cc1cc(-c2ccsc2)cc(C)c1Nc1ccnc(Nc2ccc(C#N)cc2)n1]

A mixture of compound 2 (see table 3) (0.0002 mol), 3-thienylboronic acid (0.0005 mol), Pd(PPh₃)₄ (0.00002 mol) and Na₂CO₃ (0.0007 mol) in DME (3 ml) was stirred and refluxed in a scelled tube for 3 hours. H₂O was added. The mixture was extracted with ethyl acetate. The organic layer was separated, dried (MgSO₄), filtered, and the solvent was evaporated. The residue was purified by column chromatography over silica gel (eluent: CH₂Cl₂/CH₃OH 98/2; 15-40 µm). The pure fractions were collected and the solvent was evaporated. Yield: 0.04 g of compound 21 (40%).

Example B12

The Preparation of Compound 23

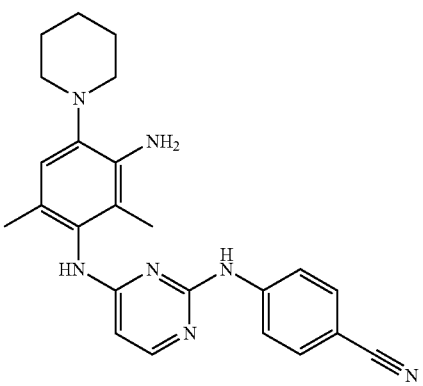

A mixture of compound 22 (see table 3) (prepared according to B4.a) (0.0002 mol) and Raney Nickel (0.1 g) in CH₃OH (10 ml) was stirred at room temperature for 15 minutes under a 2 bar pression of H₂, then filtered over celite. Celite was washed with CH₃OH. The filtrate was evaporated. Yield: 0.48 g. This fraction was purified by column chromatography over kromasyl (eluent: CH₂Cl₂/CH₃OH 99/1; 15-40 µm). Two fractions (F1, F2) were collected and the solvent was evaporated. Yield: 0.13 g F1 and 0.13 g F2. F2 was crystallized from diethyl ether. The precipitate was filtered off and dried. Yield: 0.09 g of compound 23 (20%).

Example B13

The Preparation of Compound 24

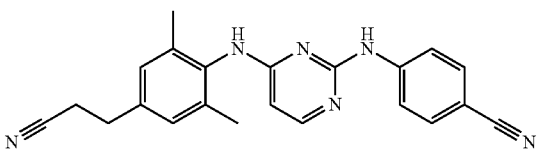 [SMILES: Cc1cc(CCC#N)cc(C)c1Nc1ccnc(Nc2ccc(C#N)cc2)n1]

A mixture of compound 1 (0.0004 mol) and Pd/C (0.07 g) in CH₃OH (10 ml) was hydrogenated at room temperature for 5 hours under a 3 bar pressure of H₂, then filtered over celite, washed with CH₂Cl₂ and the solvent was evaporated till dryness. The residue was crystallized from DIPE. The precipitate was filtered off and dried. The residue (0.7 g) was purified by column chromatography over kromasyl (eluent: CH₂Cl₂/CH₃OH 100/0 to 99/1; 5 µm). The pure fractions were collected and the solvent was evaporated. The residue (0.06 g) was crystallized from DIPE. The precipitate was filtered off and dried. Yield: 0.04 g of compound 24 (27%).

Example B14

The Preparation of Compound 26

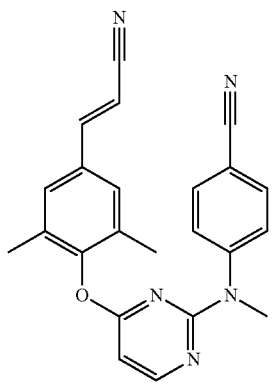

NaH 60% (0.0004 mol) was added at room temperature to a mixture of compound 25 (see Table 4) (prepared according to B6.c) (0.0004 mol) in THF (30 ml). The mixture was stirred at room temperature for 1 hour. A solution of ICH₃ (0.0004 mol) in THF (30 ml) was added. The mixture was stirred at 60° C. for 2 hours, then cooled, poured out into H₂O and extracted with CH₂Cl₂. The organic layer was separated, dried (MgSO₄), filtered and the solvent was evaporated. The residue (0.12 g) was purified by column chromatography over kromasil (eluent: CH₂Cl₂/CH₃OH 99/1; 10 μm). The pure fractions were collected and the solvent was evaporated. Yield: 0.049 g of compound 26 (32%).

Example B15 a) The Preparation of Compound 123

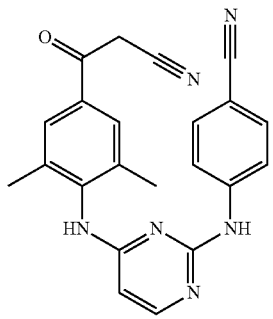 [SMILES: Cc1cc(C(=O)CC#N)cc(C)c1Nc1ccnc(Nc2ccc(C#N)cc2)n1]

Jones's reagent (0.0056 mol) was added at 5° C. to a mixture of compound 18 (prepared according to B9) (0.0029 mol) in 2-propanone (20 ml) under N₂ flow. The mixture was stirred at 5° C. for 2 hours, then poured out into H₂O, basified with NaHCO₃ and extracted with CH₂Cl₂. The organic layer was separated, dried (MgSO₄), filtered, and the solvent was evaporated. The residue (1.5 g) was purified by column chromatography over silica gel (eluent: CH₂Cl₂/CH₃OH/NH₄OH 98/2/0.1; 15-40 μm). Two fractions (F1, F2) were collected and the solvent was evaporated. Yield: 0.122 g F1 (11%) and 0.19 g F2 (17%). F2 was crystallized from DIPE. The precipitate was filtered off and dried. Yield: 0.034 g of compound 123 (mp. 150° C.).

b) The Preparation of Compound 124

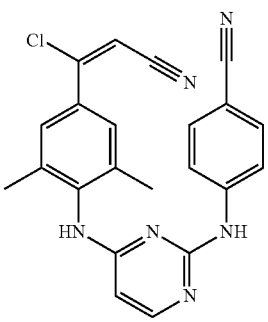 [SMILES: Cc1cc(/C(Cl)=C\C#N)cc(C)c1Nc1ccnc(Nc2ccc(C#N)cc2)n1]

A mixture of compound 123 (0.0005 mol) in POCl₃ (1.5 ml) was stirred at 80° C. for 24 hours, poured out into ice and K₂CO₃ 10% and extracted with CH₂Cl₂/CH₃OH. The organic layer was separated, dried (MgSO₄), filtered and the solvent was evaporated. The residue (0.14 g) was purified by column chromatography over kromasil (eluent: CH₂Cl₂/CH₃OH 99/1; 10 μm). The pure fractions were collected and the solvent was evaporated. Yield: 0.026 g of compound 124.

Example B16 a) The Preparation of Compound 125

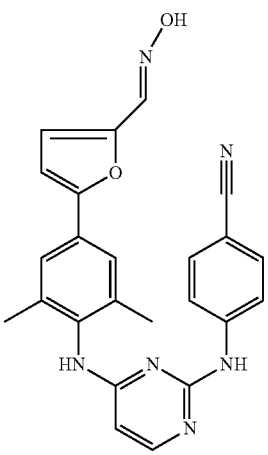 [SMILES: Cc1cc(-c2ccc(/C=N/O)o2)cc(C)c1Nc1ccnc(Nc2ccc(C#N)cc2)n1]

NaOH 5N (2 ml) was added dropwise at 50° C. to a mixture of compound 104 (see Table 3) (prepared according to B2.c) (0.0003 mol) and NH₂OH, HCl (0.0004 mol) in ethanol (10 ml). The mixture was stirred at 50° C. for 2 hours. Two-third of the mixture was evaporated. The mixture was poured out into H₂O and extracted with CH₂Cl₂. The organic layer was washed with K₂CO₃ 10%, dried (MgSO₄), filtered, and the solvent was evaporated. Yield: 0.21 g of compound 125.

b) The Preparation of Compound 126

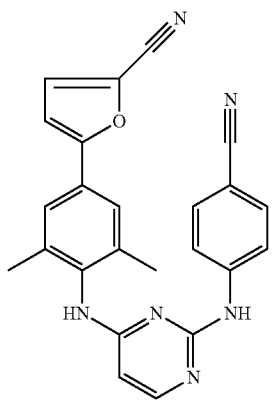 [SMILES: Cc1cc(-c2ccc(C#N)o2)cc(C)c1Nc1ccnc(Nc2ccc(C#N)cc2)n1]

1,1'-carbonyldiimidazole (0.0012 mol) was added to a mixture of compound 125 (0.0003 mol) in THF (20 ml). The mixture was stirred and refluxed overnight, poured out into H₂O and extracted with CH₂Cl₂. The organic layer was separated, dried (MgSO₄), filtered, and the solvent was evaporated. The residue (0.17 g) was purified by column chromatography over kromasil (eluent: CH₂Cl₂/CH₃OH 98/2; 10 μm). Two fractions were collected and the solvent was evaporated. Yield: 0.035 g of fraction 1 and 0.05 g of fraction 2. Both fractions were mixed and crystallized from diethyl ether. The precipitate was filtered off and dried. Yield: 0.05 g of compound 126 (38%) (mp.>260° C.).

Example B17

Preparation of Compound 253

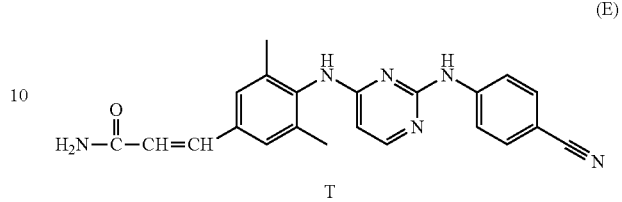

(E)

T a) 2.53 ml of acetonitrile, 0.056 g (0.253 mmol) of Pd(OAc)₂ and 0.154 g (0.506 mmol) of tris(2-methylphenyl)phosphine were brought in a 100 ml flask under nitrogen and the mixture was stirred for 10 minutes. To the mixture was added 1 g (2.53 mmol) of intermediate 58, 0.51 ml (3.8 mmol) of N,N-diethylethanamine and 0.36 g (5.06 mmol) of acrylamide. The mixture was heated at reflux (80° C.) for 5 days yielding 28% of compound 253.

b) In a 100 ml flask under N₂ were introduced 0.8 g (4.33 mmol; 1 eq.) of intermediate 3a (E), 1 g (4.33 mmom; 1 eq.) of intermediate 5 and 16 ml of 2-propanol. To this mixture 0.72 ml of HCl 6N in 2-propanol were added. The mixture was stirred under refluxed for 72 hours and then cooled yielding the hydrochloric acid salt of compound 253, i.e. compound 254.

Compound 254 can be converted into the free base according to art-known methodologies (see also Example B1A).

Compound 253 can be converted into compound 1 according to the method described above in Example A1c) y).

The following Tables 3, 4 and 5 list compounds of formula (I) as prepared according to one of the above examples (Ex. No.).

TABLE 3

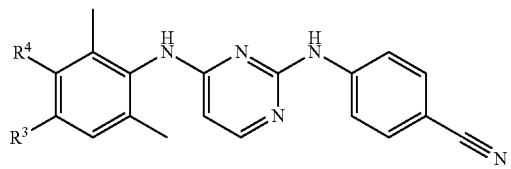

| Comp No. | Ex. No. | R³ | R⁴ | Physical data m.p. ° C./ (MH+)* |
|---|---|---|---|---|
| 2 | B2a | 2-benzofuranyl | H | mp. >240 |
| 21 | B11 | 3-thienyl | H | mp. 220 |
| 3 | B2b | 2-furanyl | H | mp. 228 |
| 28 | B2a | 2-thienyl | H | mp. 235 |
| 29 | B2a | phenyl | H | mp. 230 |
| 1 | B1/B6a | —CH=CH—CN | H | mp. 245, (E) |
| 30 | B2a | 2,4-dichlorpphenyl | H | (460) |
| 31 | B2a | 2-benzo[b]thienyl | H | (448) |
| 32 | B2a | 1-naphthalenyl | H | (442) |
| 33 | B2a | 3-chlorophenyl | H | (426) |
| 34 | B2a | 3-acetylphenyl | H | (434) |
| 35 | B2a | 3-methylphenyl | H | (406) |
| 36 | B2a | 2-naphthalenyl | H | (442) |
| 37 | B2a | 4-chlorophenyl | H | (426) |
| 38 | B2a | 4-methoxyphenyl | H | (422) |
| 39 | B2a | 4-methylthiophenyl | H | (438) |

TABLE 3-continued

[Structure: R⁴ and R³ substituted dimethylphenyl-NH-pyrimidine-NH-phenyl-CN]

| Comp No. | Ex. No. | R³ | R⁴ | Physical data m.p. °C./ (MH+)* |
|---|---|---|---|---|
| 40 | B2a | 4-(CH₂OH)-phenyl | H | |
| 19 | B1 | C(=O)-phenyl (benzoyl) | H | mp. 220 |
| 8 | B5a | —C(=N—OH)—CH(CH₃)₂ | H | mp. 156 |
| 20 | B10 | CH(OH)-phenyl | H | mp. 205 |
| 27 | B1 | C(=O)-CH₂-phenyl | H | mp. 193 |
| 41 | B10 | CH(OH)-CH₂-phenyl | H | mp. 200 |
| 42 | B5a | C(=N-OH)-CH₂-phenyl | H | mp. 155 |
| 43 | B4b | CH₂-piperidinyl | H | mp. 110 |
| 44 | B5b | CH(N-O-CH₃)-CH₂-phenyl | H | mp. 110 |
| 45 | B5a | —C(=N—OH)—CH₃ | H | mp. 135 |
| 9 | B5b | —C(=N—O—CH₃)—CH(CH₃)₂ | H | mp. 185 |
| 46 | B5b | C(=N-O-CH₂-phenyl)-CH(CH₃)₂ | H | mp. 164 |

TABLE 3-continued
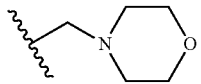 [SMILES: *CN1CCOCC1]
| Comp No. | Ex. No. | R³ | R⁴ | Physical data m.p. ° C./ (MH+)* |
|---|---|---|---|---|
| 47 | B4b | —CH₂—N(CH₂—CH₃)₂ | H | mp. 150 |
| 48 | B4b | 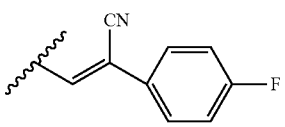 [SMILES: */C=C(\C#N)c1ccc(F)cc1] | H | mp. 85 |
| 15 | B6e | 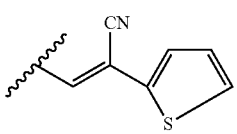 [SMILES: */C=C(\C#N)c1cccs1] | H | (461) |
| 49 | B6e | 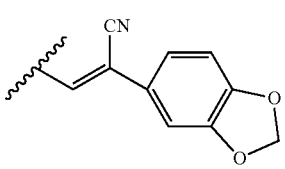 [SMILES: */C=C(\C#N)c1ccc2c(c1)OCO2] | H | (449) |
| 50 | B6e | 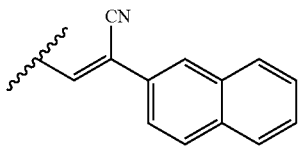 [SMILES: */C=C(\C#N)c1ccc2ccccc2c1] | H | (487) |
| 51 | B6e | 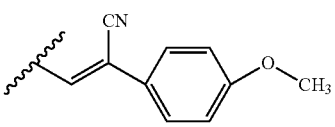 [SMILES: */C=C(\C#N)c1ccc(OC)cc1] | H | (493) |
| 52 | B6e | 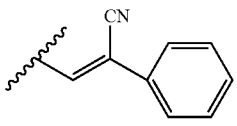 [SMILES: */C=C(\C#N)c1ccccc1] | H | (473) |
| 53 | B6e | 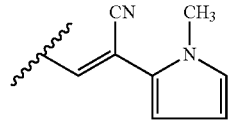 [SMILES: */C=C(\C#N)c1cccn1C] | H | (443) |
| 54 | B6e | 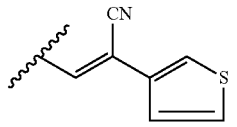 [SMILES: */C=C(\C#N)c1ccsc1] | H | (446) |
| 55 | B6e | | H | (449) |

TABLE 3-continued

[Structure: R4 and R3 on dimethylbenzene ring, NH-pyrimidine-NH-phenyl-CN core]

| Comp No. | Ex. No. | R³ | R⁴ | Physical data m.p. ° C./ (MH+)* |
|---|---|---|---|---|
| 56 | B6e | -CH=C(CN)-C₆H₄-Br (para) | H | (521) |
| 57 | B6e | -CH=C(CN)-C₆H₄-CH₃ (meta) | H | (457) |
| 6 | B4b | —CH₂—N(CH₃)—CH₂—CH₂—N(CH₃)₂ | H | (430) |
| 58 | B4b | -CH₂-N(CH₂Ph)-CH₂-CH₂-N(CH₃)₂ | H | (506) |
| 59 | B4b | -CH₂-(4-methylpiperazin-1-yl) | H | (428) |
| 60 | B4b | -CH₂-[4-(4-acetylphenyl)piperazin-1-yl] | H | (532) |
| 61 | B4b | -CH₂-(4-benzylpiperazin-1-yl) | H | (504) |
| 62 | B4b | -CH₂-(4-benzylpiperidin-1-yl) | H | (503) |
| 63 | B4b | -CH₂-(5-phenylimidazol-1-yl) | H | (472) |
| 64 | B4b | -CH₂-[4-(pyridin-2-yl)piperazin-1-yl] | H | (491) |
| 65 | B4b | —CH₂—N(CH₃)—CH₂—CH₂—CH₂—CH₃ | H | (415) |

TABLE 3-continued
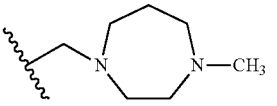
| Comp No. | Ex. No. | R³ | R⁴ | Physical data m.p. ° C./ (MH+)* |
|---|---|---|---|---|
| 66 | B4b | 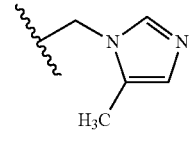 | H | (442) |
| 67 | B4b | 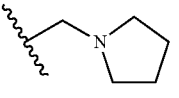 [SMILES: *CN1CCCC1] | H | (410) |
| 68 | B4b | —CH₂—N(CH₃)—CH₂—CH₂—CH₃ | H | (401) |
| 69 | B4b | 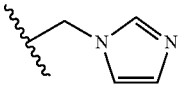 | H | (399) |
| 70 | B4b | 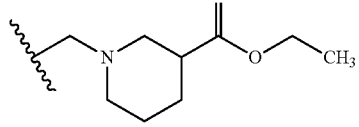 | H | (396) |
| 71 | B4b | —CH₂—N(CH₂—O—CH₂—O—CH₃)₂ | H | (461) |
| 72 | B4b | 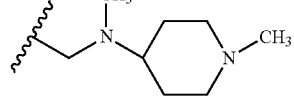 | H | (485) |
| 73 | B4b | 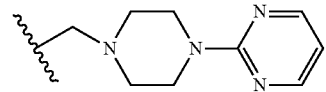 [SMILES: *CN1CCN(c2ncccn2)CC1] | H | (456) |
| 74 | B4b | 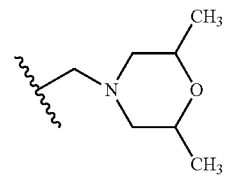 [SMILES: *CN1CC(C)OC(C)C1] | H | (492) |
| 75 | B4b | —CH₂—N(CH₃)—CH₂—CH₂—CN | H | (412) |
| 76 | B4b | 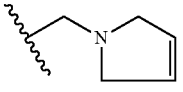 [SMILES: *CN1CC=CC1] | H | (443) |
| 77 | B4b | 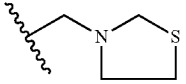 | H | (397) |
| 78 | B4b | | H | (417) |

TABLE 3-continued
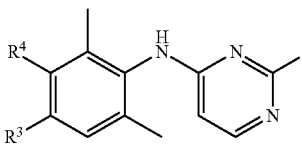
| Comp No. | Ex. No. | R³ | R⁴ | Physical data m.p. ° C./ (MH+)* |
|---|---|---|---|---|
| 79 | B4b | 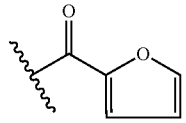 [SMILES: *C(=O)c1ccco1] | H | (464) |
| 80 | B4b | —CH₂—NH—CH₂—CH₂—N(CH₂—CH₃)₂ | H | mp, 105 |
| 81 | B1 | 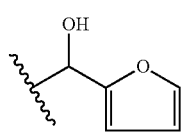 | H | mp. 240 |
| 82 | B10 | 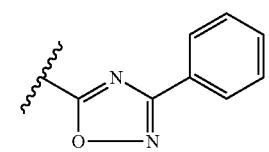 [SMILES: *c1nc(-c2ccccc2)no1] | H | mp. 170 |
| 24 | B13 | —CH₂—CH₂—CN | H | mp. 208 |
| 83 | B8 | 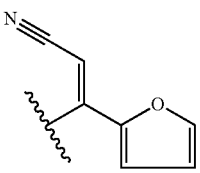 [SMILES: */C(=C\C#N)c1ccco1] | H | mp . >250° C. |
| 14 | B6d | 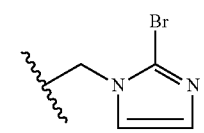 | H | mp. 158 |
| 84 | B6c | —C(CH₃)=CH—CN | H | mp. 224° C. (E) |
| 18 | B9 | —CH(OH)—CH₂—CN | H | mp. 252° C. |
| 85 | B4b | 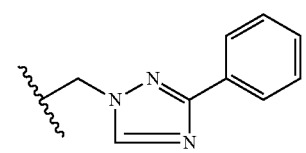 [SMILES: *Cn1cnc(-c2ccccc2)n1] | H | (474) |
| 86 | B4b | 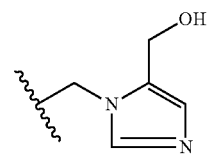 [SMILES: *Cn1cncc1CO] | H | (473) |
| 87 | B4b |  | H | (426) |

TABLE 3-continued
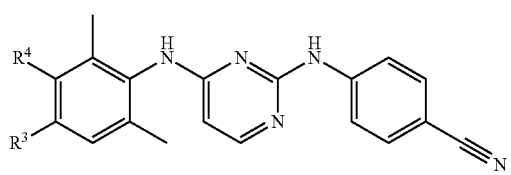
| Comp No. | Ex. No. | R³ | R⁴ | Physical data m.p. ° C./ (MH+)* |
|---|---|---|---|---|
| 88 | B4b | (2-ethyl-imidazol-1-yl-methyl) | H | (424) |
| 89 | B4b | (4,5-dicyano-imidazol-1-yl-methyl) | H | (446) |
| 90 | B4b | (1,2,3-triazol-1-yl-methyl) | H | (397) |
| 91 | B4b | (2-isopropyl-imidazol-1-yl-methyl) | H | (438) |
| 92 | B4b | (2-propyl-imidazol-1-yl-methyl) | H | (438) |
| 93 | B4b | (2-methyl-imidazol-1-yl-methyl) | H | (410) |
| 94 | B4b | (3-methyl-pyrazol-1-yl-methyl) | H | (410) |
| 95 | B4b | (4,5-dichloro-2-methyl-imidazol-1-yl-methyl) | H | (478) |

TABLE 3-continued

| Comp No. | Ex. No. | R³ | R⁴ | Physical data m.p. ° C./ (MH+)* |
|---|---|---|---|---|
| 96 | B4b | [2-(pyridin-4-yl)-1H-imidazol-1-yl]methyl | H | (473) |
| 103 | B6b | —CH═C(CH₃)—CN | H | mp. 201° C. (E) |
| 11 | B6b | —CH═C(CH₃)—CN | H | mp. 246° C. (Z) |
| 10 | B6a | —CH═CH—CN | H | mp. 258° C. (Z) |
| 4 | B3 | —CH₂—CN | H | |
| 17 | B8 | 3-[(dimethylamino)methyl]-1,2,4-oxadiazol-5-yl | H | mp. 110° C. |
| 97 | B8 | 3-ethyl-1,2,4-oxadiazol-5-yl | H | mp. 240° C. |
| 16 | B7 | 2-mercapto-1,3,4-oxadiazol-5-yl | H | mp. >250° C. |
| 7 | B4c | —CH₂—O—CH₂—CH₂—CN | H | mp >260 |
| 5 | B4a | 4-thiomorpholinyl | —NO₂ | mp. 268 |
| 98 | B4a | 4-morpholinyl | —NO₂ | mp. 210 |
| 22 | B4a | 1-piperidinyl | —NO₂ | mp. 252 |
| 23 | B12 | 1-piperidinyl | —NH₂ | mp. 262 |
| 12 | B6c | H | —C(CH₃)═CH—CN | (E) (381) |
| 13 | B6c | H | —C(CH₃)═CH—CN | (Z) (381) |
| 127 | B1 | —N(CH₃)₂ | H | mp. 228° C. |
| 123 | B15a | —C(═O)—CH₂—CN | H | mp. 150° C. |
| 116 | B9C | =N—NH—C(O)-(pyridin-4-yl) | H | (463) |
| 128 | B9C | =N—NH—C(O)-(3-fluorophenyl) | H | (480) |
| 129 | B9C | =N—NH—C(O)-(furan-2-yl) | H | (452) |

TABLE 3-continued

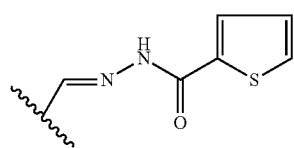 [SMILES: */C=N/NC(=O)c1cccs1]

| Comp No. | Ex. No. | R³ | R⁴ | Physical data m.p. ° C./ (MH+)* |
|---|---|---|---|---|
| 130 | B9C | —CH=N—NH—C(=O)—CH₃ | H | (400) |
| 131 | B9C | —CH=N—NH—C(=O)—CH₂—CN | H | (425) |
| 132 | B9C | 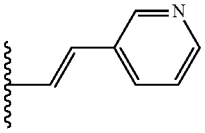 [SMILES: */C=C/c1cccnc1] | H | (468) |
| 115 | B9Bd | —C(=O)—NH—CH₃ | H | (373) |
| 134 | B9Bd | —C(=O)—N(CH₃)₂ | H | (387) |
| 135 | B9Bd | —C(=O)—N(CH₃)—CH₂—CH₃ | H | (401) |
| 136 | B9Bd | —C(=O)—N(CH₂—CH₃)₂ | H | (415) |
| 137 | B9Bd | —C(=O)—NH—CH₂—CH₃ | H | (387) |
| 138 | B9Bd | —C(=O)—NH—CH₂—CN | H | (398) |
| 139 | B9Bd | —C(=O)—N(CH₃)—CH₂—CN | H | (412) |
| 140 | B9Bd | —C(=O)—NH—CH₂—C≡CH | H | (397) |
| 141 | B9Bd | —C(=O)—NH—CH₂—CH=CH₂ | H | (399) |
| 142 | B9Bd | —C(=O)—NH—CH(CH₃)₂ | H | (401) |
| 143 | B1 | —N[CH₂—CH(CH₃)₂]₂ | H | mp. 238° C. |
| 144 | B13 | —CH₂—CH(CN)₂ | H | mp. 160° C. |
| 106 | B6f | —CH=C(CN)—C(=O)—C(CH₃)₃ | H | (E), mp. 193° C. |
| 145 | B9F | 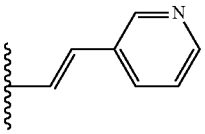 [SMILES: */C=C/c1cccnc1] | H | (E), mp. 229° C. |
| 146 | B9F | 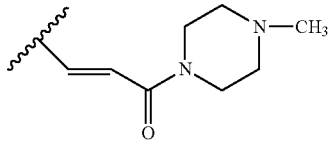 [SMILES: */C=C/C(=O)N1CCN(C)CC1] | H | (Z), mp. 258° C. |
| 147 | B9Ea | —CH=C(CN)—CH₂—CN | H | (Z/E = 88/12) (406) |
| 148 | B6c | —C(CH₂—CH₃)=CH—CN | H | (E), mp. 173° C. |
| 149 | B6c | —C(CH(CH₃)₂)=CH—CN | H | (E), mp. 132° C. |
| 150 | B6c | —C(CH(CH₃)₂)=CH—CN | H | (Z), mp. 1332° C. |
| 151 | B6b | —CH=C(CH₃)—CN | H | (Z), mp. 246° C. |
| 152 | B6b | —CH=C(CH₃)—CN | H | (E), mp. 201° C. |
| 153 | B13 | —CH₂—CH(CH₃)—CN | H | mp. 187° C. |
| 124 | B15b | —C(Cl)=CH—CN | H | |
| 154 | B9Ba | —CH=CH—C(=O)—N(CH₃)—CH₂—CN | H | (E) |
| 112 | B9Ba | —CH=CH—C(=O)—N(CH₃)₂ | H | (E), mp. >264° C. |
| 155 | B9Bc | 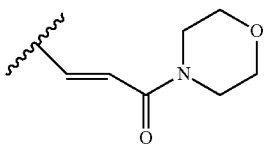 [SMILES: */C=C/C(=O)N1CCOCC1] | H | (E), mp. 156° C. |
| 156 | B9Bc | 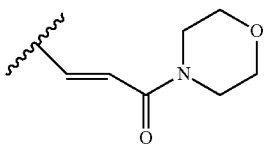 [SMILES: */C=C/C(=O)N1CCOCC1] | H | (E), mp. 168° C. |

TABLE 3-continued

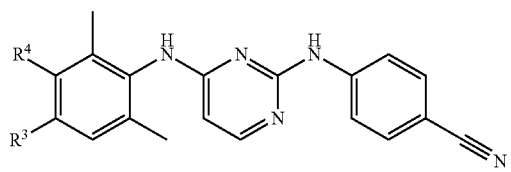

| Comp No. | Ex. No. | R³ | R⁴ | Physical data m.p. ° C./ (MH+)* |
|---|---|---|---|---|
| 157 | B9Bc | (piperidine amide alkene) | H | (E), mp. > 265° C. |
| 158 | B9Bc | —CH=CH—C(=O)—N(CH₃)—CH₂—CH₃ | H | (E), mp. >260° C. |
| 114 | B9Bc | —CH=CH—C(=O)—N(CH₃)—(CH₂)₂—CN | H | (E), mp. 168° C. |
| 159 | B9Bc | —CH=CH—C(=O)—N(CH₂—CH₃)₂ | H | (E), Mp. 249° C. |
| 160 | B6b | —C(CH3)=C(CH3)—CN | H | (E) |
| 107 | B9Aa | —CH=CH—Cl | H | (Z), mp. 250° C. |
| 161 | B9Aa | —CH=CH—Br | H | (Z), mp. 248° C. |
| 111 | B9Ad | —CH=C(Br)₂ | H | mp. 223° C. |
| 122 | B9F | (2-pyridyl vinyl) | H | (E), mp. 120° C. |
| 162 | B9F | (4-pyridyl vinyl) | H | (E), mp. >260° C. |
| 163 | B9F | (4-pyridyl vinyl) | H | mp. 128° C. |
| 164 | B9FF | (2-furyl vinyl) | H | mp. 104° C. |
| 125 | B16a | (furan oxime) | H |  |
| 104 | B2c | (furan aldehyde) | H |  |
| 165 | B9F | (2-thienyl vinyl) | H | mp. 112° C. |

TABLE 3-continued

| Comp No. | Ex. No. | R³ | R⁴ | Physical data m.p. ° C./ (MH+)* |
|---|---|---|---|---|
| 166 | B9F | (2-(1-methylpyrrolyl)vinyl group) | H | mp. 194° C. |
| 167 | B9F | (4-cyanophenyl-vinyl group) | H | mp. 191° C. |
| 126 | B16b | (5-cyano-2-furanyl group) | H | mp. >260° C. |
| 168 | B4c | —CH₂—O—CH₂—CH₃ | H | mp. 201° C. |
| 117 | B9Da | H | —N(CH₃)2 | mp. 132° C. |
| 120 | B9Eb | —CH=C(CN)₂ | H | |
| 253 | B17a/b | —CH=CH—C(=O)NH₂ | H | (E) |
| 254 | B17b | —CH=CH—C(=O)NH₂ | H | (E) HCl |

*(MH⁺) defines the mass of the protonated compound; it was determined with a MicroMass spectrometer equipped with an electrospray probe with a quadripolar analyser.

TABLE 4

| Comp No. | Ex. No. | R³ | R¹ | Physical data mp. ° C./(MH+)* |
|---|---|---|---|---|
| 25 | B6c | —CH=CH—CN | H | mp. 256° C. |
| 99 | B3 | —CH₂—CN | H | mp. 184° C. |
| 100 | B4b | —CH₂—N(CH₂—CH₃)₂ | H | mp. 172 ° C. |
| 102 | B13 | —CH₂—CH₂—CN | H | mp. 224° C. |
| 101 | B4b | —CH₂—N(CH₃)—CH₂—CH₂—CN | H | mp. 196° C. |
| 26 | B14 | —CH=CH—CN | CH₃ | mp. 195° C. |
| 169 | B9Bd | —C(=O)—N(CH₂—CH₃)₂ | H | mp. 172° C. |
| 170 | B4b | —CH₂—N(CH₃)—CH₂—CN | H | |
| 171 | B4b | (pyrrolylmethyl group) | H | (398) |
| 172 | B2a | (thienyl group) | H | mp. 158° C. |
| 173 | B4b | —CH₂—N(CH₃)—CH₂—CH₂—N(CH₃)₂ | H | mp. 196° C. |
| 174 | B4b | —CH₂—N(CH₃)—CH=N—CN | H | mp. 254° C. |
| 175 | B14 | 2-furanyl | CH₃ | mp. 178° C. |

TABLE 4-continued

| Comp No. | Ex. No. | R³ | R¹ | Physical data mp. °C./(MH+)* |
|---|---|---|---|---|
| 118 | B9Db | N-pyrrolyl | H | 164° C. |
| 176 | B14 | N-pyrrolyl | CH₃ | mp. 188° C. |
| 177 | B9Aa | —CH=CH—Br | H | (Z), mp. 169° C. |
| 110 | B9Ac | —CH=C(F)—CN | H | (E) mp. 254° C. |
| 178 | B6b | —CH=C(CH₃)—CN | H | (Z) |
| 179 | B6b | —CH=C(CH₃)—CN | H | (E) |
| 180 | B9Bb | —CH=CH—C(=O)—N(CH₃)—CH₂—C₆H₅ | H | (E) |
| 181 | B9Bc | —CH=CH—C(=O)—NH-cyclopropyl | H | (E)(426) |
| 182 | B9Bc | —CH=CH—C(=O)—NH—CH₂—CH₂—N(CH₃)₂ | H | (E)(427) |
| 183 | B9Bc | —CH=CH—C(=O)—NH—CH₂—CH₂—CH₂—O—CH₃ | H | (E)(458) |
| 184 | B9Bc | —CH=CH—C(=O)—NH—CH₂—CH(CH₃)₂ | H | (E)(442) |
| 185 | B9Bc | —CH=CH—C(=O)—NH—CH₂—CH₂—CN | H | (E) 439) |
| 186 | B9Bc | —CH=CH—C(=O)—NH-cyclohexyl | H | (E)(468) |
| 187 | B9Bc | —CH=CH—C(=O)—NH—CH₂—CH₂—CH₂—N(CH₃)₂ | H | (E)(471) |
| 188 | B9Bc | —CH=CH—C(=O)—NH—(CH₂)₃—O—CH₂—CH₃ | H | (E)(472) |
| 189 | B9Bc | —CH=CH—C(=O)—NH—CH₂—CH₃ | H | (E)(414) |
| 190 | B9Bc | —CH=CH—C(=O)—NH—CH₂—CH₂—O—CH₃ | H | (E)(444) |
| 191 | B9Bc | —CH=CH—C(=O)—NH—CH(CH₃)₂ | H | (E)(428) |
| 192 | B4b | —CH=CH—CH₂—N(CH₂CH₃)—CH₂-(4-pyridyl) | H | (E)(491) |
| 193 | B4b | —CH=CH—CH₂-thiazolidinyl | H | (E)(444) |
| 194 | B4b | —CH=CH—CH₂—N(CH₃)—CH₂—CH₂—CN | H | (E)(439) |
| 195 |  | —CH=CH—CH₂-(4-carbamoylpiperidin-1-yl) | H | (E)(483) |
| 196 | B4b | —CH=CH—CH₂—N(CH₂—CH₂—O—CH₃)₂ | H | (E)(488) |

TABLE 4-continued

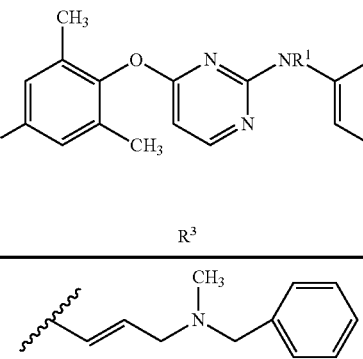

| Comp No. | Ex. No. | R³ | R¹ | Physical data mp. ° C./(MH+)* |
|---|---|---|---|---|
| 197 | B4b | 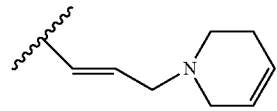 [SMILES: */C=C/CN1CC=CCC1] | H | (E)(476) |
| 198 | B4b | —CH=CH—CH₂—N(CH₃)—CH₂—CH₂—CH₃ | H | (E)(428) |
| 199 | B4b | —CH=CH—CH₂—N(CH₃)—CH₂—CH₂—N(CH₂—CH₃)₂ | H | (E)(485) |
| 200 | B4b | —CH=CH—CH₂—N(CH₂—CH₃)—CH₃ | H | (E)(414) |
| 201 | B4b | —CH=CH—CH₂—N(CH₂—CH₂—CH₃)₂ | H | (E)(456) |
| 202 | B4b | —CH=CH—CH₂—N(CH₃)—CH₂—CH₂—CH₂—CH₃ | H | (E)(442) |
| 203 | B4b | 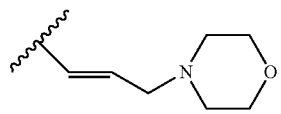 | H | (E)(438) |
| 204 | B4b | 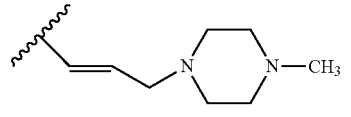 | H | (E)(442) |
| 205 | B4b | 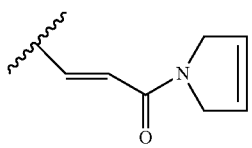 [SMILES: */C=C/C(=O)N1CC=CC1] | H | (E)(455) |
| 206 | B4b | —CH=CH—CH₂—N(benzyl)-CH₂—CH₂—N(CH₃)₂ | H | (E)(533) |
| 207 | B4b | —CH=CH—CH—N(CH₃)₂ | H | (E)(457) |
| 208 | B4b | —CH=CH—CH₂—N(isopropyl)₂ | H | (E)(456) |
| 121 | B9Bb | —CH=CH—C(=O)—NH₂ | H | (E) |
| 209 | B9Bb | 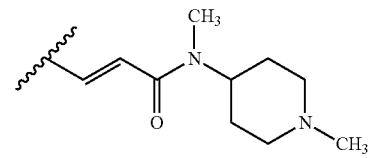 [SMILES: */C=C/C(=O)N(C)C1CCN(C)CC1] | H | (E), mp. 116° C. |
| 210 | B9Bb | 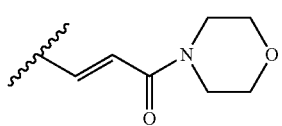 [SMILES: */C=C/C(=O)N1CCOCC1] | H | (E), mp. 254° C. |
| 211 | B9Bb | —CH=CH—C(=O)—N(CH₃)—CH₂—CH₂—OH | H | (E), mp. 222° C. |
| 212 | B9Ba | —CH=CH—C(=O)—N(CH₃)—CH₂—CN | H | (E), mp. 198° C. |
| 213 | B6c | —C(CH₃)=CH—CN | H | (E) |
| 214 | B9Bc | —CH=CH—C(=O)—N(CH₃)—CH₂—CH₂—CN | H | (E), mp. 204° C. |
| 215 | B9Bc | —CH=CH—C(=O)—N(CH₃)—CH₂—CH₃ | H | (E), mp. 211° C. |
| 216 | B9Bc |  | H | (E), mp. 246° C. |
| 217 | B9Bc | —CH=CH—C(=O)—N(CH₂—CH₃)₂ | H | (E), mp. 226° C. |

TABLE 4-continued

[Structure: 2,6-dimethylphenyl (with R³ at para position) ether linked to pyrimidine, which is linked via NR¹ to 4-cyanophenyl]

| Comp No. | Ex. No. | R³ | R¹ | Physical data mp. °C./(MH+)* |
|---|---|---|---|---|
| 218 | B9Bc | –CH=CH–C(=O)–(piperidin-1-yl) | H | (E), mp. 196° C. |
| 219 | B9Ba | —CH=CH—C(=O)—N(CH₃)₂ | H | (E), mp. 225° C. |
| 220 | B9E | —CH=C(CN)—CH₂—CN | H | (Z), mp. 195° C. |
| 109 | B9Ab | —CH=CH—Cl | H | (E), mp. 200° C. |
| 108 | B9Ab | —CH=CH—Cl | H | (Z), mp. 165° C. |
| 221 | B9Ba | —CH=CH—C(=O)—NH—CH₃ | H | (E), mp. 260° C. |
| 222 | B9Bb | —CH=CH—C(=O)—N(CH₂—CH₂—O—CH₃)₂ | H | (E), mp. 158° C. |
| 223 | B9Bb | –CH=CH–C(=O)–(thiomorpholin-4-yl) | H | (E), mp. 208° C. |
| 224 | B9Bb | –CH=CH–C(=O)–N(CH₃)–CH₂–CH₂–phenyl | H | (E), mp. 208° C. |
| 113 | B9Bb | —CH=CH—C(=O)—N(CH₃)—CH₂—CH₂—CH₂—CH₃ | H | (E), mp. 212° C. |
| 225 | B4b | —CH₂—N(CH₂—CH₂—CN)₂ | H | mp. 154° C. |
| 226 | B2a | 2-furanyl | H | mp. 162° C. |

*(MH⁺) defines the mass of the protonated compound; it was determined with a MicroMass spectrometer equipped with an electrospray probe with a quadripolar analyser.

TABLE 5

[Structure: phenyl substituted with R⁴ᵃ, R³, R⁴ᵇ linked via X¹ to pyrimidine, linked via NH to 4-cyanophenyl]

| Comp No. | Ex. No. | R³ | R⁴ᵃ | R⁴ᵇ | X¹ | Physical data mp. °C. |
|---|---|---|---|---|---|---|
| 227 | B13 | —CH₂—CH₂—CN | CH₃ | H | —NH | mp. 186° C. |
| 228 | B4b | —CH₂—N(CH₃)—CH₂—CN | CH₃ | H | —NH | mp. 138° C. |
| 229 | B6b | —CH=C(CH₃)—CN | CH₃ | H | —NH | mp. 190° C. |
| 230 | B6c | —CH=CH—CN | CH₃ | H | —O— | (E), mp. 254° C. |
| 231 | B6b | —CH=C(CH₃)—CN | CH₃ | H | —O— | mp. 150° C. |
| 232 | B6c | —C(CH₃)=CH—CN | CH₃ | H | —O— | (E), mp. 234° C. |
| 105 | B4d | —CH₂—O—CH₂—CH₃ | CH₃ | H | —O— | mp. 140° C. |
| 233 | B6b | —CH=C(CH₃)—CN | CH₃ | Cl | —NH | mp. 214° C. |
| 234 | B13 | —CH₂—CH₂—CN | CH₃ | H | —O— | mp. 199° C. |
| 235 | B13 | —CH(CH₃)—CH₂—CN | CH₃ | H | —O— | mp. 195° C. |
| 236 | B13 | —CH₂—CH(CH₃)-CN | CH₃ | H | —O— | mp. 161° C. |
| 237 | B6c | —CH=CH—CN | CH₃ | H | —NH | (E), mp. >264° C. |
| 238 | B3 | —CH₂—CN | CH₃ | Cl | —NH | mp. 184° C. |
| 239 | B6c | —CH=CH—CN | CH₃ | 2-furanyl | —NH | (E) mp. 175° C. |
| 119 | B9E | —CH=C(CN)—CH₂—CN | CH₃ | 2-furanyl | —NH | |

TABLE 5-continued

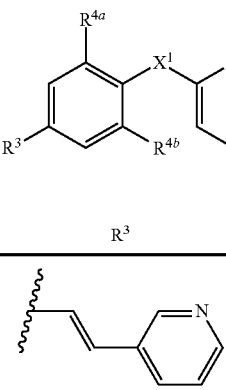

| Comp No. | Ex. No. | R³ | R⁴ᵃ | R⁴ᵇ | X¹ | Physical data mp. ° C. |
|---|---|---|---|---|---|---|
| 240 | B9F | (3-pyridyl-CH=CH-) | CH₃ | Cl | —NH | mp. 248° C. Z/E = 50/50 |
| 241 | B4b | —CH₂—N(CH₃)—CH₂—CH₂—CN | CH₃ | Br | —NH | mp. 148° C. |
| 242 | B1 | —CH=CH—CN | H | isopropyl | —NH | (E) 30%-(Z) 70% |
| 243 | B4b | —CH₂—N(CH₃)—CH₂—CH₂—CN | CH₃ | Cl | —NH | mp. 85° C. |
| 244 | B6c | —CH=CH—CN | H | Br | —NH | (E), mp. 270° C. |
| 245 | B6c | —CH=CH—CN | H | —OCH₃ | —NH | (E), mp. 258° C. |
| 246 | B6b | —C(CH₃)=C(CH₃)—CN | CH₃ | H | —O— | (E), mp. 214° C. |
| 247 | B6b | —CH=C(CH₃)—CN | CH₃ | Br | —NH | mp. 212° C. |
| 248 | B6c | —CH=CH—CN | CH₃ | Br | —NH | mp. 250° C. |
| 249 | B6b | —CH=C(CH₃)—CN | H | —OCH₃ | —NH | mp. 166° C. |
| 250 | B6b | —CH=C(CH₃)—CN | H | Br | —NH | mp. 186° C. |
| 251 | B13 | —CH₂—CH₂—CN | H | —OCH₃ | —NH | mp. 228° C. |
| 252 | B4c | —CH₂—O—CH₂—CH₂—CN | H | Cl | —NH | mp. 168° C. |
| 133 | B6c | —CH=CH—CN | CH₃ | Cl | —NH | (E), mp, 258° C. |

C. Pharmacological Example

The pharmacological activity of the present compounds was examined using the following test.

A rapid, sensitive and automated assay procedure was used for the in vitro evaluation of anti-HIV agents. An HIV-1 transformed T4-cell line, MT-4, which was previously shown (Koyanagi et al., *Int. J. Cancer*, 36, 445-451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in M) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(ODT)_{HIV}$ is the optical density measured with a given concentration of the test compound in HIV-infected cells; $(ODC)_{HIV}$ is the optical density measured for the control untreated HIV-infected cells; $(ODC)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in M). The ratio of $CC_{50}$ to $IC_{50}$ was defined as the selectivity index (SI).

Table 6 lists the $pIC_{50}$ ($-\log IC_{50}$), $pCC_{50}$ ($-\log CC_{50}$) and pSI ($pCC_{50}$-$pIC_{50}$) values for the compounds of formula (I).

For example, a compound with a $IC_{50}$ value of $10^{-9}$M, i.e. $pIC_{50}$=9, and a $CC_{50}$ value of $10^{-5}$ M, i.e. $pCC_{50}$=5, has a SI of $10^{-5}$ M/$10^{-9}$M=10.000, i.e. a pSI of 5-9=−4.

TABLE 6

| Co. No. | $pIC_{50}$ (M) | $pCC_{50}$ (M) | pSI |
|---|---|---|---|
| 21 | 8.4 | 4.9 | −3.5 |
| 3 | 8.4 | 5.5 | −2.9 |
| 1 | 9.4 | 5.0 | −4.4 |
| 34 | 8.0 | 4.8 | −3.2 |
| 19 | 8.4 | 4.8 | −3.6 |
| 45 | 8.7 | 5.0 | −3.8 |
| 49 | 8.0 | 4.8 | −3.2 |
| 70 | 8.1 | 4.8 | −3.3 |
| 75 | 9.0 | 5.0 | −4.0 |
| 78 | 8.4 | 4.9 | −3.5 |
| 79 | 8.0 | 5.3 | −2.7 |
| 84 | 9.0 | 4.5 | −4.5 |
| 18 | 8.8 | 4.9 | −4.0 |
| 25 | 9 | 4 | −5 |
| 24 | 9.1 | 5.7 | −3.4 |
| 81 | 9.1 | 5.6 | −3.5 |
| 11 | 9.2 | 5.7 | −3.5 |
| 10 | 9.2 | 6.3 | −2.9 |
| 174 | 8.8 | 5.3 | −3.5 |
| 227 | 9.5 | <4.0 | <−5.5 |
| 144 | 8.6 | 6.4 | −2.2 |
| 229 | 8.8 | <4.0 | <−4.8 |
| 118 | 8.4 | 4.1 | <−4.1 |
| 177 | 8.3 | <4.0 | <−4.3 |
| 106 | 7.7 | 5.2 | −2.5 |
| 145 | 8.7 | 5.3 | −3.4 |
| 147 | 9.4 | 5.7 | −3.7 |
| 148 | 8.8 | 4.9 | −3.9 |
| 230 | 9.2 | <4.0 | <−5.2 |
| 231 | 9.2 | <4.0 | <−5.2 |
| 232 | 8.4 | <4.0 | <−4.4 |
| 105 | 7.2 | <4.0 | <−3.2 |
| 110 | 8.6 | 4.3 | −4.3 |
| 233 | 9.3 | 5.7 | −3.6 |
| 234 | 8.7 | <4.0 | <−4.7 |

TABLE 6-continued

| Co. No. | pIC$_{50}$ (M) | pCC$_{50}$ (M) | pSI |
|---|---|---|---|
| 235 | 9.3 | <4.0 | <−5.3 |
| 236 | 8.8 | <4.0 | <−4.8 |
| 149 | 9.1 | 5.3 | −3.8 |
| 150 | 8.8 | 4.8 | −4.0 |
| 237 | 8.9 | <4.0 | <−4.9 |
| 151 | 9.1 | 5.5 | −3.6 |
| 152 | 9.1 | 4.8 | −4.3 |
| 178 | 8.8 | 5.7 | −3.1 |
| 179 | 8.9 | <4.0 | <−4.9 |
| 153 | 9.2 | 6.3 | −2.9 |
| 124 | 8.5 | 4.7 | −3.8 |
| 238 | 9.5 | 5.6 | −3.9 |
| 112 | 9.1 | 4.9 | −4.2 |
| 244 | 9.2 | 4 | −5.2 |
| 209 | 8.6 | 4.9 | −3.7 |
| 210 | 8.3 | 4.8 | −3.5 |
| 155 | 8.8 | 6.3 | −2.5 |
| 156 | 7.7 | 5.1 | −2.6 |
| 158 | 8 | 5.5 | −2.5 |
| 212 | 9.1 | 5 | −4.1 |
| 114 | 8.6 | 5.1 | −3.5 |
| 213 | 9 | 4.8 | −4.2 |
| 214 | 8.6 | 5.1 | −3.5 |
| 215 | 9.1 | 5.5 | −3.6 |
| 216 | 8.2 | 5 | −3.6 |
| 219 | 9.1 | 5 | −4.1 |
| 245 | 8.8 | 4 | −4.8 |
| 146 | 8.4 | 5.4 | −3 |
| 247 | 9.2 | 6.2 | −3 |
| 248 | 9.3 | 5.7 | −3.5 |
| 249 | 8.5 | 4 | −4.5 |
| 42 | 9 | 6.3 | −2.7 |
| 251 | 8.9 | 5 | −3.9 |
| 133 | 9.2 | 4 | −5.2 |
| 9 | 8.8 | 4.8 | −4 |
| 239 | 8.9 | 5 | −3.9 |
| 241 | 9.4 | 5.3 | −4.1 |
| 126 | 8.4 | 4.9 | −3.5 |

The invention claimed is:

1. A combination containing (a) a compound of formula (I)

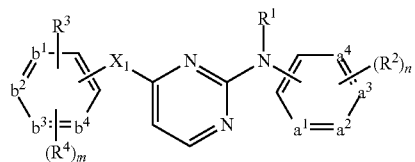

an N-oxide, a pharmaceutically acceptable addition salt, a quaternary amine or a stereochemically isomeric form thereof, wherein -a$^1$=a$^2$-a$^3$=a$^4$- represents a bivalent radical of formula —CH═CH—CH═CH— (a-1);

-b$^1$=b$^2$-b$^3$=b$^4$- represents a bivalent radical of formula

—CH═CH—CH═CH— (b-1);

n is 0, 1, 2, 3, 4 or 5;
m is 1, 2, 3, or 4;
R$^1$ is selected from the group consisting of: hydrogen; aryl; formyl; C1-6alkylcarbonyl; C1-6alkyloxycarbonyl; C1-6alkyl; C1-6alkyl substituted with a member selected from the group consisting of: formyl, C1-6alkylcarbonyl, C1-6alkyloxycarbonyl, and C1-6alkylcarbonyloxy; and C1-6alkyloxyC1-6alkylcarbonyl substituted with C1-6alkyloxycarbonyl;

each R$^2$ is independently selected from: hydroxy; halo; C1-6alkyl optionally substituted with cyano or —C(═O)R$^6$; C$_{3-7}$cycloalkyl; C$_{2-6}$alkenyl optionally substituted with one or more halogen atoms or cyano; C$_{2-6}$alkynyl optionally substituted with one or more halogen atoms or cyano; C1-6alkyloxycarbonyl; carboxyl; cyano; nitro; amino; mono- or di(C$_{1-6}$alkyl)amino; polyhalomethyl; polyhalomethylthio; —S(═O)$_p$R$^6$; —NH—S(═O)$_p$R$^6$; —C(═O)R$^6$; —NHC(═O)H; —C(═O)NHNH$_2$; —NHC(═O)R$^6$; —C(═NH)R$^6$ and a radical of formula

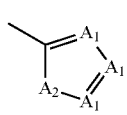

wherein each A$_1$ is independently selected from the group consisting of: N, CH and CR$^6$; and
A$_2$ is selected from the group consisting of: NH, O, S and NR$^6$;
X$_1$ is selected from the group consisting of: —NR$^5$—, —NH—NH—, —N═N—, —O—, —C(═O)—, C$_{1-4}$alkanediyl, —CHOH—, —S—, —S(═O)$_p$—, —X$_2$—C$_{1-4}$alkanediyl- and —C$_{1-4}$alkanediyl-X$_2$—;
X$_2$ is —NR$^5$—, —NH—NH—, —N═N—, —O—, —C(═O)—, —CHOH—, —S—, —S(═O)$_p$—;
R$^3$ is C1-6alkyl substituted with R$^7$;
R$^4$ is selected from the group consisting of: halo, hydroxy, C1-6alkyl, C3-7cycloalkyl, C1-6alkyloxy, cyano, nitro, polyhaloC$_{1-6}$alkyl, polyhaloC$_{1-6}$alkyloxy, aminocarbonyl, C1-6alkyloxycarbonyl, C1-6alkylcarbonyl, formyl, amino, mono- or di(C$_{1-4}$alkyl)amino and R$^7$;
R$^5$ is hydrogen;
R$^6$ is selected from the group consisting of: C$_{1-4}$alkyl; amino; mono- or di(C$_{1-4}$alkyl)amino; and polyhaloC$_{1-4}$alkyl;
R$^7$ is selected from the group consisting of: a monocyclic, bicyclic or tricyclic saturated, partially saturated or aromatic carbocycle; or a monocyclic, bicyclic or tricyclic saturated, partially saturated or aromatic heterocycle; wherein each of said carbocyclic or heterocyclic ring systems may optionally be substituted with one, two, three, four or five substituents each independently selected from the group consisting of: halo, hydroxy, mercapto, C1-6alkyl, hydroxyC1-6alkyl, aminoC1-6alkyl, mono or di(C1-6alkyl)aminoC1-6alkyl, formyl, C1-6alkylcarbonyl, C$_{3-7}$cycloalkyl, C1-6alkyloxy, C1-6alkyloxycarbonyl, C1-6alkylthio, cyano, nitro, polyhaloC$_{1-6}$alkyl, polyhaloC$_{1-6}$alkyloxy, aminocarbonyl, —CH(═N—O—R$^8$), R$^{7a}$, —X$_3$—R$^{7a}$ and R$^{7a}$—C$_{1-4}$alkyl;
R$^{7a}$ is a monocyclic, bicyclic or tricyclic saturated, partially saturated or aromatic carbocycle; or a monocyclic, bicyclic or tricyclic saturated, partially saturated or aromatic heterocycle; wherein each of said carbocyclic or heterocyclic ring systems may optionally be substituted with one, two, three, four or five substituents each independently selected from the group consisting of: halo, hydroxy, mercapto, C1-6alkyl, hydroxyC1-6 alkyl, aminoC1-6alkyl, mono or di(C1-6alkyl) aminoC1-6alkyl, formyl, C1-6alkylcarbonyl, C$_{3-7}$cycloalkyl, C1-6alkyloxy, C1-6alkyloxycarbonyl, C1-6alkylthio, cyano, nitro, polyhaloC$_{1-6}$alkyl, polyhaloC$_{1-6}$alkyloxy, aminocarbonyl, and —CH(=N—O—R$^8$);

R$^8$ is selected from the group consisting of: hydrogen, C$_{1-4}$alkyl, aryl and arylC$_{1-4}$alkyl;

X$_3$ is —NR$^5$—, —NH—NH—, —N=N—, —O—, —C(=O)—, —S—, —S(=O)$_p$—, —X$_2$—C$_{1-4}$alkanediyl-, —C$_{1-4}$alkanediyl-X$_{2a}$—, —C$_{1-4}$alkanediyl-X$_{2b}$—C$_{1-4}$alkanediyl, —C(=N—OR$^8$)—C$_{1-4}$alkanediyl-;

with X$_{2a}$ being —NH—NH—, —N=N—, —O—, —C(=O)—, —S—, —S(=O)$_p$—; and with X$_{2b}$ being —NH—NH—, —N=N—, —C(=O)—, —S—, —S(=O)$_p$—;

p is 1 or 2; and aryl is phenyl; or phenyl substituted with one, two, three, four or five substituents each independently selected from the group consisting of: halo, hydroxy, mercapto, C1-6alkyl, hydroxyC1-6alkyl, aminoC1-6alkyl, mono or di(C1-6alkyl)aminoC1-6alkyl, C1-6alkylcarbonyl, C$_{3-7}$cycloalkyl, C1-6alkyloxy, C1-6alkyloxycarbonyl, C1-6alkylthio, cyano, nitro, polyhaloC$_{1-6}$alkyl, polyhaloC$_{1-6}$alkyloxy, aminocarbonyl, R$^7$ and —X$_3$—R$^7$;

and (b) another antiretroviral compound.

2. A pharmaceutical composition comprising a pharmaceutically acceptable carrier and as active ingredients (a) a compound of formula (I)

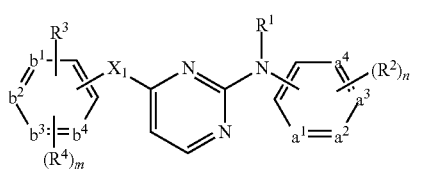

(I)

an N-oxide, a pharmaceutically acceptable addition salt, a quaternary amine or a stereochemically isomeric form thereof, wherein -a$^1$=a$^2$-a$^3$=a$^4$- represents a bivalent radical of formula —CH=CH—CH=CH— (a-1);

-b$^1$=b$^2$-b$^3$=b$^4$- represents a bivalent radical of formula

—CH=CH—CH=CH— (b-1);

n is 0, 1, 2, 3, or 4;

m is 1, 2, 3, or 4;

R$^1$ is selected from the group consisting of: hydrogen; aryl; formyl; C1-6alkylcarbonyl; C1-6alkyloxycarbonyl; C1-6alkyl; C1-6alkyl substituted with a member selected from the group consisting of: formyl, C1-6alkylcarbonyl, C1-6alkyloxycarbonyl, and C1-6alkylcarbonyloxy; and C1-6alkyloxyC1-6alkylcarbonyl substituted with C1-6alkyloxycarbonyl;

each R$^2$ is independently selected from: hydroxy; halo; C1-6alkyl optionally substituted with cyano or —C(=O)R$^6$; C$_{3-7}$cycloalkyl; C$_{2-6}$alkenyl optionally substituted with one or more halogen atoms or cyano; C$_{2-6}$alkynyl optionally substituted with one or more halogen atoms or cyano; C1-6alkyloxycarbonyl; carboxyl; cyano; nitro; amino; mono- or di(C$_{1-6}$alkyl) amino; polyhalomethyl; polyhalomethylthio; —S(=O)$_p$ R$^6$; —NH—S(=O)$_p$R$^6$; —C(=O)R$^6$; —NHC(=O)H; —C(=O)NHNH$_2$; —NHC(=O)R$^6$; —C(=NH)R$^6$ and a radical of formula

(c)

wherein each A$_1$ is independently selected from the group consisting of: N, CH and CR$^6$; and A$_2$ is selected from the group consisting of: NH, O, S and NR$^6$;

X$_1$ is selected from the group consisting of: —NR$^5$—, —NH—NH—, —N=N—, —O—, —C(=O)—, C$_{1-4}$alkanediyl, —CHOH—, —S—, —S(=O)$_p$—, —X$_2$—C$_{1-4}$alkanediyl- and —C$_{1-4}$alkanediyl-X$_2$—;

X$_2$ is —NR$^5$—, —NH—NH—, —N=N—, —O—, —C(=O)—, —CHOH—, —S—, —S(=O)$_p$—;

R$^3$ is C1-6alkyl substituted with R$^7$;

R$^4$ is selected from the group consisting of: halo, hydroxy, C1-6alkyl, C$_{3-7}$cycloalkyl, C1-6alkyloxy, cyano, nitro, polyhaloC$_{1-6}$alkyl, polyhaloC$_{1-6}$alkyloxy, aminocarbonyl, C1-6alkyloxycarbonyl, C1-6alkylcarbonyl, formyl, amino, mono- or di(C$_{1-4}$alkyl)amino and R$^7$;

R$^5$ is hydrogen;

R$^6$ is selected from the group consisting of: C$_{1-4}$alkyl; amino; mono- or di(C$_{1-4}$alkyl)amino; and polyhaloC$_{1-4}$alkyl;

R$^7$ is selected from the group consisting of: a monocyclic, bicyclic or tricyclic saturated, partially saturated or aromatic carbocycle; or a monocyclic, bicyclic or tricyclic saturated, partially saturated or aromatic heterocycle; wherein each of said carbocyclic or heterocyclic ring systems may optionally be substituted with one, two, three, four or five substituents each independently selected from the group consisting of: halo, hydroxy, mercapto, C1-6alkyl, hydroxyC1-6alkyl, aminoC1-6alkyl, mono or di(C1-6alkyl)aminoC1-6alkyl, formyl, C1-6alkylcarbonyl, C$_{3-7}$ cycloalkyl, C1-6alkyloxy, C1-6alkyloxycarbonyl, C1-6alkylthio, cyano, nitro, polyhaloC$_{1-6}$alkyl, polyhaloC$_{1-6}$alkyloxy, aminocarbonyl, —CH(=N—O—R$^8$), R$^{7a}$, —X$_3$—R$^{7a}$ and R$^{7a}$—C$_{1-4}$alkyl;

R$^{7a}$ is a monocyclic, bicyclic or tricyclic saturated, partially saturated or aromatic carbocycle; or a monocyclic, bicyclic or tricyclic saturated, partially saturated or aromatic heterocycle; wherein each of said carbocyclic or heterocyclic ring systems may optionally be substituted with one, two, three, four or five substituents each independently selected from the group consisting of: halo, hydroxy, mercapto, C1-6alkyl, hydroxyC1-6alkyl, aminoC1-6alkyl, mono or di(C1-6alkyl)aminoC1-6alkyl, formyl, C1-6alkylcarbonyl, C$_{3-7}$ cycloalkyl, C1-6alkyloxy, C1-6alkyloxycarbonyl, C1-6alkylthio, cyano, nitro, polyhaloC$_{1-6}$alkyl, polyhaloC$_{1-6}$alkyloxy, aminocarbonyl, and —CH(=N—O—R$^8$);

R$^8$ is selected from the group consisting of: hydrogen, C$_{1-4}$alkyl, aryl and arylC$_{1-4}$alkyl;

X$_3$ is —NR$^5$—, —NH—NH—, —N=N—, —O—, —C(=O)—, —S—, —S(=O)$_p$—, —X$_2$—C$_{1-4}$alkanediyl-, —C$_{1-4}$alkanediyl-X$_{2a}$—, C$_{1-4}$alkanediyl-X$_{2b}$—C$_{1-4}$alkanediyl, —C(=N—OR$^8$)—C$_{1-4}$alkanediyl-;

with X$_{2a}$ being —NH—NH—, —N=N—, —O—, —C(=O)—, —S—, —S(=O)$_p$—; and with X$_{2b}$ being —NH—NH—, —N=N—, —C(=O)—, —S—, —S(=O)$_p$—;

p is 1 or 2; and aryl is phenyl; or phenyl substituted with one, two, three, four or five substituents each independently selected from the group consisting of: halo, hydroxy, mercapto, C1-6alkyl, hydroxyC1-6alkyl, aminoC1-6alkyl, mono or di(C1-6alkyl)aminoC1-6alkyl, C1-6alkylcarbonyl, $C_{3-7}$cycloalkyl, C1-6alkyloxy, C1-6alkyloxycarbonyl, C1-6alkylthio, cyano, nitro, polyhalo$C_{1-6}$alkyl, polyhalo$C_{1-6}$alkyloxy, aminocarbonyl, $R^7$ and —$X_3$—$R^7$;

and (b) another antiretroviral compound.

3. A combination containing (a) a compound of formula (I''')

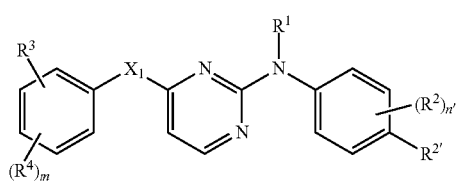

an N-oxide, a pharmaceutically acceptable addition salt, a quaternary amine or a stereochemically isomeric form thereof, wherein $R^1$, $R^2$, $R^3$, $R^4$, m and $X_1$ are as defined in claim 1;

n' is 0, 1, 2, 3 or 4; and $R^{2'}$ is selected from the group consisting of: halo, $C_{1-6}$alkyl, trihalomethyl, cyano, aminocarbonyl, and $C_{1-6}$alkyl substituted with cyano or aminocarbonyl;

and (b) another antiretroviral compound.

4. A combination according to claim 3 wherein $R^{2'}$ is selected from the group consisting of: cyano; aminocarbonyl; and $C_{1-6}$alkyl substituted with cyano or aminocarbonyl.

5. A pharmaceutical composition comprising a pharmaceutically acceptable carrier and as active ingredients (a) a compound of formula (I''')

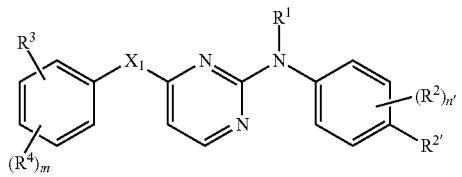

an N-oxide, a pharmaceutically acceptable addition salt, a quaternary amine or a stereochemically isomeric form thereof, wherein $R^1$, $R^2$, $R^3$, $R^4$, m and $X_1$ are as defined in claim 2;

n' is 0, 1, 2, 3 or 4; and $R^{2'}$ is a member selected from the group consisting of: halo, $C_{1-6}$alkyl, trihalomethyl, cyano, aminocarbonyl, and $C_{1-6}$alkyl substituted with cyano or aminocarbonyl;

and (b) another antiretroviral compound.

6. The composition as claimed in claim 5 wherein $R^{2'}$ is cyano, aminocarbonyl or $C_{1-6}$alkyl, wherein said $C_{1-6}$alkyl is substituted with cyano or aminocarbonyl.

7. The combination as claimed in claim 1, wherein the compound is selected from the group consisting of:

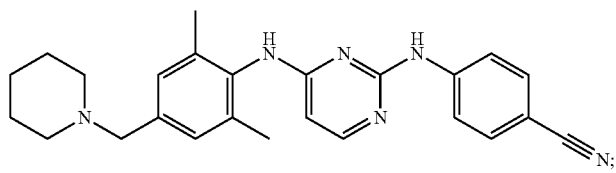

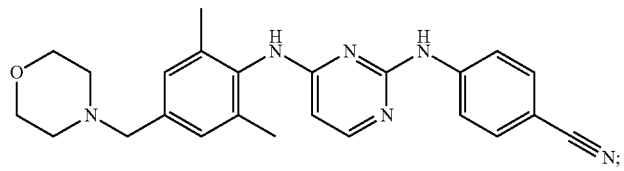

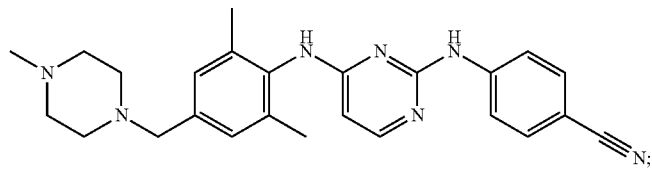

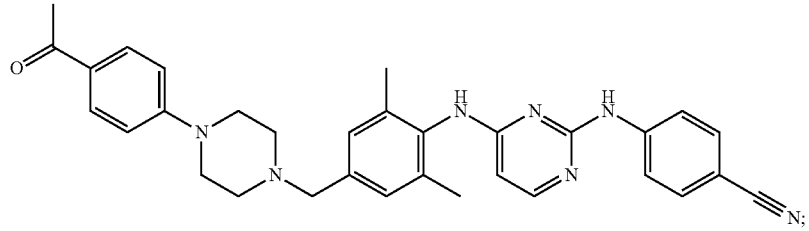

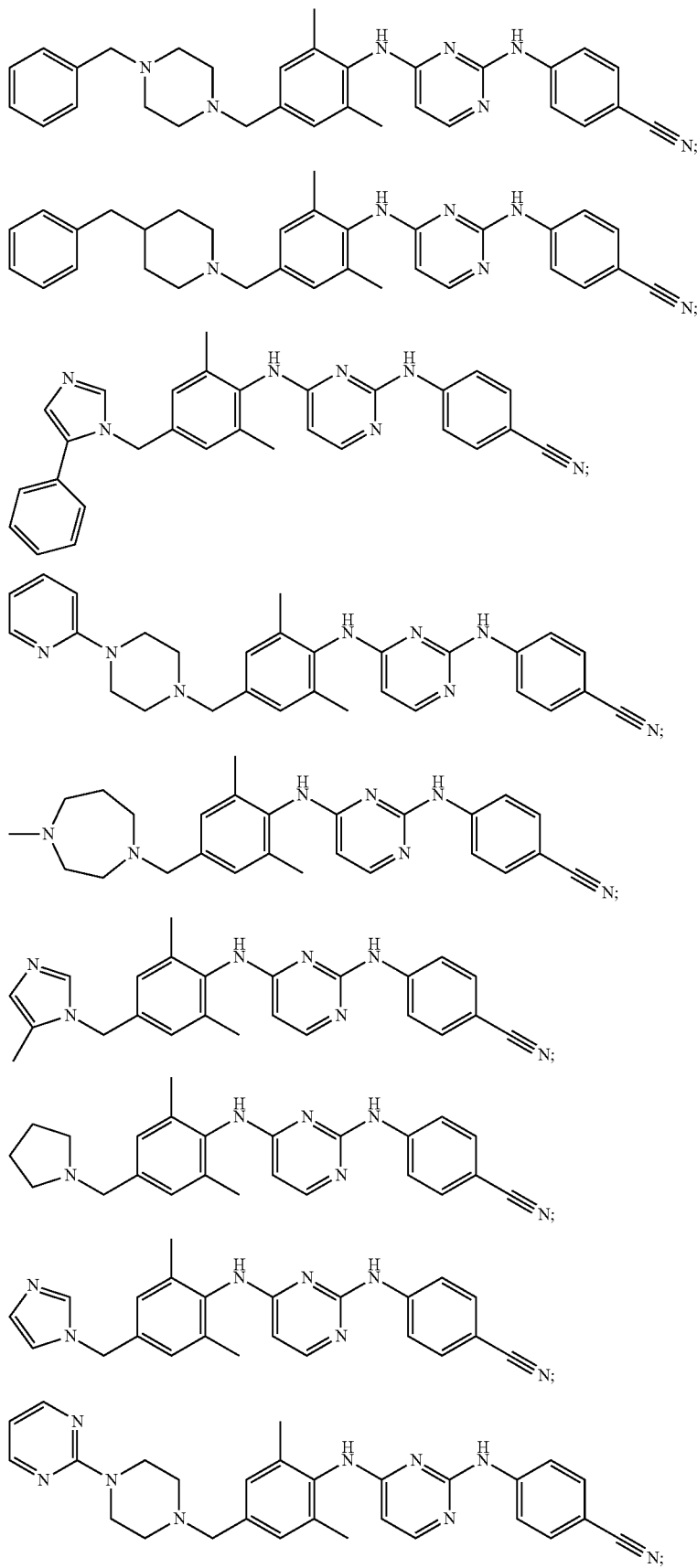

-continued
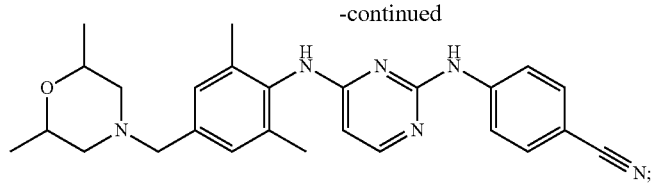
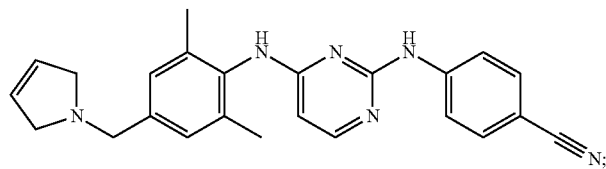
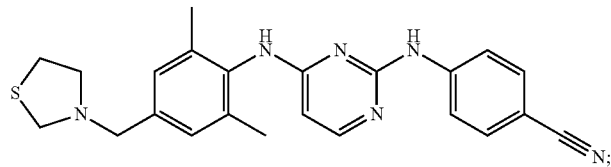
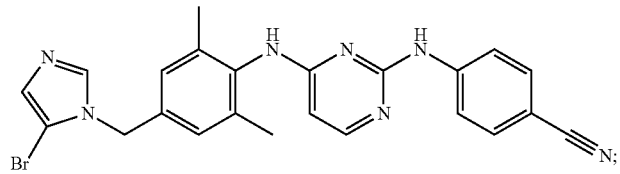
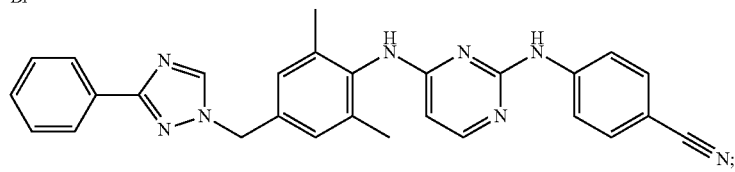
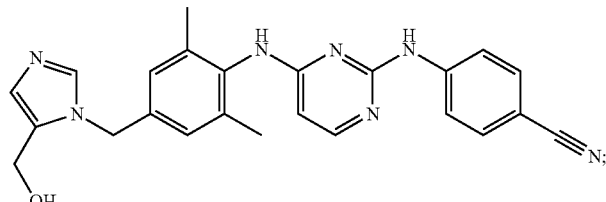
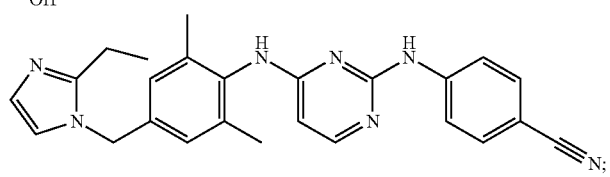
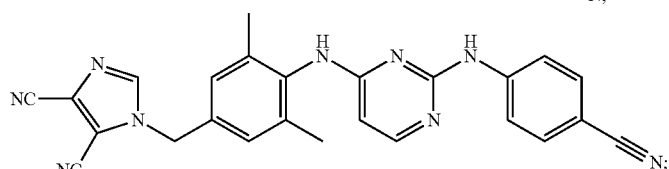
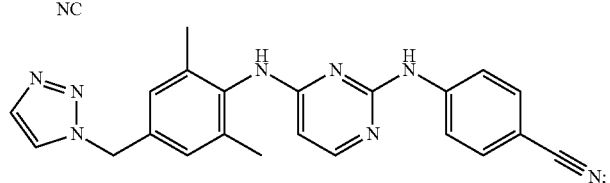
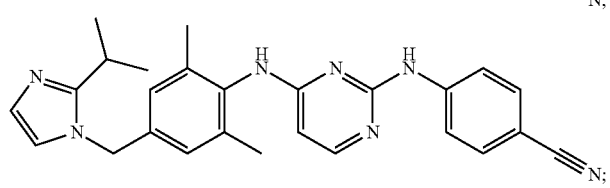

-continued
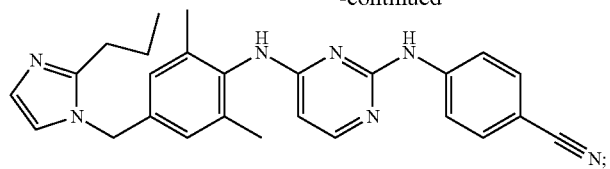
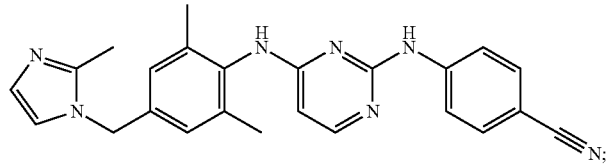
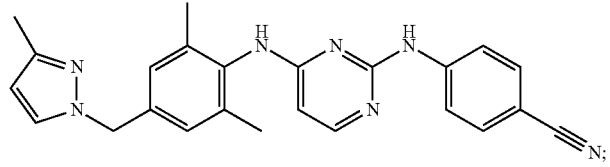
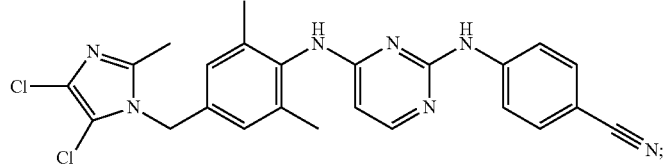
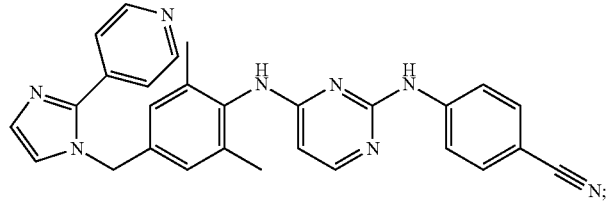
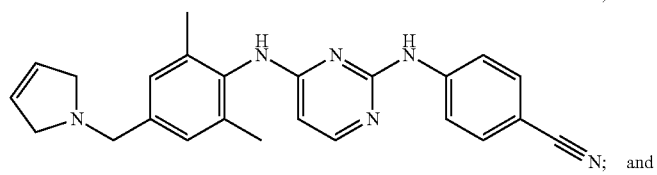; and
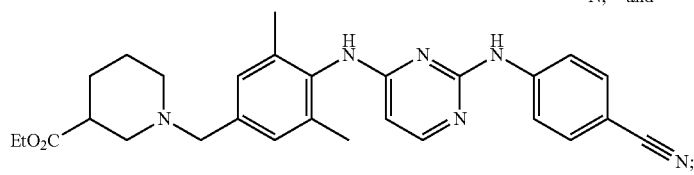
and
an N-oxide, a pharmaceutically acceptable addition salt, a quaternary amine or a stereochemically isomeric form thereof.
* * * * *